(12) United States Patent
Silver et al.

(10) Patent No.: US 11,535,673 B2
(45) Date of Patent: Dec. 27, 2022

(54) CHIMERIC ACTIVATORS: QUANTITATIVELY DESIGNED PROTEIN THERAPEUTICS AND USES THEREOF

(75) Inventors: Pamela A. Silver, Cambridge, MA (US); Pablo Gabriel Cironi Lopez, Madrid (ES); David G. Miguez, Barcelona (ES)

(73) Assignee: President and Fellows of Harvard College, Cambridge, MA (US)

( * ) Notice: Subject to any disclaimer, the term of this patent is extended or adjusted under 35 U.S.C. 154(b) by 196 days.

(21) Appl. No.: 12/594,747

(22) PCT Filed: Apr. 5, 2008

(86) PCT No.: PCT/US2008/004435
§ 371 (c)(1),
(2), (4) Date: Apr. 16, 2010

(87) PCT Pub. No.: WO2008/124086
PCT Pub. Date: Oct. 16, 2008

(65) Prior Publication Data
US 2011/0274658 A1    Nov. 10, 2011

Related U.S. Application Data

(60) Provisional application No. 60/910,390, filed on Apr. 5, 2007, provisional application No. 61/005,775, filed on Dec. 7, 2007, provisional application No. 61/065,937, filed on Feb. 15, 2008.

(51) Int. Cl.
| | | |
|---|---|---|
| *C07K 19/00* | (2006.01) | |
| *C07K 14/52* | (2006.01) | |
| *C07K 16/28* | (2006.01) | |
| *C07K 14/485* | (2006.01) | |
| *C07K 14/525* | (2006.01) | |
| *C07K 14/56* | (2006.01) | |
| *C07K 14/575* | (2006.01) | |
| *C07K 16/30* | (2006.01) | |
| *A61K 47/64* | (2017.01) | |
| *A61K 47/68* | (2017.01) | |
| *A61K 38/00* | (2006.01) | |

(52) U.S. Cl.
CPC ........ *C07K 16/2863* (2013.01); *A61K 47/642* (2017.08); *A61K 47/6425* (2017.08); *A61K 47/6813* (2017.08); *A61K 47/6849* (2017.08); *A61K 47/6853* (2017.08); *C07K 14/485* (2013.01); *C07K 14/525* (2013.01); *C07K 14/56* (2013.01); *C07K 14/5759* (2013.01); *C07K 16/2896* (2013.01); *C07K 16/3007* (2013.01); *A61K 38/00* (2013.01); *C07K 2317/34* (2013.01); *C07K 2317/622* (2013.01); *C07K 2317/76* (2013.01); *C07K 2319/30* (2013.01); *C07K 2319/33* (2013.01); *C07K 2319/74* (2013.01)

(58) Field of Classification Search
None
See application file for complete search history.

(56) References Cited

U.S. PATENT DOCUMENTS

| | | | | |
|---|---|---|---|---|
| 5,606,023 | A | * | 2/1997 | Chen .................... C07K 14/525 424/85.2 |
| 5,652,353 | A | * | 7/1997 | Fiers et al. .................... 536/23.5 |
| 6,787,133 | B2 | | 9/2004 | Weinrich et al. |
| 7,186,804 | B2 | | 3/2007 | Gillies et al. |
| 7,294,472 | B2 | | 11/2007 | Gilchrist et al. |
| 2002/0102257 | A1 | | 8/2002 | Johnson |
| 2003/0026779 | A1 | * | 2/2003 | Yu ........................ C07K 14/555 424/85.4 |
| 2003/0138401 | A1 | * | 7/2003 | Dahiyat et al. ............... 424/85.1 |
| 2003/0166163 | A1 | | 9/2003 | Gillies |
| 2004/0219131 | A1 | * | 11/2004 | Patten .................... A61K 47/60 424/85.7 |
| 2005/0036951 | A1 | | 2/2005 | Henderson |
| 2005/0089888 | A1 | * | 4/2005 | Shaw et al. ........................ 435/6 |
| 2006/0263368 | A1 | | 11/2006 | Rosenblum et al. |
| 2008/0171363 | A1 | | 7/2008 | Patten et al. |

(Continued)

FOREIGN PATENT DOCUMENTS

| | | |
|---|---|---|
| WO | WO 99/16889 A1 | 4/1999 |
| WO | 2001/062931 A2 | 8/2001 |

(Continued)

OTHER PUBLICATIONS

Cironi et al. Ehancement of cell type specificity by quantititative modulation of a chimeric ligand. The Journal of Biological Chemistry, vol. 283/No. 13:8469-8476 (Mar. 28, 2008).*

(Continued)

*Primary Examiner* — Elizabeth C. Kemmerer
*Assistant Examiner* — Regina M DeBerry
(74) *Attorney, Agent, or Firm* — Nixon Peabody LLP; David S. Resnick; Nicole D. Kling

(57) ABSTRACT

Aspects of the invention provide methods for harnessing the potential of proteins that occur naturally (e.g., in humans) and that have serious but finite toxicity. Aspects of the invention relate to a quantitative systems-biological and structural approach to design a class Mof chimeric proteins that avoid the toxicity of protein drugs while retaining their desired activities. In particular, chimeric proteins containing a variant form of a natural protein fused to a targeting moiety may be administered to a subject to target a signal (e.g., induction of apoptosis) to particular cells without having a generalized toxic effect.

9 Claims, 21 Drawing Sheets

Specification includes a Sequence Listing.

(56) References Cited

U.S. PATENT DOCUMENTS

| | | |
|---|---|---|
| 2008/0214436 A1 | 9/2008 | Yu et al. |
| 2008/0279823 A1* | 11/2008 | Schreiber ............... C07K 14/56 424/85.7 |
| 2009/0238789 A1* | 9/2009 | Guyon et al. ................ 424/85.2 |
| 2010/0003266 A1* | 1/2010 | Simon .............. A61K 47/48753 424/178.1 |
| 2012/0178139 A1 | 7/2012 | Hubbell et al. |

FOREIGN PATENT DOCUMENTS

| | | |
|---|---|---|
| WO | WO 2005/033134 A2 | 4/2005 |
| WO | WO 2006/074451 A2 | 7/2006 |
| WO | WO 2007/000769 A2 | 1/2007 |
| WO | 2007/092537 A2 | 8/2007 |
| WO | WO-2007/089753 A2 * | 8/2007 |

OTHER PUBLICATIONS

Taylor et al. Anti-glycophorin single-chain Fv fusion to low-affinity mutant erythropoietin improves red blood cell-lineage specificity. Protein Engineering, Design & Selection vol. 23 No. 4 pp. 251-260 (2010).*

Wang-Qiu et al. Enhanced tumor effect of an IFN-gamma EGF fusion protein. Biomedical and Environmental Sciences. vol. 10: 387-395 (1997). (Year: 1997).*

Cironi et al. Enhancement of Cell Type Specificity by Quantitative Modulation of a Chimeric Ligand. The Journal of Biological Chemistry vol. 283, No. 13, pp. 8469-8476 (Mar. 28, 2008). (Year: 2008).*

Adam et al. Reduction of dimensionality in biological diffusion processes. Structural Chemistry and Molecular Biology. 1968:198-215.

Adamson et al., Analysis of erythropoiesis by erythroid colony formation in culture. Blood Cells. 1978;4(1-2):89-103.

Assohou-Luty et al., A CD40-CD95L fusion protein interferes with CD40L-induced prosurvival signaling and allows membrane CD40L-restricted activation of CD95. J Mol Med. Sep. 2006;84(9):785-97. Epub Aug. 4, 2006.

Bellot et al., High-affinity epidermal growth factor binding is specifically reduced by a monoclonal antibody, and appears necessary for early responses. J Cell Biol. Feb. 1990;110(2):491-502.

Blair et al., HIV-1 entry—an expanding portal for drug discovery. Drug Discov Today. May 2000;5(5):183-194.

Boehm et al., Structural models for carcinoembryonic antigen and its complex with the singlechain Fv antibody molecule MFE23. FEBS Lett. Jun. 9, 2000;475(1):11-6.

Bremer et al., CD7-restricted activation of Fas-mediated apoptosis: a novel therapeutic approach for acute T-cell leukemia. Blood. Apr. 1, 2006;107(7):2863-70. Epub Dec. 6, 2005.

Bremer et al., Simultaneous inhibition of epidermal growth factor receptor (EGFR) signaling and enhanced activation of tumor necrosis factor-related apoptosis-inducing ligand (TRAIL) receptor-mediated apoptosis induction by an scFv:sTRAIL, fusion protein with specificity for human EGER. J Biol Chem. Mar. 18, 2005;280(11):10025-33. Epub Jan. 11, 2005.

Bremer et al., Target cell-restricted and -enhanced apoptosis induction by a scFv:sTRAIL fusion protein with specificity for the pancarcinoma-associated antigen EGP2. Int J Cancer. Mar. 20, 2004;109(2):281-90.

Caraglia et al., Interferon-alpha induces apoptosis in human KB cells through a stress-dependent mitogen activated protein kinase pathway that is antagonized by epidermal growth factor. Cell Death Differ. Aug. 1999;6(8):773-80.

Catimel et al., Kinetics of the autologous red cell agglutination test. J Immunol Methods. Oct. 15, 1993;165(2):183-92.

Chan et al., HIV entry and its inhibition. Cell. May 29, 1998;93(5):681-4.

Cho et al., Structure of the extracellular region of HER2 alone and in complex with the Herceptin Fab. Nature. Feb. 13, 2003;421(6924):756-60.

Clare et al., Production of mouse epidermal growth factor in yeast: high-level secretion using Pichia pastoris strains containing multiple gene copies. Gene. Sep. 15, 1991;105(2):205-12.

Crawford, Erythropoietin: high profile, high scrutiny. J Clin Oncol. Mar. 20, 2007;25(9):1021-3. Epub Feb. 20, 2007.

Czerwinski et al., Only selected light chains combine with a given heavy chain to confer specificity for a model glycopeptide antigen. J Immunol. May 1, 1998;160(9):4406-17.

Elliott et al., Mapping of the active site of recombinant human erythropoietin. Blood. Jan. 15, 1997;89(2):493-502.

Evinger et al., Assay of growth inhibition in lymphoblastoid cell cultures. Methods Enzymol. 1981;79(Pt B):362-8.

Franklin et al., Insights into ErbB signaling from the structure of the ErbB2-pertuzumab complex. Cancer Cell. Apr. 2004;5(4):317-28.

French et al., Intracellular trafficking of epidermal growth factor family ligands is directly influenced by the pH sensitivity of the receptor/ligand interaction. J Biol Chem. Mar. 3, 1995;270(9):4334-40.

Garcia et al., High level expression of human ifn-alpha2b in pichia pastoris. Biotecnologia Aplicada. 1995;12(3):152-155. Last accessed at http://www.bioline.org.br/request?ba95052 on Mar. 16, 2004.

Garrett et al., Crystal structure of a truncated epidermal growth factor receptor extracellular domain bound to transforming growth factor alpha. Cell. Sep. 20, 2002;110(6):763-73.

Giles et al., Gemtuzumab ozogamicin in the treatment of acute myeloid leukemia. Cancer. Nov. 15, 2003;98(10):2095-104.

Hass et al., Preparation of synthetic polypeptide domains of carcinoembryonic antigen and their use in epitope mapping. Cancer Res. Apr. 1, 1991;51(7):1876-82.

Heimbrook et al., Transforming growth factor alpha-Pseudomonas exotoxin fusion protein prolongs survival of nude mice bearing tumor xenografts. Proc Natl Acad Sci U S A. Jun. 1990;87(12):4697-701.

Henke et al., Do erythropoietin receptors on cancer cells explain unexpected clinical findings? J Clin Oncol. Oct. 10, 2006;24(29):4708-13. Erratum in: J Clin Oncol. Apr. 10, 2007;25(11):1457.

Henke et al., Erythropoietin to treat head and neck cancer patients with anaemia undergoing radiotherapy: randomised, double-blind, placebo-controlled trial. Lancet. Oct. 18, 2003;362(9392):1255-60.

Huang et al., A trimeric anti-HER2/neu ScFv and tumor necrosis factor-alpha fusion protein induces HER2/neu signaling and facilitates repair of injured epithelia. J Pharmacol Exp Ther. Mar. 2006;316(3):983-91. Epub Nov. 15, 2005.

Huston et al., Antigen recognition and targeted delivery by the single-chain Fv. Cell Biophys. Jan.-Jun. 1993;22(1-3):189-224.

Hymowitz et al., A unique zinc-binding site revealed by a high-resolution X-ray structure of homotrimeric Apo2L/TRAIL. Biochemistry. Feb. 1, 2000;39(4):633-40.

Iqbal Ahmed et al., Interferon alpha2b gene delivery using adenoviral vector causes inhibition of tumor growth in xenograft models from a variety of cancers. Cancer Gene Ther. Oct. 2001;8(10):788-95.

Khuri, Weighing the hazards of erythropoiesis stimulation in patients with cancer. N Engl J Med. Jun. 14, 2007;356(24):2445-8.

Kreitman et al., Handbook of Experimental Pharmacology. Chapter 5: Targeted Toxin Hybrid proteins. 1999:89-110.

Kuan et al., Increased binding affinity enhances targeting of glioma xenografts by EGFRvIII-specific scFv. Int J Cancer. Dec. 15, 2000;88(6):962-9.

Leyland-Jones et al., Maintaining normal hemoglobin levels with epoetin alfa in mainly nonanemic patients with metastatic breast cancer receiving first-line chemotherapy: a survival study. J Clin Oncol. Sep. 1, 2005;23(25):5960-72. Epub Aug. 8, 2005.

Liu et al., Growth factor receptor expression varies among high-grade gliomas and normal brain: epidermal growth factor receptor has excellent properties for interstitial fusion protein therapy. Mol Cancer Ther. Aug. 2003;2(8):783-7.

Lorberboum-Galski et al., Cytotoxic activity of an interleukin 2-Pseudomonas exotoxin chimeric protein produced in *Escherichia coli*. Proc Natl Acad Sci U S A. Mar. 1988;85(6):1922-6.

(56) References Cited

OTHER PUBLICATIONS

Masui et al., Growth inhibition of human tumor cells in athymic mice by anti-epidermal growth factor receptor monoclonal antibodies. Cancer Res. Mar. 1984;44(3):1002-7.
McKay et al., Integrating signals from RTKs to ERK/MAPK. Oncogene. May 14, 2007;26(22):3113-21.
Míguez, The role of asymmetric binding in ligand-receptor systems with 1:2 interaction ratio. Biophys Chem. May 2010;148(1-3):74-81. doi: 10.1016/j.bpc.2010.02.012. Epub Feb. 25, 2010.
Ogiso et al., Crystal structure of the complex of human epidermal growth factor and receptor extracellular domains. Cell. Sep. 20, 2002;110(6):775-87.
Pai et al., Antitumor activity of a transforming growth factor alpha-Pseudomonas exotoxin fusion protein (TGF-alpha-PE40). Cancer Res. Jun. 1, 1991;51(11):2808-12.
Piehler et al., Biophysical analysis of the interaction of human ifnar2 expressed in *E. coli* with IFNalpha2. J Mol Biol. May 28, 1999;289(1):57-67.
Piehler et al., New structural and functional aspects of the type I interferon-receptor interaction revealed by comprehensive mutational analysis of the binding interface. J Biol Chem. Dec. 22, 2000;275(51):40425-33.
Platanias, Mechanisms of type-I- and type-II-interferon-mediated signalling. Nat Rev Immunol. May 2005;5(5):375-86.
Quadt-Akabayov et al., Determination of the human type I interferon receptor binding site on human interferon-alpha2 by cross saturation and an NMR-based model of the complex. Protein Sci. Nov. 2006;15(11):2656-68. Epub Sep. 25, 2006.
Reginato et al., Integrins and EGFR coordinately regulate the pro-apoptotic protein Bim to prevent anoikis. Nat Cell Biol. Aug. 2003;5(8):733-40. Supplementary Information. 1.
Roisman et al., Structure of the interferon-receptor complex determined by distance constraints from double-mutant cycles and flexible docking. Proc Natl Acad Sci U S A. Nov. 6, 2001;98(23):13231-6.
Samel et al., Generation of a FasL-based proapoptotic fusion protein devoid of systemic toxicity due to cell-surface antigen-restricted Activation. J Biol Chem. Aug. 22, 2003;278(34):32077-82. Epub May 28, 2003.
Scherf et al., Cytotoxic and antitumor activity of a recombinant tumor necrosis factor-B1(Fv) fusion protein on LeY antigen-expressing human cancer cells. Clin Cancer Res. Sep. 1996;2(9):1523-31.
Siegall et al., Cytotoxic activities of a fusion protein comprised of TGF alpha and Pseudomonas exotoxin. FASEB J. Dec. 1989;3(14):2647-52.
Southcott et al., The expression of human blood group antigens during erythropoiesis in a cell culture system. Blood. Jun. 15, 1999;93(12):4425-35.
Stauber et al., Crystal structure of the IL-2 signaling complex: paradigm for a heterotrimeric cytokine receptor. Proc Natl Acad Sci U S A. Feb. 21, 2006;103(8):2788-93. Epub Feb. 13, 2006.
Taylor et al., Anti-glycophorin single-chain Fv fusion to low-affinity mutant erythropoietin improves red blood cell-lineage specificity. Protein Eng Des Sel. Apr. 2010;23(4):251-60. doi: 10.1093/protein/gzp085. Epub Jan. 18, 2010.
Todhunter et al., A bispecific immunotoxin (DTAT13) targeting human IL-13 receptor (IL-13R) and urokinase-type plasminogen activator receptor (uPAR) in a mouse xenograft model. Protein Eng Des Sel. Feb. 2004;17(2):157-64. Epub Feb. 13, 2004.
Wajant et al., Differential activation of TRAIL-R1 and -2 by soluble and membrane TRAIL allows selective surface antigen-directed activation of TRAIL-R2 by a soluble TRAIL derivative. Oncogene. Jul. 5, 2001;20(30):4101-6.
Waśniowska et al., Analysis of peptidic epitopes recognized by the three monoclonal antibodies specific for the same region of glycophorin A but showing different properties. Mol Immunol. Jun. 1992;29(6):783-91.
Wright et al., Randomized, double-blind, placebo-controlled trial of erythropoietin in non-small-cell lung cancer with disease-related anemia. J Clin Oncol. Mar. 20, 2007;25(9):1027-32. Epub Feb. 20, 2007.
Wüest et al., TNF-Selectokine: a novel prodrug generated for tumor targeting and site-specific activation of tumor necrosis factor. Oncogene. Jun. 20, 2002;21(27):4257-65.
Zhang et al., Primary targeting of recombinant Fv-immunotoxin hscFv(25)-mTNFalpha against hepatocellular carcinoma. World J Gastroenterol. Jul. 1, 2004;10(13):1872-5.
Zhang et al., Site-directed mutational analysis of human tumor necrosis factor-alpha receptor binding site and structure-functional relationship. J Biol Chem. Nov. 25, 1992;267(33):24069-75.
Zhou et al., Structural definition of a conserved neutralization epitope on HIV-1 gp120. Nature. Feb. 15, 2007;445(7129):732-7.
PCT/US2008/004435, Nov. 13, 2008, International Search Report and Written Opinion.
PCT/US2008/004435, Oct. 15, 2009, International Preliminary Report on Patentability.
GenBank Accession No. AAK85297.Aug. 13, 2001. 1 page.
Jaitin et al., Inquiring into the differential action of interferons (IFNs): an IFN-alpha2 mutant with enhanced affinity to IFNAR1 is functionally similar to IFN-beta. Mol Cell Biol. Mar. 2006;26(5):1888-97.
Jaks et al., Differential receptor subunit affinities of type I interferons govern differential signal activation. J Mol Biol. Feb. 16, 2007;366(2):525-39. Epub Nov. 18, 2006.
Kalie et al., The stability of the ternary interferon-receptor complex rather than the affinity to the individual subunits dictates differential biological activities. J Biol Chem. Nov. 21, 2008;283(47):32925-36. doi: 10.1074/jbc.M806019200. Epub Sep. 18, 2008.
Knappik et al., Fully synthetic human combinatorial antibody libraries (HuCAL) based on modular consensus frameworks and CDRs randomized with trinucleotides. J Mol Biol. Feb. 11, 2000;296(1):57-86.
Kontos et al., Engineering antigens for in situ erythrocyte binding induces T-cell deletion. Proc Natl Acad Sci U S A. Jan. 2, 2013;110(1):E60-8. doi: 10.1073/pnas.1216353110. Epub Dec. 17, 2012.
Kontos et al., Improving protein pharmacokinetics by engineering erythrocyte affinity. Mol Pharm. Dec. 6, 2010;7(6):2141-7. doi: 10.1021/mp1001697. Epub Sep. 17, 2010.
Robinson-Mosher et al., Dynamics simulations for engineering macromolecular interactions. Chaos. Jun. 2013;23(2):025110. doi: 10.1063/1.4810915.
Roisman et al., Mutational analysis of the IFNAR1 binding site on IFNalpha2 reveals the architecture of a weak ligand-receptor binding-site. J Mol Biol. Oct. 21, 2005;353(2):271-81.
Streuli et al., Target cell specificity of two species of human interferon-alpha produced in *Escherichia coli* and of hybrid molecules derived from them. Proc Natl Acad Sci U S A. May 1981;78(5):2848-52.
Bachoo et al. "Epidermal growth factor receptor and Ink4a/Arf: convergent mechanisms governing termina differentiation and transformation along the neural stem cell to astrocyte axis" Cancer Cell 1(3):269-277 (2002).
Barbas et al. "In vitro evolution of a neutralizing human antibody to human immunodeficiency virus type 1 to enhance affinity and broaden strain cross-reactivity." PNAS 91(9):3809-3813 (1994).
Barker et al. "Effect of a chimeric anti-ganglioside GD2 antibody on cell-mediated lysis of human neuroblastoma cells." Cancer Research 51(1):144-149 (1991).
Brown et al. "Iac repressor can regulate expression from a hybrid SV40 early promoter containing a Iac operator in animal cells." Cell 49(5):603-612 (1987).
Daly et al. "Expression of heterologous proteins in Pichia pastoris: a useful experimental tool in protein engineering and production." Journal of Molecular Recognition 18(2):119-138 (2005).
Gossen et al. "Tight control of gene expression in mammalian cells by tetracycline-responsive promoters." PNAS 89(12):5547-5551 (1992).

(56) References Cited

OTHER PUBLICATIONS

Hawkins et al. "Selection of phage antibodies by binding affinity: mimicking affinity maturation." Journal of Molecular Biology 226(3):889-896 (1992).

Jackson et al. "In vitro antibody maturation Improvement of a high affinity, neutralizing antibody against IL-1 beta." The Journal of Immunology 154(7):3310-3319 (1995).

Johns et al. "Identification of the epitope for the epidermal growth factor receptor-specific monoclonal antibody 806 reveals that it preferentially recognizes an untethered form of the receptor." Journal of Biological Chemistry 279(29):30375-30384 (2004).

Kaufman et al. "Amplification and expression of sequences cotransfected with a modular dihydrofolate reductase complementary DNA gene." Journal of Molecular Biology 159(4):601-621 (1982).

Keppler et al. "A general method for the covalent labeling of fusion proteins with small molecules in vivo." Nature Biotechnology 21(1):86-89 (2003).

Marks et al. "By-Passing Immunization: Building High Affinity Human Antibodies by Chain Shuffling." Nature Biotechnology 10(7):779-783 (1992).

Modjtahedi et al. "Targeting of cells expressing wild-type EGFR and type-III mutant EGFR (EGFRvIII) by anti-EGFR MAb ICR62: A two-pronged attack for tumour therapy." International Journal of Cancer 105(2):273-280 (2003).

Murzin et al., "SCOP: a structural classification of proteins database for the investigation of sequences and structures." Journal of Molecular Biology 247(4):536-540 (1995).

Pabo et al. "The lambda repressor contains two domains." PNAS 76(4):1608-1612 (1979).

Powers et al. "Expression of single-chain Fv-Fc fusions in Pichia pastoris." Journal of Immunological Methods 251(1):123-135 (2001).

Schier et al. "Identification of functional and structural amino-acid residues by parsimonious mutagenesis." Gene 169(2):147-155 (1996).

Shockett et al. "A modified tetracycline-regulated system provides autoregulatory, inducible gene expression in cultured cells and transgenic mice." PNAS 92(14):6522-6526 (1995).

Singhal et al., "Antibody-mediated targeting of liposomes to red cells in vivo." FEBS Letters 201(2):321-326 (1986).

Snitkovsky et al., "A TVA-single-chain antibody fusion protein mediates specific targeting of a subgroup A avian leukosis virus vector to cells expressing a tumor-specific form of epidermal growth factor receptor." Journal of Virology 74(20):9540-9545 (2000).

Urlaub et al. "Isolation of Chinese hamster cell mutants deficient in dihydrofolate reductase activity." PNAS 77(7):4216-4220 (1980).

Yelton et al. "Affinity maturation of the BR96 anti-carcinoma antibody by codon-based mutagenesis." The Journal of Immunology 155(4):1994-2004 (1995).

Deller et al., "Crystal structure and functional dissection of the cytostatic cytokine oncostatin M." Structure 8(8):863-874 (2000).

Eletkjall et al., "Distinct structural elements in GDNF mediate binding to GFRα1 and activation of the GFRα1-c-Ret receptor complex." The EMBO journal 18(21):5901-5910 (1999).

Keyt et al., "Identification of vascular endothelial growth factor determinants for binding KDR and FLT-1 receptors Generation of receptor-selective VEGF variants by site-directed mutagenesis." Journal of Biological Chemistry 271(10):5638-5646 (1996).

Lyu et al., "The immunocytokine scFv23/TNF sensitizes HER-2/neu-overexpressing SKBR-3 cells to tumor necrosis factor (TNF) via up-regulation of TNF receptor-1." Molecular Cancer Therapeutics 4(8):1205-1213 (2005).

\* cited by examiner

CHIMERIC ACTIVATORS: QUANTITATIVELY DESIGNED PROTEIN THERAPEUTICS AND USES THEREOF

RELATED APPLICATIONS

This application is a national stage filing under 35 U.S.C. 371 of international application PCT/US2008/004435, filed Apr. 5, 2008, which was published under PCT Article 21(2) in English, and which claims the benefit under 35 U.S.C. § 119(e) from U.S. provisional applications Ser. No. 60/910,390 filed Apr. 5, 2007, Ser. No. 61/005,775 filed Dec. 7, 2007 and Ser. No. 61/065,937 filed Feb. 15, 2008, the entire contents of which are herein incorporated by reference.

FIELD OF THE INVENTION

The invention relates to chimeric proteins, fusion proteins, and therapeutic proteins.

BACKGROUND OF THE INVENTION

Many therapeutic proteins such as interferon alpha (IFNα), TNF and IL-2 act locally in their natural state. Systemic administration of these proteins results in side effects that limit the dose levels that can be used therapeutically. For example, IFNα is useful in treating hepatitis and certain cancers, but causes side effects such as flu-like symptoms and suicidal thoughts. There are needs for targeting mechanisms to permit therapeutic proteins to be delivered locally and to minimize the side effects of systemic administration of therapeutic proteins.

Several laboratories have performed protein-based targeting of toxins to cancer cells. The laboratory of Ira Pastan has been working on cancer-targeted toxins for many years. In 1987, this group described a chimeric protein consisting of *Pseudomonas* exotoxin and TGFα. This toxin normally binds to the cell surface, is internalized into the endosome, and then somehow enters the cytoplasm where it inactivates Elongation Factor II. TGFα is an EGF-like ligand that binds to EGF receptor. Over the years, the Pastan group has fused variants of this exotoxin to diverse ligands and antibody V regions that bind to cell surface receptors. Some of these have been in Phase I/II-type clinical trials, but none have shown enough efficacy to be developed further. Thus, in addition to the needs for targeting mechanisms to permit therapeutic proteins to be delivered locally and to minimize the side effects of systemic administration of therapeutic proteins, there is also a need to maintain the efficacy of therapeutic proteins while meeting one or both of these two needs.

Another example of protein-based targeting of toxins to cancer cells is Mylotarg™ Mylotarg™ is a monoclonal antibody chemically conjugated to the toxin calicheamycin (Giles et al. (2003) Cancer 98: 2095). Calicheamycin causes double-stranded breaks in DNA and is highly toxic. However, when covalently bonded to an antibody, this chemical is not toxic because it has no access to DNA. When Mylotarg™ binds to the CD33 receptor protein on a tumor cell, the antibody-receptor complex is internalized and the antibody is degraded. The calicheamycin is then liberated to bind to the DNA of the tumor cell. Mylotarg™ received accelerated approval by the FDA for treatment of acute myelogenous leukemia (AML) in 2000.

Other examples are Zevalin™ and Bexxar™. Zevalin™ and Bexxar™ consist of radioisotopes chemically conjugated to monoclonal antibodies against the B cell marker CD20. These proteins are use to treat B cell lymphoma. The radioisotopes used, yttrium-90 and iodine-131 respectively, have short decay path-lengths, so that when the antibody binds to the surface of a tumor cell, there is local irradiation of the tumor. Zevalin™ was approved by the FDA in 2002. Bexxar™ was approved in 2003.

Thus far, targeting of toxic molecules to specific cells has been successful for the delivery of small molecules (such as radioisotope delivery by conjugates such as Zevalin™ and Bexxar™ and delivery of a chemical toxin in Mylotarg™), but not for the delivery of cell-killing proteins such as *Pseudomonas* exotoxin, RNAse, tumor necrosis factor, or interferons. A consistent problem has been that the toxic proteins act on bystander cells as they are being delivered to target tissue.

SUMMARY OF THE INVENTION

Aspects of the invention relate to methods and compositions for specifically targeting the activity of naturally-occurring proteins to certain cells or tissues where their activity can be therapeutically useful. In some aspects, the invention provides therapeutic applications for naturally-occurring proteins that otherwise have serious but finite toxicity. Methods and compositions of the invention can be used to target the cell-activating properties of a protein to a subset of target cells without activating non-target cells. Aspects of the invention relate to chimeric proteins that include a variant of a cell-activating element (also referred to herein as an Activity element) that has reduced cell-activating properties relative to its wild-type counterpart. The chimeric proteins also include a cell-targeting element (also referred to herein as a targeting element) that preferentially binds to target cells of interest. The cell-activating variant and the cell-targeting element are connected via a linker. According to aspects of the invention, the activating and targeting elements are selected so that the resulting chimeric protein only activates cells that are bound by the targeting element. The activating element variant is selected such that it can only activate a cell when present in a sufficiently high amount (e.g., concentration) on or near a cell-surface. The targeting element is selected such that it can target a sufficient amount of the activating element to the surface of a target cell in order to activate it. In some embodiments, the linker is selected so that it allows simultaneous binding of the activating and targeting elements to different receptors on the target cell. Accordingly, chimeric proteins of the invention can be used to avoid or reduce unwanted side effects caused by the activating element activating non-target cells.

Aspects of the invention are particularly useful for targeting the activity of toxic activating elements to target cells (e.g., to target cytotoxic elements to cancer cells) without killing surrounding non-target cells. Aspects of the invention can be useful to harness certain functions of natural proteins that otherwise may be toxic (or have serious toxic side effects) when administered therapeutically. For example, IFNα is normally secreted by virus-infected cells and promotes the death of cells in the immediate vicinity. TNF is secreted in response to the presence of bacterial molecules such as lipopolysaccharide and is thought to play an important role in wound-healing. Other similar molecules include, but are not limited to, IFNβ, IL-2, IFNγ, and IL-1. These therapeutic proteins are usually administered systemically and all have serious side effects, but nonetheless can be very useful. Erythropoietin can also have serious side effects when treating anemia associated with cancer, since erythropoietin can stimulate the growth and survival of certain cancer cells. However, by using less active variants of these proteins in combination with targeting elements of the invention, the general toxicity of protein drugs can be avoided while retaining desired activities (e.g., cell killing activities, enzymatic activities, signal transduction activities, etc., or any combination thereof).

In some embodiments, a recombinant protein of the invention includes a first element that binds to a first receptor on a target cell; a second element that binds to a second receptor on the target cell; and, optionally, a linker that connects the first and second elements, wherein the linker allows the first and second elements to bind simultaneously to the first and second receptors on the target cell, wherein the first element comprises a mutation that reduces its binding affinity for its receptors, and wherein the first element transmits a signal to the host cell when it is bound to the first receptor. In some embodiments, the first element is an enzyme, a substrate, a receptor, a ligand, or other peptide that can interact (e.g., bind to and/or catalyze a reaction and/or transduce a signal) to the receptor on the cell surface. It should be appreciated that the receptor may be any cell-surface protein that can receive a signal (e.g., resulting in a molecular and/or cellular change) upon interaction with the first element. In some embodiments, the first element is a variant of an activity element that binds to and/or interacts with more than one receptor (e.g., 2, 3, 4, 5 or more different receptors) in nature. In some embodiments, the variant activity element (e.g., a natural or engineered mutant element) has reduced affinity for one or more of its natural receptors (e.g., for about 10%-20%, about 20%-40%, about 50%, about 40%-60%, about 60%-80%, about 80%-100% or for all of the different natural receptors). In particular, a variant activity element may have reduced binding affinity for the receptor (e.g., a signal transduction receptor, enzyme, or other cell surface molecule that can mediate a signal or other desired biochemical or cellular change) or receptors that are being targeted for activation in the target cells. Accordingly, a variant activity element may have reduced signaling (e.g., more than about 10%, more than about 25%, more than about 50%, more than about 75%, more than about 80%, more than about 90%, or more than about 95% loss of signaling activity, or complete loss of detectable signaling activity) via the receptor(s) of interest in the absence of the targeting element when compared to the wild-type activity element.

In some embodiments, recombinant proteins of the invention may bind to their target cells as monomers. In some embodiments, the targeting element binds to its target molecule as a monomer (e.g., as a single copy of the targeting element such as a single copy of an antibody). In some embodiments, the activity element interacts with its receptor or target as a monomer. In some embodiments, both the targeting and activity elements interact with their receptors or targets as monomers. In some embodiments, the cell-surface receptors themselves are monomers. However, they may be multimers as the invention is not limited in this respect.

In some embodiments, the first and second elements are connected via a linker. A linker may be any suitable length as described herein (e.g., about 5-10, about 10-20, about 25, about 20-50, about 50, about 50-70 amino acids long, or longer or shorter). In some embodiments, the linker may be flexible.

Accordingly, aspects of the invention relate to chimeric activators including an activity element and a targeting element, optionally joined by a linker, wherein the targeting element binds to a first binding site on a target cell, and wherein the activity element binds to a second binding site on a target cell, and wherein the linker length has been optimized for maximizing binding efficiency of the activity element to the second binding site when the targeting element is bound to the first binding site. In some embodiments the first binding site is a ligand binding site, a receptor, or an epitope on a cell surface. In some embodiments the second binding site is a signal-transduction receptor on a cell surface. In some embodiments the targeting element is an antibody, an antibody fragment, an Fc region, a natural or synthetic ligand, or a protein interaction motif. In some embodiments the activity element is a cytokine, a cytotoxic protein, a regulatory protein, or an active fragment of any one thereof.

Described herein are chimeric activators wherein the linker length has been optimized. In some embodiments the linker length is at least equal to the minimum distance between the first and second binding sites on the cell surface. In some embodiments the linker length is at least twice the minimum distance between the first and second binding sites on the cell surface. In some embodiments the linker length is at most five-six times the minimum distance between the first and second binding sites on the cell surface. In some embodiments the activity element is mutated such that the binding affinity of the activity element for the second binding site is lower than the binding affinity of the targeting element for the first binding site.

Aspects of the invention relate to methods for manufacturing a chimeric activator including an activity element and a targeting element joined by a linker, wherein the targeting element binds to a first binding site on a target cell, and wherein the activity element binds to a second binding site on a target cell, and wherein the linker length has been optimized for maximizing binding efficiency of the activity element to the second binding site when the targeting element is bound to the first binding site. In some embodiments methods include: i) optimizing the linker length as a function of the concentration of the first and second binding sites, the size of the activity element and targeting element, the minimum distance between the binding sites of the targeting element and the activity element, and the affinities of the activity element and the targeting element for the first and second binding sites; and ii) preparing a chimeric activator having an optimal linker length.

In some embodiments, methods include: i) mutating the activity element such that the binding affinity of the activity element for the second binding site is lower than the binding affinity of the targeting element for the first binding site; i) optimizing the linker length as a function of the concentration of the first and second binding sites, the size of the activity element and targeting element, the minimum distance between the binding sites of the targeting element and the activity element, and the affinities of the activity element and the targeting element for the first and second binding sites; and iii) preparing a chimeric activator.

Aspects of the invention relate to methods for targeted cellular regulation, the method including: administering to a subject a therapeutically effective amount of a chimeric activator including an activity element and a targeting element joined by a linker, wherein the targeting element binds to a first binding site on a target cell, and wherein the activity element binds to a second binding site on a target cell, and wherein the linker length has been optimized for maximizing binding efficiency of the activity element to the second binding site when the targeting element is bound to the first binding site.

Further described herein are methods for treating cancer, the method including: administering to a subject having a cancer a therapeutically effective amount of a composition including a chimeric activator including an activity element and a targeting element joined by a linker, wherein the targeting element binds to a first binding site on a target cell, and wherein the activity element binds to a second binding site on a target cell, and wherein the linker length has been optimized for maximizing binding efficiency of the activity element to the second binding site when the targeting element is bound to the first binding site.

However, it should be appreciated that aspects of the invention may be used to selectively target any activity (e.g., any activity mediated by a cell surface receptor) to target cells that selectively express a cell surface marker that is different (or expressed at different, for example higher, levels) than on non-target cells. Accordingly, aspects of the invention may be used to target cytotoxic or cytostatic activity to any cells associated with a disease or disorder (e.g., cancer cells, immune system cells associated with allergic or chronic inflammatory disorders or reactions, infected cells, pathogen cells, cells that are degenerating, or any other target cells of interest). Aspects of the invention also may be used to selectively deliver other activating signals to target cells (e.g., other than cytotoxic or cytostatic). For example, other activating signals may include on or more proliferation, differentiation, stimulation, or other signals that may be useful in different applications. These and other aspects of the invention are described in more details herein.

DETAILED DESCRIPTION OF THE INVENTION

Figure 1:
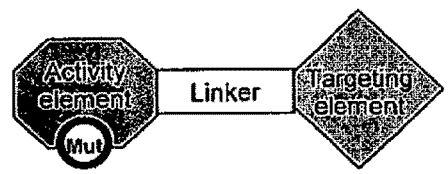
FIG. 1 illustrates a non-limiting embodiment of a general structure of a Chimeric Activator ("mut" indicates that the activity element has a mutation)

Aspects of the invention relate to chimeric proteins that include a targeting element connected to an activity element. In some embodiments, the targeting element binds to molecules that are selectively present on target cells. In some embodiments, the activity element is a variant of a naturally occurring protein that activates cells by binding to one or more cell surface receptors. The variant is selected such that it has reduced or no cell activating properties in the absence of the targeting element. The targeting element is selected such that it selectively binds to target cells thereby increasing the local concentration of the variant activity element on the target cells to a level that results in activation of those cells. In some embodiments, cell activation results in cell death or a reduction or absence of cell proliferation. However, it should be appreciated that other forms of cell activation may be targeted to specific cells using methods and compositions described herein.

An activity element may be a receptor binding protein (or functional portion or domain thereof) that binds to one or more naturally-occurring receptors on a cell surface, thereby mediating signaling to the cell (e.g., via signal transduction). A variant activity element may include one or more naturally occurring and/or engineered mutations that result in reduced binding to one or more (e.g., all) natural receptors that are bound by the wild-type activity element. For example, the binding affinity of the variant activity element for one or more of its receptors may be at least 2 fold lower and preferably at least 5 fold lower or 8 fold lower (e.g., at least 10 fold lower, about 10-50 fold lower, about 50-100 fold lower, about 100-150 fold lower, about 150-200 fold lower, or more than 200 fold lower) than the binding affinity of the wild-type activity element for its natural receptor(s). As a result, in some embodiments the activity element by itself is significantly less active (e.g., substantially inactive) because it cannot bind to its receptor(s). Accordingly, chimeric proteins of the invention are useful to avoid unwanted side effects caused by the activity element binding to its natural receptor on non-target cells. However, the activity element is active on target cells because the targeting element provides the missing binding affinity required for activation.

A targeting element may be a receptor binding protein, an antibody, or any other natural or engineered protein that binds to a molecule that is preferentially present on target cells of interest relative to non-target cells. According to some embodiments of the invention, the affinity of the targeting element for its target molecule (e.g., receptor) may be similar to the binding affinity of the variant activity element for its receptor(s). However, the affinity of the targeting element for its target molecule is typically higher (e.g., at least 2 fold, at least 5 fold, about 5-10 fold, about 10-50 fold, about 50-100 fold, about 100-500 fold, about 500-1,000 fold, at least 1,000 fold, at least 10,000 fold, or at least 100,000 fold higher) than the binding affinity of the variant activity element for its receptor(s).

In some embodiments, the activity and targeting elements are connected via a linker. The linker may be a natural or artificial peptide that provides sufficient flexibility to allow both the targeting element and the activity element of a chimeric activator to bind simultaneously to their targets and/or receptors on a target cell. The linker length may be optimized for the sizes of the target molecules and/or receptors being bound by targeting and activity elements, the sizes of the targeting and activity elements themselves, and other factors described herein in more detail. However, in some embodiments, a linker may not be required (or only a short linker may be required) if one or both of the targeting and activity elements are flexible or are connected to each other by flexible domains.

Accordingly, aspects of the invention relate to Chimeric Activators—proteins that include a targeting element and an activity element that are capable of simultaneously binding to multiple (two or more) unrelated receptors on the same target cell. In some embodiments, a Chimeric Activator has an activity element, a linker, and a targeting element. See, for example, FIG. 1. It should be appreciated that the linker, if present, is located between the targeting and activity elements. However, aspects of the invention are not limited by the relative positions of the targeting and activity elements. For example, the targeting element may be N-terminal to the activity element (regardless of whether a linker separates the two elements). Alternatively, the activity element may be N-terminal to the targeting element (regardless of whether a linker separates the two elements). In addition, proteins of the invention may include one or more additional peptide elements (at the N-terminus, the C-terminus, or within the protein) for purification and/or detection (e.g., peptide tags), stability, function (e.g., secretion and or other function), etc., or any combination thereof. It should be appreciated that targeting and activity elements may bind to overlapping types of molecules (e.g., receptors, substrates, enzymes, or other molecules) that are present on a cell surface. However, in any particular configuration, the element that is being used as a targeting element has sufficient affinity to target a chimeric protein to a cell-surface molecule that is preferentially (e.g., uniquely or selectively or specifically) present or exposed on a target cell of interest. In contrast, an element that is being used as an activity element may have relatively low affinity for a cell surface molecule. However, the element that is being used as an activity element may interact equally with a molecule that is present on all cell types, but only activates the target cell types due to its linkage to the targeting element. However, it should be appreciated that in some embodiments, both the targeting and activity elements interact with different cell surface molecules that all are preferentially present or exposed on the target cells.

Aspects of the invention may be useful to increase the therapeutic index (e.g., by about 2 fold, about 5 fold, about 10 fold, about 50 fold, about 100 fold, about 200 fold, or more) of any protein therapeutic (e.g., based on a naturally occurring or engineered protein or fragment thereof) by reducing the general toxicity of the protein and maintaining or increasing the selective effect of the protein on target cells or tissue. It should be appreciated that aspects of the invention may be used to treat any disease where selective cell activation is beneficial as described herein. In some embodiments, the targeting element may be selected on the basis that it target certain diseased cells (e.g., due to the presence of disease-specific antigens on the target cells). However, in certain embodiments, specific cell types or tissue types may be targeted (e.g., via cell or tissue specific cell surface antigens). In some embodiments, pathogen-specific molecules may be targeted (e.g., on the cells of a pathogen or on host cells infected with a pathogen).

Accordingly, methods and compositions described herein have broad application to treating disorders, including infections, cancer, anemia, allergy, and many other disorders where it is beneficial to activate (e.g., kill, stimulate or otherwise activate) one or more particular cell types. In some embodiments, the invention is useful to treat cancer. Cancer is disease characterized by uncontrolled cell proliferation and other malignant cellular properties. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

In some embodiments, a targeting element comprises a protein component that selectively directs the binding of the chimeric protein to the surface of a desired cell or cells. Accordingly, a targeting element binds specifically to a cell-surface moiety (e.g., an antigen, epitope, protein, glycoprotein, lipid, carbohydrate, or other molecule or portion thereof) that is either only present or exposed on the target cell or is present or exposed in higher amounts on the target cell relative to non-target cells (e.g., about 2 fold, about 5 fold, about 10 fold, about 50 fold, about 100 fold, about 200 fold, about 500 fold, about 1,000 fold, about 10,000 fold, or more on the target cell). The targeting element can be any protein that binds to a cell-surface molecule. Targeting elements typically target to a subset of cells, such as tumor cells. In some embodiments a targeting element is an antibody or a portion of an antibody. In certain embodiments a targeting element is a ligand (e.g., a naturally occurring ligand or portion thereof that retains binding properties, or a synthetic ligand that binds, for example, to a receptor on a target cell).

In specific embodiments, the targeting element binds to cancers cells (e.g., is a cancer targeting element). In some embodiments, the targeting element is an antibody, a growth factor, a hormone, a peptide, an aptamer, a cytokine, interferon, vitamin, or a mixture thereof, for example. The antibody may be further defined as a full-length antibody, chimeric antibody, Fab', Fab, F(ab')2, single domain antibody (DAB), Fv, single chain Fv (scFv), minibody, diabody, triabody, or a mixture thereof, for example. In particular embodiments, the antibody is an anti-HER-2/neu antibody, such as scFv23, for example. In additional specific embodiments, the antibody is an anti-gp240 antigen antibody, such as one that comprises scFvMEL, for example.

Significantly, as is well known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859, 205. Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')2, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. In some embodiments, the targeting element of a chimeric protein is an antibody moiety that has been expressed from a single linear nucleic acid as a single peptide and that can fold into a fully functional antibody. In some embodiments, the chimeric protein is expressed from a nucleic acid that encodes a portion of an antibody (e.g., a heavy chain, a light chain, or a portion thereof as described herein) fused to the activity element (via the optional linker). The remainder of the antibody required for specific binding can be provided in trans (e.g., expressed from a different coding sequence in the same cell or expressed in a different cells and mixed in vitro, etc., or any combination thereof). Accordingly, it should be appreciated that a chimeric protein of the invention may be a single linear polypeptide chain or it may include additional polypeptide chains of an antibody or other binding protein required for specific binding to a target molecule.

In some embodiments, the targeting element comprises one or more growth factors, such as, for example, transforming growth factor, epidermal growth factor, insulin-like growth factor, fibroblast growth factor, heregulin, platelet-derived growth factor, vascular endothelial growth factor, or hypoxia inducible factor. In an additional specific embodiment, the cancer cell-targeting moiety comprises one or more hormones, such as human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, insulin-like growth factor-1, leptin, thrombopoietin, angiotensinogen, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or, IL-36, for example, and/or a combination thereof.

In some embodiments, the targeting element comprises one or more cytokines, such as IL1, IL2, IL3, IL4, IL5, IL6, IL7, IL8, IL9, IL10, IL11, IL12, IL13, IL14, IL15, IL-16, IL-17, IL-18, granulocyte-colony stimulating factor, macrophage-colony stimulating factor, granulocyte-macrophage colony stimulating factor, leukemia inhibitory factor, erythropoietin, granulocyte macrophage colony stimulating factor, oncostatin M, leukemia inhibitory factor, IFN-γ, IFN-α, IFN-β, LT-β, CD40 ligand, Fas ligand, CD27 ligand, CD30 ligand, 4-1BBL, TGF-β, IL 1β, IL-1β, IL-1 RA, MIF, IGIF, and/or a combination thereof.

In some embodiments, a targeting element binds to one or more tissue-specific cell surface markers. In some embodiments, a targeting element is based on the natural ligand of tissue-specific cell surface marker (e.g., a targeting element is a recombinant version of a natural ligand or fragment thereof). In some embodiments, a targeting element is binding agent, such as a peptide, antibody, or aptamer, that binds to one or more tissue-specific cell surface markers. Appropriate cell surface markers are known by the skilled artisan. A non-limiting list of exemplary tissue-specific markers includes: B cell surface markers: (Activated B Cells) CD28, CD38, CD69, CD80, CD83, CD86, DPP4, FCER2, IL2RA, TNFRSF8, TNFSF7; (Mature B Cells) CD19, CD22, CD24, CD37, CD40, CD72, CD74, CD79A, CD79B, CR2, IL1R2, ITGA2, ITGA3, MS4A1, ST6GAL1; (Other B cell surface markers) CD1C, CHST10, HLA-A, HLA-DRA, NT5E. T cell surface markers: (Cytotoxic T Cells) CD8A, CD8B1; Helper T Cells: CD4; (Activated T Cells) ALCAM, CD2, CD38, CD40LG, CD69, CD83, CD96, CTLA4, DPP4, HLA-DRA, IL12RB1, IL2RA, ITGA1, TNFRSF4, TNFRSF8, TNFSF7; (Other T cell surface markers) CD160, CD28, CD37, CD3D, CD3G, CD3Z, CD5, CD6, CD7, FAS, KLRB1, KLRD1, NT5E, ST6GAL1; (Natural Killer (NK) cell surface markers) CD2, CD244, CD3Z, CD7, CD96, CHST10, FCGR3B, IL12RB1, KLRB1, KLRC1, KLRD1, LAG3, NCAM1; Monocyte/macrophage surface markers: (Activated Macrophages) CD69, ENG, FCER2, IL2RA; (Other Monocyte/macrophage cell surface markers) ADAM8, C5R1, CD14, CD163, CD33, CD40, CD63, CD68, CD74, CD86, CHIT1, CHST10, CSF1R, DPP4, FABP4, FCGR1A, HLA-DRA, ICAM2, IL1R2, ITGA1, ITGA2, S100A8, TNFRSF8, TNFSF7; Endothelial cell surface markers: ACE, CD14, CD34, CDH5, ENG, ICAM2, MCAM, NOS3, PECAM1, PROCR, SELE, SELP, TEK, THBD, VCAM1, VWF; Smooth muscle cell surface markers: ACTA2, MYH10, MYH11, MYH9, MYOCD; Dendritic cell surface markers: CD1A, CD209, CD40, CD83, CD86, CR2, FCER2, FSCN1; Mast cell surface markers: C5R1, CMA1, FCER1A, FCER2, TPSAB1; Fibroblast (stromal) cell surface markers: ALCAM, CD34, COL1A1, COL1A2, COL3A1, PH-4; Epithelial cell surface markers: CD1D, K6IRS2, KRT10, KRT13, KRT17, KRT18, KRT19, KRT4, KRT5, KRT8, MUC1, TACSTD1; and Adipocyte surface markers: ADIPOQ, FABP4, RETN, and/or a combination of two or more thereof.

According to aspects of the invention, an activity element comprises a protein component that has the desired signaling activity. This component normally binds to a receptor on the surface of the desired target cell. The activity element can be any protein that binds to a cell-surface receptor and stimulates signal transduction. In some embodiments, the activity element is a variant form (e.g., it is mutated) that has an intrinsic binding to its receptor that is weak as compared to the wild-type protein, to the point that binding of the chimeric protein to a cell is driven by the binding of the targeting element to its receptor. For example, the Chimeric Activator first binds to a cell through the targeting element, and after this initial binding step, the mutated activity element is in a high local concentration relative to its own receptor, so binding takes place in spite of the mutation. In contrast, the chimeric protein may not significantly bind to cells that have only the activity element receptor and not the targeting element receptor, because the inherent binding of the activity element is simply too weak. The presence of one or more weakening mutations can be essential to reduce side effects from activation of non-target cells.

Figure 2:
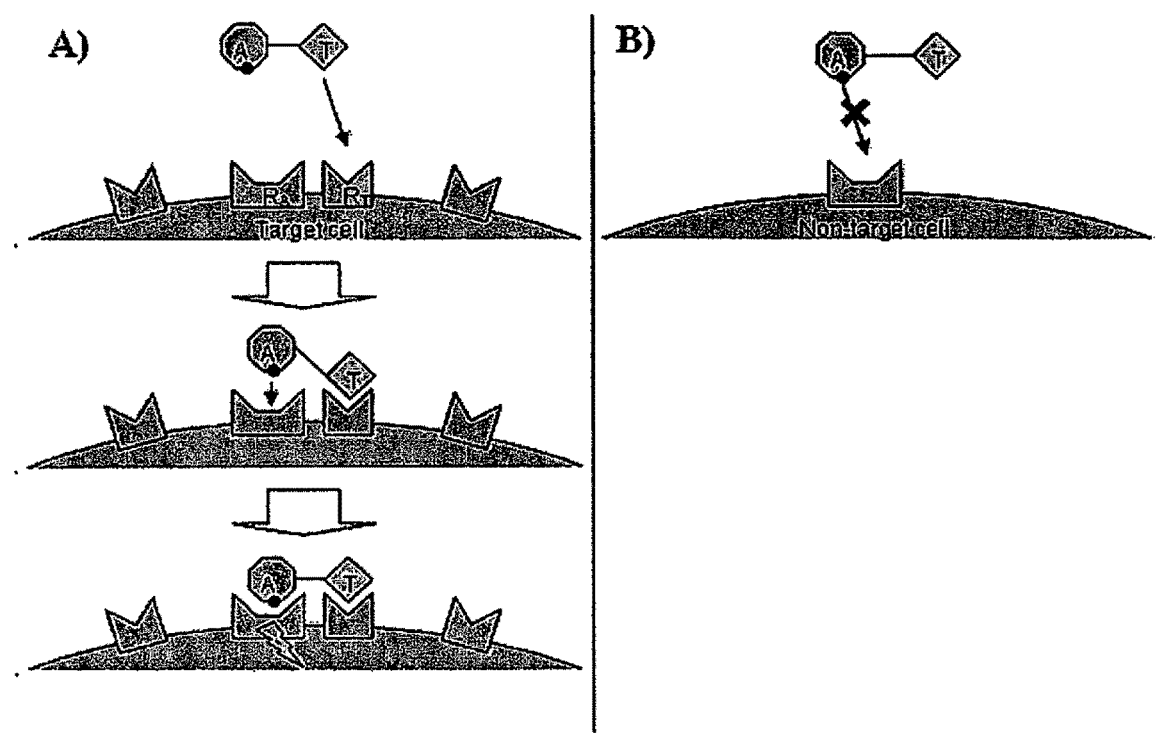
FIG. 2 shows, without wishing to be bound by theory, a proposed mechanism of specific binding of "Chimeric Activators" to target cells.

It should be appreciated that the choice of a particular mutation can be tuned to the on-rates and dissociation constants of the naturally occurring targeting element and activity element, the relative numbers of receptors of each type on the target cell, and the binding enhancement factor resulting from pre-binding of the chimeric protein to the receptor for the targeting element. In practice, mutations with a range of different strengths may be tested empirically using techniques known to one of ordinary skill in the art. FIG. 2 illustrates a non-limiting example of these processes. In A), a target cell expresses the Receptors for both the targeting element ($R_T$) and Receptors for the Activating Element ($R_A$). The Chimeric Activator first binds to the target cell surface via the targeting element (T). The resulting complex then undergoes two-dimensional diffusion in the cell membrane, and when the Activating Element (A) is near its receptor, binding will be driven by the high local concentration, in spite of the mutation in the Activating Element that reduces binding. Signal transduction results (lightning). In B), the chimeric activator does not bind to non-target cells because the intrinsic binding of the mutant Activator Element to its receptor is simply too low.

Aspects of the invention relate to creating mutations in the activity element, such that the mutated form of the activity element binds to its receptor with a reduced affinity relative to a wild-type form of the activity element. Accordingly, chimeric activators differ from fusion proteins in which an element with signaling activity may bind to more than one receptor type, and a mutation is introduced into this element to modulate the receptor type that is used (e.g., certain TNF chimeras, see also for example US20060263368). In contrast, Chimeric Activators of the invention differ from such distinct fusion proteins in that the signaling by a Chimeric Activator is directed through the receptor for which affinity has been reduced by the mutation in the activity element. As used herein, a "mutation" refers to a change in the nucleotide sequence encoding the activity element, relative to a wild-type form of the gene. A change in the nucleotide sequence may or may not lead to a change in the amino acid sequence, the three-dimensional structure of the protein, and/or the activity of the protein, relative to the wild-type form of the protein. In some embodiments a mutation may be a naturally occurring variant of the gene. In some embodiments a mutation may be a single amino acid substitution, two or more amino acid substitutions, one or more deletions, one or more insertions, or any combination of two or more thereof, in the protein sequence of the activity element. It will be understood that the selection of a suitable mutation in an activity element for the creation of a chimeric molecule will depend on multiple factors and in some embodiments will need to be determined empirically for different proteins.

It should be appreciated that variant activity elements of the invention may have a reduced binding affinity for their receptor(s) without a loss (or without a significant loss) of signal function (e.g., they substantially or completely retain their ability to promote signal transduction when bound to their receptor(s) even though their affinity for the receptor(s)

may be significantly reduced). It also should be appreciated that the reduced binding affinity of the variant activity element preferably does not result in a protein element that will not bind to its natural receptor(s), for example, due to steric hindrance or charge repulsion or other negative interaction between the variant activity element and its natural receptor(s), even when the targeting element binds to a target molecule on the same cell (thereby increasing the local concentration of the variant activity element in the vicinity of its natural receptor(s)).

In some embodiments, appropriate levels of reduced binding affinity can be obtained by introducing one or more mutations in charged or hydrophilic amino acids (or amino acids thought to be pointing outward) that have the effect of shortening the side chain of the amino acid(s). According to aspects of the invention, the charged or hydrophilic side chains are likely to be pointing outward and not into the middle of the protein. Reducing the size of the amino acid side chain(s) removes a contact, but does not create steric hindrance that would completely block binding or signaling. In some embodiments, mutants may be created in an activity element, and those that reduce but do not abolish binding may be selected (e.g., using one or more binding and/or activity assays known to one of skill in the art) and used to construct a Chimeric Activator.

According to aspects of the invention, variant activity elements of the invention can be identified or selected for any appropriate cell-surface receptor that is involved in a signaling activity that is useful for a particular application of interest.

For example, tumor necrosis factor receptors (TNFR) (e.g., CD120), or death receptors, are a family of cytokine receptors that bind to various tumor necrosis factors (TNF) (e.g., TNF-alpha). Exemplary tumor necrosis factor receptor family members include: CD120a (TNFRSF1A), CD120b (TNFRSF1B), Lymphotoxin beta receptor (LTBR, TNFRSF3), CD134 (TNFRSF4), CD40 (CD40, TNFRSF5), FAS (FAS, TNFRSF6), TNFRSF6B (TNFRSF6B), CD27 (CD27, TNFRSF7), CD30 (TNFRSF8), CD137 (TNFRSF9), TNFRSF10A (TNFRSF10A), TNFRSF10B, (TNFRSF10B), TNFRSF10C (TNFRSF10C), TNFRSF10D (TNFRSF10D), RANK (TNFRSF11A), Osteoprotegerin (TNFRSF11B), TNFRSF12A (TNFRSF12A), TNFRSF13B (TNFRSF13B), TNFRSF13C (TNFRSF13C), TNFRSF14 (TNFRSF14), Nerve growth factor receptor (NGFR, TNFRSF16), TNFRSF17 (TNFRSF17), TNFRSF18 (TNFRSF18), TNFRSF19 (TNFRSF19), TNFRSF21 (TNFRSF21), and TNFRSF25 (TNFRSF25). Several groups have demonstrated that human tumor cells can display between 100 and 5000 TNF receptor sites per cell (Rosenblum et al., 1991; Rosenblum et al., 1995). Thus, TNFRs represent an attractive target for inhibiting cancer cell growth and/or survival.

In some embodiments, the activity elements of the invention are ligands (agonists or antagonists) that bind to one or more tumor necrosis factor receptors known in the art or disclosed herein. In some embodiments, the activity elements of the invention are tumor necrosis factors or fragments thereof, such as TNF-alpha or TNF-beta (lymphotoxin). In some embodiments, the activity elements are selected from the TNF Ligand Family: LTA (TNF-α), TNF (TNF-a), TNFSF5 (CD40 Ligand), TNFSF6 (FasL), TNFSF7 (CD27 Ligand), TNFSF8 (CD30 Ligand), TNFSF9 (4-1BB Ligand), TNFSF10 (TRAIL), TNFSF14 (HVEM-L), TNFSF18, or fragments thereof. In some embodiments, the activity elements of the invention are tumor necrosis factors or fragments thereof, such as TNF-alpha or TNF-beta (lymphotoxin). In some embodiments, the activity elements of the invention are tumor necrosis factors with attenuated function. In some embodiments, the attenuated function is a reduced binding affinity for target receptors.

It should be appreciated that certain peptide elements may be used as targeting elements in some embodiments (e.g., a cytokine that can be used to target cells that express the cytokine receptor) and activity elements in different embodiments (e.g., the same cytokine could be used to activate cells that are targeted using a different targeting element in other embodiments). When a peptide is used as a targeting element, its natural affinity for the target molecule may be retained in the chimeric molecule. In some embodiments, the affinity of a natural peptide for a target molecule may be increased (e.g., by mutation) in order to improve its use as a targeting element. In certain embodiments, the binding affinity may be retained and/or increased but the function activity (e.g., signal transduction or enzymatic activity) may be decreased or removed (e.g., by mutation) if that particular function is not required or is undesirable. In contrast, if the same peptide is being used as an activity element in a different chimeric molecule, a variant form (e.g., a naturally occurring or engineered mutated form) may be used to reduce binding affinity of the activity element to non-target cells as described herein. Accordingly, one or more of the growth factors and/or cytokines described or listed herein as candidates for targeting elements also may be used as activity elements in other embodiments where they may be mutated to reduce their binding affinity for their receptor or substrate or target molecule.

One criterion that may be evaluated in selecting activity elements and targeting elements is the affinity of the activity element for its receptor, and the ratio of the affinity of the activity element for its receptor relative to the affinity of the targeting element for its receptor. In some embodiments mutated activity elements will be selected such that the activity element has a lower affinity for its receptor than the affinity of the targeting element for its receptor, thus allowing the targeting element to control which cells are bound by the chimeric molecule. In some embodiments the affinity ratio may be 1/2, 1/5, 1/10, 1/25, 1/50, 1/75, 1/100, 1/500, 1/1000, or an intermediate value, or a smaller value. Another set of criteria that may be evaluated in selecting activity elements and targeting elements include the on-rates, off-rates, and dissociation constants for the binding of the activity element to its receptor and the targeting element to its receptor. In some embodiments mutated activity elements will be selected wherein one or both of the following conditions are met: the on-rate of the activity element is lower than that of the targeting element, or if the off-rates are faster than the internalization rate, then the equilibrium constant ($K_{on}/K_{off}$) of the targeting element is higher than that of the activity element.

Another criterion that may be involved in selecting mutated activity elements is an evaluation of the activity level of the activity element alone, and the activity level of the activity element when it is linked to the targeting element. In some embodiments mutated activity elements may be selected that have reduced activity or are inactive alone, relative to a wildtype form of the protein, due to their reduced binding efficiency, but are active when linked to a targeting element, because the binding of a targeting element to its receptor at the cell surface increases the local concentration of the activity element in the vicinity of its receptor at the cell surface. It should be appreciated that appropriate activity levels for a given protein and a given mutation will need to be determined empirically. In some embodiments wherein an activity element is being targeted to a cancer cell in order to kill the cell, a mutated activity element will be selected such that the mutated activity element will not have sufficient activity to kill a cell when the activity element is alone, due to its reduced binding capacity for its receptor. When the activity element is linked to a targeting element, the increased local concentration of the activity element at the cell surface allows it to be active and bind to its receptor and kill the cell.

In some embodiments, targeting and activity elements are attached by a linker. The linker can be any amino acid sequence that allows the simultaneous binding of the activity element and the targeting element to their receptors on a given cell surface. Typically the linker is a non-folding, protease-resistant polypeptide segment that permits the targeting element and the activity element to bind to their cell-surface receptors, typically on the same cell surface, at the same time. Linkers may be of varied length (e.g., about 5, 10, 15, 20, 25, 30, 35, 40, 45, 50, 60, 70, 80, 90, 100 amino acids long or intermediate or longer lengths) and/or amino acid composition. Linkers may be flexible or rigid.

In some embodiments linker length will be optimized for maximizing binding efficiency of the activity element to the second binding site when the targeting element is bound to the first binding site. Optimal linker length for a given chimeric activator can be determined at least in part using models disclosed herein. In optimizing linker length, multiple factors will be considered including, but not limited to: the concentration of the first and second binding sites, the sizes of the activity element and targeting element, the minimum distance between the binding sites of the targeting element and the activity element, and the affinities of the activity element and the targeting element for the first and second binding sites. In some embodiments a linker length will be chosen that is at least equal to the minimum distance between the first and second binding sites on the cell surface. In other embodiments a linker length will be chosen that is at least twice the minimum distance between the first and second binding sites on the cell surface. In some embodiments a linker length will be chosen that is at most five-six times the minimum distance between the first and second binding sites on the cell surface. It will be understood that optimal linker length will vary depending on the specific proteins selected as activity elements and targeting elements. In some embodiments a protein which is blocked at the N- or C-terminus may be selected as an activity element or a targeting element. In these embodiments a linker may be added elsewhere on the protein.

In some embodiments, the linker length is chosen based in part on the known or surmised heights from the cell surface of the targeting element and activity element when each is bound to its receptor. For example, when EGF is bound to EGFR, its N- and C-termini are about 90 Angstroms from the cell surface, and when interferon alpha is bound to its receptor, its N- and C-termini are about 75 Angstroms from the cell surface, so that a linker of at least 15 Angstroms must be used.

The invention also provides methods for calculating an optimal linker length for a chimeric protein with two elements that simultaneously bind to a cell surface, based on the density of the receptors for each of the two elements on a cell surface and the difference in height from the cell surface of the termini of the two elements when bound to their receptors. The method optionally involves knowledge of the on-rates and off-rates of each element for its receptor. The method optionally involves calculating, as linker length is increased, the trade-off on the one hand between the increasing volume that can be occupied by one element when the other is bound to its receptor on a cell surface (which negatively impacts on a second binding event), and the increasing portion of cell surface area that may be sampled by one element when the other is bound to its receptor on that cell surface (which positively impacts on a second binding event). For many situations the density of a targeting element receptor is more than 10,000 per cell and the difference in height from the cell membrane of the bound elements is less than about 50 Angstroms, and in such situations a linker of about 25 to 70 amino acids is found to be optimal, with a linker length of about 30 to 40 amino acids often being more optimal. The linker should be flexible.

In many cases it is preferable to have both a targeting element and an activity element that engage their receptors through monomeric interactions. For example, in an interferon alpha-EGF Chimeric Activator, both the interferon alpha element and the EGF element are monomeric. This is in contrast to the activity elements TNF and TRAIL, which are trimeric, and to targeting elements consisting of antibodies, which are generally dimeric or have higher-order multivalent binding properties. One advantage of using targeting elements and activity elements that function as monomers is that it is easier to quantitatively predict their properties and thus to design specific molecules with desired features. It is also generally easier to predict the structure of the complex on the cell surface in which the targeting element and activity element are simultaneously bound. Examples of functionally monomeric activity elements include interferon alpha, interferon beta, IL-1, IL-2, IL-3, IL-4, IL-6, IL-11, IL-12, IL-13, IL-15, IL-18, erythropoietin, insulin, insulin-like growth factor, thrombopoietin, EGF, and CNTF. Examples of functionally monomeric targeting elements include single-chain Fv proteins and Fabs, as well as CD4, IL-1, IL-2, IL-3, IL-4, IL-6, IL-11, IL-12, IL-13, IL-15, IL-18, erythropoietin, insulin, insulin-like growth factor, thrombopoietin, EGF, and CNTF. Therefore, the invention provides Chimeric Activators that contain a monomerically functioning activity element and a monomerically functioning targeting element. More broadly, the invention provides proteins comprising two monomerically binding peptide moieties, optionally connected by a linker, such that both moieties can simultaneously bind to their receptors and/or target molecules on a single cell surface, in which at least one moiety signals through its receptor, and for which the signaling moiety contains a mutation relative to its naturally occurring form that reduces the binding to the receptor through which the signaling moiety signals. In some embodiments, a monomeric portion of a naturally multimeric targeting element and/or activity element may be used (e.g., by removing a multimerization domain). In these embodiments, the activity element also may include an additional mutation to reduce its affinity for its receptor as described herein.

In some embodiments, a chimeric protein of the invention may include a recombinant binding protein such as recombinant antibody instead of the activity element. The binding protein may be engineered to have very low affinity (relative to specific antibody binding affinity) for a target molecule that can transduce a signal (or result in another biological or cellular response) upon binding by the binding protein (e.g., low affinity antibody). Accordingly, aspects of the invention described in the context of a chimeric protein including a variant activity element also may be used in connection with an chimeric protein that includes a low affinity engineered binding protein instead. The same considerations for the targeting element and the optional linker apply.

As used herein, the term "binding" refers to a non-covalent or a covalent interaction, preferably non-covalent, that holds two molecules together. For example, two such molecules could be an enzyme and an inhibitor of that enzyme. Another example would be an enzyme and its substrate. A third example would be an antibody and an antigen. Non-covalent interactions include, but are not limited to, hydrogen bonding, ionic interactions among charged groups, van der Waals interactions, and hydrophobic interactions among non-polar groups. One or more of these interactions can mediate the binding of two molecules to each other. Binding may exhibit discriminatory properties such as specificity or selectivity. Binding affinities may range from mM to pM (e.g., micromolar or nanomolar binding affinities) depending on the concentration of the receptors and the activity of the activator elements.

The term "HIS-tag" refers to an affinity tag consisting of multiple consecutive histidine amino acids. Generally six (hexa-HIS) residues are used, or multiples thereof. His-tagged proteins have a high selective affinity for $Ni^+$ and a variety of other immobilized metal ions. Consequently a protein containing a His-tag generally can be selectively bound to a metal ion charged medium while other cellular proteins bind weakly or are washed out with binding or wash buffers. His-tags are small and therefore, tend to be less disruptive to the properties of the proteins on which they are attached.

The term "myc tag" refers to an epitope tag derived from myc protein, generally comprising the sequence amino acid SEQ ID NO: 17: EQKLISEEDL. A number of different antibodies are known to recognize the myc epitope tag, for example 9B11 and 9E10.

The term "RNA equivalent" refers to an RNA sequence corresponding to a DNA or amino acid sequence. Such equivalents may correspond directly to the original sequence (in the case of a protein the "coding sequence"), or may include additional sequence, such as untranslated regions and introns. In the case of an RNA equivalent for DNA the correspondence may be complementary to the DNA strand or anti-sense, allowing for the fact that in RNA "U" replaces "T" in the genetic code. DNA/RNA sequences of the sequence listing may be considered to follow this guidance.

Nucleic acids of the invention include isolated or recombinant nucleic acids comprising coding sequences for Chimeric Activators or components thereof described herein. The nucleic acids may be on vectors. The nucleic acids may be in host cells. It should be appreciated that the nucleic acids also may include regulatory sequences for transcription (e.g., promoters, activators, terminators, etc.) and translation (e.g., ribosome binding sequences, IRES elements, terminators, etc.) of the chimeric proteins in addition to sequences required for vector replication and/or selection and/or packaging in host cells (e.g., prokaryotic or eukaryotic host cells, including, but not limited to bacterial, mammalian, yeast, insect, and/or other host cells). Accordingly, aspects of the invention relate to recombinant vectors which include one or more nucleic acids of the invention (e.g., SEQ ID NOs: 1, 3, 5, 7, 9, 11, 13, and 15), as well as host cells containing the vectors or which are otherwise engineered to contain or express nucleic acids or polypeptides of the invention, and methods of making such vectors and host cells and their use in production' of polypeptides of the invention by recombinant or synthetic techniques. In some embodiments, Targeting and activity elements may be isolated (e.g. expressed and purified) independently and linked via a synthetic linker.

In some embodiments, the polynucleotides of the invention are joined to a vector (e.g., a cloning or expression vector). The vector may be, for example, a phage, plasmid, or viral vector. Viral vectors may be replication competent or replication defective. In the latter case, viral propagation generally will occur only in complementing host cells. The polynucleotides may be joined to a vector containing a selectable marker for propagation in a host. Introduction of the vector construct into the host cell can be effected by techniques known in the art which include, but are not limited to, calcium phosphate transfection, DEAE-dextran mediated transfection, cationic lipid-mediated transfection, electroporation, transduction, infection or other methods. Such methods are described in many standard laboratory manuals, such as Davis et al. (1986) Basic Methods In Molecular Biology.

The polypeptides of the invention or fragments thereof may be provided in substantially pure form, that is to say free, to a substantial extent, from other proteins. Thus, a polypeptide may be provided in a composition in which it is the predominant component present (i.e., it is present at a level of at least 50%; preferably at least 75%, at least 90%, or at least 95%; when determined on a weight/weight basis excluding solvents, carriers, or coupling agents).

Polypeptides of the invention can be recovered and purified from recombinant cell cultures or organisms by well-known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, Chimeric Activator proteins are expressed in and secreted from the yeast *Pichia pastoris*. In one embodiment, a combination of these methods is used. In another embodiment, high performance liquid chromatography is used. In a further embodiment, an antibody which specifically binds to a polypeptide of the invention can be used to deplete a sample comprising a polypeptide of the invention of the polypeptide or to purify the polypeptide. Techniques well-known in the art, may be used for refolding to regenerate native or active conformations of the polypeptides of the invention when the polypeptides have been denatured during isolation and or purification, should such be desired.

Polypeptides of the invention (and their corresponding DNA and RNA coding sequences) may comprise sequences, for example, epitope or affinity tags, that may aid in isolation or purification of the protein. However, they need not do so. For example, proteins of the invention (e.g., SEQ ID NOs: 2, 4, 6, 8, 10, 12, 14, or 16) may be purified through use of reagents that bind myc and/or HIS tags, but the invention also contemplates embodiments in which the proteins lack the myc and/or HIS tags, or which utilize different epitope or affinity tags.

Chimeric Activator nucleic acids and/or polypeptides may be screened, such as in high-throughput screening of a library of Chimeric Activators to select for a Chimeric Activator of the desired characteristics, or may be screened individually. For example, measurement of signal transduction in mammalian cells using Western blots that detect phosphorylation at specific sites may be used to screen for Chimeric Activators of a desired signal transduction activity.

Chimeric activators may be of various functions, e.g., having activity working against cancer, viral infection, and obesity. Diverse proteins can be used as activity elements and targeting elements. These proteins can be structurally varied, including monomers, trimers, and heterodimers of alpha helices and beta sheets. Some design considerations are illustrated in the Examples. Activity elements may be a non-toxic pro-drug that is activated in the target locale, for example, by cancer cells. It should be appreciated that many functions are compatible with the chimeric activators of the claimed invention. In some embodiments, the targeting element targets the activity element to a specific cell or cell type in order to kill a specific cell or cell type. In other embodiments the targeting element targets the activity element to a specific cell or cell type, for a purpose other than to kill the specific cell or cell type (e.g. to upregulate or downregulate one or more proteins or cellular properties such as cell growth, or proliferation).

Chimeric Activator nucleic acids and/or polypeptides may be used in gene therapy or in pharmaceutical compositions. Chimeric Activator nucleic acids and/or polypeptides may be used in treatment of a subject or patient, and may be used in combination with other therapies. Use of Chimeric Activator nucleic acids and/or polypeptides may be indicated by a diagnostic or theranostic, for example, a biopsy, for the appropriate presence of receptors for the Targeting and/or activity element.

Aspects of the invention relate to the use of chimeric activator proteins in the treatment of disorders. In some embodiments chimeric activator proteins are used to treat subjects who have cancer. As used herein, the term "subject" refers to a human or non-human mammal or animal. Non-human mammals include livestock animals, companion animals, laboratory animals, and non-human primates. Non-human subjects also specifically include, without limitation, chickens, horses, cows, pigs, goats, dogs, cats, guinea pigs, hamsters, mink, and rabbits. In some embodiments of the invention, a subject is a patient. As used herein, a "patient" refers to a subject who is under the care of a physician or other health care worker, including someone who has consulted with, received advice from or received a prescription or other recommendation from a physician or other health care worker. A patient is typically a subject having or at risk of having cancer. The term "treatment" or "treating" is intended to refer to prophylaxis, amelioration, prevention and/or cure of a condition (e.g., cancer). Treatment after a condition (e.g., cancer) that has started aims to reduce, ameliorate or altogether eliminate the condition, and/or its associated symptoms, or prevent it from becoming worse. Treatment of subjects before a condition (e.g., cancer) has started (i.e., prophylactic treatment) aims to reduce the risk of developing the condition and/or lessen its severity if the condition does develop. As used herein, the term "prevent" refers to the prophylactic treatment of a subject who is at risk of developing a condition (e.g., cancer) resulting in a decrease in the probability that the subject will develop the disorder, and to the inhibition of further development of an already established disorder.

As used herein, the term "cancer" refers to an uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject.

As used herein, the term "cancer" includes, but is not limited to, the following types of cancer: breast cancer (including carcinoma in situ), biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; mesothelioma, neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Non-limiting examples of precancerous conditions include dysplasia, premalignant lesions, adenomatous colon polyp, and carcinoma in-situ such as Ductal carcinoma in-situ (DCIS), etc. Other cancers that can be treated with methods of the invention will be known to those of ordinary skill in the art. In some embodiments of the invention, the cancer is melanoma. In certain embodiments the cancer is adenocarcinoma. In some embodiments the cancer is a solid tumor cancer.

Administration

Compositions of the invention may be administered in effective amounts. An effective amount is a dosage of the composition of the invention sufficient to provide a medically desirable result. An effective amount means that amount necessary to delay the onset of, inhibit the progression of or halt altogether the onset or progression of the particular condition (e.g., cancer) being treated. An effective amount may be an amount that reduces one or more signs or symptoms of the condition (e.g., cancer). When administered to a subject, effective amounts will depend, of course, on the particular condition being treated (e.g., the cancer), the severity of the condition, individual subject parameters including age, physical condition, size and weight, concurrent treatment, frequency of treatment, and the mode of administration. These factors are well known to those of ordinary skill in the art and can be addressed with no more than routine experimentation.

Actual dosage levels of active ingredients in the compositions of the invention can be varied to obtain an amount of the composition of the invention that is effective to achieve the desired therapeutic response for a particular subject, compositions, and mode of administration. The selected dosage level depends upon the activity of the particular composition, the route of administration, the severity of the condition being treated, the condition, and prior medical history of the subject being treated. However, it is within the skill of the art to start doses of the composition at levels lower than required to achieve the desired therapeutic effort and to gradually increase the dosage until the desired effect is achieved. In some embodiments, lower dosages would be required for combinations of multiple compositions than for single compositions.

It should be appreciated that an optimized dosage may be based, at least in part, on the residual non-specific toxicity of the activity element in a chimeric activator, the concentration of target molecules on the target cells, the binding affinity of the targeting element of the chimeric activator for the target molecules, and the length and flexibility of the linker. The amount of compound added should be sufficient to obtain a concentration of chimeric activator on the target cells that is sufficient to promote the desired response in the target cells. However, the amount should not be higher than necessary to avoid exposing non-target cells with levels of variant activity element that would be sufficient to activate the non-target cells. It should be appreciated that the optimal amount may be different for different chimeric activators (e.g., with different relative binding of targeting and activity elements, etc.).

The compositions of the invention, can be administered to a subject by any suitable route. For example, the compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention in the body such as, for example, in the brain, in the abdominal cavity, under the splenic capsule, or in the cornea.

Dosage forms for topical administration of a composition of this invention include powders, sprays, ointments, and inhalants as described herein. The composition is mixed under sterile conditions with a pharmaceutically acceptable carrier and any needed preservatives, buffers, or propellants that may be required.

Pharmaceutical compositions of the invention for parenteral injection comprise pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents that delay absorption, such as aluminum monostearate or gelatin.

In some cases, in order to prolong the effect of the composition, it is desirable to slow the absorption of the composition from subcutaneous or intramuscular injection. This result can be accomplished by the use of a liquid suspension of crystalline or amorphous materials with poor water solubility. The rate of absorption of the composition then depends upon its rate of dissolution, which, in turn, may depend upon crystal size and crystalline form. Alternatively, delayed absorption of a parenterally administered composition from is accomplished by dissolving or suspending the composition in an oil vehicle.

Injectable depot forms are made by forming microencapsule matrices of the composition in biodegradable polymers such a polylactide-polyglycolide. Depending upon the ratio of composition to polymer, and the nature of the particular polymer employed, the rate of composition release can be controlled. Examples of other biodegradable polymers include poly(orthoesters) and poly(anhydrides). Depot injectable formulations also are prepared by entrapping the drug in liposomes or microemulsions that are compatible with body tissue.

The injectable formulations can be sterilized, for example, by filtration through a bacterial- or viral-retaining filter, or by incorporating sterilizing agents in the form of sterile solid compositions, which can be dissolved or dispersed in sterile water or other sterile injectable medium just prior to use.

The invention provides methods for oral administration of a pharmaceutical composition of the invention. Oral solid dosage forms are described generally in Remington's Pharmaceutical Sciences, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). As is known in the art, liposomes generally are derived from phospholipids or other lipid substances. Liposomes are formed by mono- or multi-lamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p 33, et seq. Liposomal encapsulation may include liposomes that are derivatized with various polymers (e.g., U.S. Pat. No. 5,013,556). In general, the formulation includes a composition of the invention and inert ingredients which protect against degradation in the stomach and which permit release of the biologically active material in the intestine.

In such solid dosage forms, the composition is mixed with, or chemically modified to include, a least one inert, pharmaceutically acceptable excipient or carrier. The excipient or carrier preferably permits (a) inhibition of proteolysis, and (b) uptake into the blood stream from the stomach or intestine. In one embodiment, the excipient or carrier increases uptake of the composition of the invention, overall stability of the composition, and/or circulation time of the composition in the body. Excipients and carriers include, for example, sodium citrate, or dicalcium phosphate, and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVICEL®, (b) binders such as, for example, methylcellulose ethylcellulose, hydroxypropyhnethyl cellulose, carboxymethylcellulose, gums (e.g., alginates, acacia), gelatin, polyvinylpyrrolidone, and sucrose, (c) humectants, such as glycerol, (d) disintegrating agents, such as agar-agar, calcium carbonate, potato or tapioca starch, alginic acid, certain silicates, sodium carbonate, starch including the commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffin, (f) absorption accelerators, such as quaternary ammonium compounds and fatty acids including oleic acid, linoleic acid, and linolenic acid (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay, (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBOWAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT® Examples of embedding compositions that can be used include polymeric substances and waxes.

The composition of the invention also can be in microencapsulated form, if appropriate, with one or more of the above-mentioned excipients.

Liquid dosage forms for oral administration include pharmaceutically acceptable emulsions, solutions, suspensions, syrups, and elixirs. In addition to the composition of the invention, the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring, flavoring, and perfuming agents. Oral compositions can be formulated and further contain an edible product, such as a beverage.

Suspensions, in addition to the composition of the invention, can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Also contemplated herein is pulmonary delivery of the composition of the invention. The composition is delivered to the lungs of a mammal while inhaling, thereby promoting the traversal of the lung epithelial lining to the blood stream. See, Adjei et al., Pharmaceutical Research 7:565-569 (1990); Adjei et al., International Journal of Pharmaceutics 63:135-144 (1990) (leuprolide acetate); Braquet et al., Journal of Cardiovascular Pharmacology 13 (suppl.5): s.143-146 (1989)(endothelin-1); Hubbard et al., Annals of Internal Medicine 3:206-212 (1989) ($\alpha$1-antitrypsin); Smith et al., J. Clin. Invest. 84:1145-1146 (1989) ($\alpha$1-proteinase); Oswein et al., "Aerosolization of Proteins," Proceedings of Symposium on Respiratory Drug Delivery II, Keystone, Colo., March, 1990 (recombinant human growth hormone); Debs et al., The Journal of Immunology 140:3482-3488 (1988) (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOL® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of a composition of the invention. Typically, each formulation is specific to the type of device employed and can involve the use of an appropriate propellant material, in addition to diluents, adjuvants, and/or carriers useful in therapy.

The composition may be prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

In addition, the use of liposomes, microcapsules or microspheres, inclusion complexes, or other types of carriers is contemplated.

Formulations suitable for use with a nebulizer, either jet or ultrasonic, typically comprise a composition of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the composition of the invention suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the composition of the invention and also can include a bulking agent, such as lactose, sorbitol, sucrose, mannitol, trehalose, or xylitol, in amounts that facilitate dispersal of the powder from the device, e.g., 50 to 90% by weight of the formulation.

Nasal delivery of the composition of the invention also is contemplated. Nasal delivery allows the passage of the composition to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories that can be prepared by mixing the composition of the invention with suitable nonirritating excipients or carriers, such as cocoa butter, polyethylene glycol, or suppository wax, which are solid at room temperature, but liquid at body temperature, and therefore melt in the rectum or vaginal cavity and release the active compound.

The following examples are intended to be illustrative of certain embodiments and are non-limiting. Any of the linkers, activity elements, targeting elements or other components described herein may be combined independently with each other according to the teachings herein.

EXAMPLES

Example 1

An IFNα EGF Chimeric Activator

Figure 3:
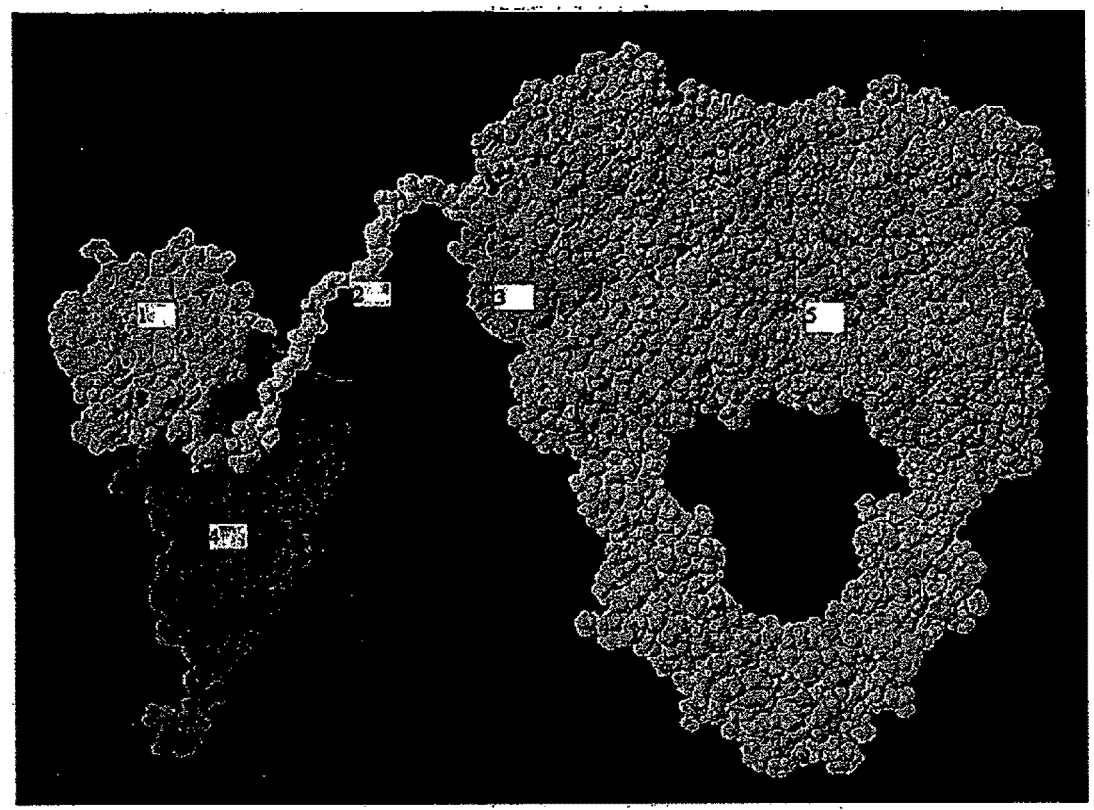
FIG. 3 shows a molecular model of an IFNα-EGF Chimeric Activator.

In some embodiments, a Chimeric Activator protein was constructed with the following protein components: a mutated version of interferon alpha (IFNα) as the Activating Element, a linker, and epidermal growth factor (EGF) as the targeting element. An embodiment of this chimeric protein is illustrated in FIG. 3. In FIG. 3, the IFNα activity element is shown in region (1), the $(Gly_4Ser)_7$ linker is shown in region (2), and the EGF targeting element is shown in region (3). In FIG. 3, the Chimeric Activator is bound to both IFNαR2 (shown as region (4)) and an active EGFR dimer (shown as region (5)). The figure shows only the extracellular domains of the receptors. The membrane-spanning domains would be at the bottom of the figure.

These elements were chosen based on the following considerations. The published structure of EGF receptor with a ligand (Garrett et al. (2002) Cell 110: 763-773) and a model of the IFNα structure (Quadt-Akabayov et al. (2006) Protein Sci. 15: 2656-2668) indicated that, in these receptor-ligand complexes, the EGF is about 90 Angstroms from the cell surface, and the IFNα is about 75 Angstroms from the cell surface, so that a linker of at least 15 Angstroms could bridge the two elements. A standard glycine-serine linker of 35 ($[Gly_4Ser_1]_7$) amino acids (Huston and Oppermann, 1993) was chosen. The structures also were useful for choosing whether to use the N-terminus or C-terminus of EGF and IFNα, and to design a linker of the right length. In addition, Piehler et al. (2000) J Biol Chem. 275: 40425-40433 published a precise characterization of the on-rates, off-rates, and $K_DS$ of a series of IFNα alanine-scanning mutants, so that a series of IFNα mutants with step-wise losses in binding affinity could be chosen (see Table 1 below). The on-rates and binding constants of EGF and IFNα are similar. The on-rates of both proteins are faster than diffusion-limited, because they are driven by charge-complementarity between these ligands and their receptors. It also was known that both EGF and IFNα could be expressed in *Pichia pastori* to give active proteins. Finally, IFNα and its PEGylated derivatives are used as drugs in the treatment of hepatitis B, hepatitis C, and certain forms of cancer. Side effects of IFNα treatment include flu-like symptoms, depression, and myelosuppression, which limit the dose and limit the therapeutic index. An engineered form of IFNα with reduced side effects may have the potential to replace IFNα for many diseases, and open up new treatments. A review of the literature on IFNα and cancer suggests that this protein 'almost works' for treatment of breast cancer, but is only somewhat too toxic to use—in other words, an improvement in therapeutic index of as little as 2- to 5-fold could dramatically extend the use of an IFNα-based compound to other types of cancer beyond melanoma and a few others. In contrast, other cell-killing elements such as *Pseudomonas* exotoxin are extremely toxic and might need an improvement in therapeutic index of >100-fold to become useful.

Although the considerations described in the preceding paragraph are helpful, it should be appreciated that compositions of the invention can be performed in the absence of such information as described herein.

Table 1 shows the binding characteristics of EGF and IFNα, and compares them with an anti-EGFR antibody that has been used in targeting studies.

TABLE 1

On-rates, off-rates, and dissociation constants of EGF,
wild-type and mutant IFNα, and an anti-EGFR antibody.

|  | $K_{on}$ | $K_{off}$ | $K_d$ | Reference |
|---|---|---|---|---|
| EGF | $2.5 \times 10^6$/M/sec |  |  | Bellot et al. (1990) J Cell Biol. 110: 491-502 |
| IFNa (wild-type) | $3.7 \times 10^6$/M/sec | $1 \times 10^{-2}$/sec | $3 \times 10^{-9}$ M | Piehler et al. (2000) J Biol Chem. 275: 40425-40433 |

TABLE 1-continued

On-rates, off-rates, and dissociation constants of EGF,
wild-type and mutant IFNα, and an anti-EGFR antibody.

| | $K_{on}$ | $K_{off}$ | $K_d$ | Reference |
|---|---|---|---|---|
| IFNa (K133A) | $0.7 \times 10^6$/M/sec | $1.8 \times 10^{-2}$/sec | $26 \times 10^{-9}$ M | Piehler et al. (2000) J Biol Chem. 275: 40425-40433 |
| IFNa (R144A) | $0.36 \times 10^6$/M/sec | $4 \times 10^{-2}$/sec | $120 \times 10^{-9}$ M | Piehler et al. (2000) J Biol Chem. 275: 40425-40433 |
| IFNa (R149A) | Too low to measure | | $538 \times 10^{-9}$ M | Piehler et al. (2000) J Biol Chem. 275: 40425-40433 |
| Anti-EGFRvIII (MR1-1) | $0.8 \times 10^6$ | $1.2 \times 10^{-3}$/sec | $1.5 \times 10^{-9}$ | Kuan et al. (2000) Int J Cancer. 88: 962-969 |

Based on these numbers, the binding of an IFNα-EGF Chimeric Activator should be driven by EGF. Note that the anti-EGFR antibody MR1-1 has an on-rate that is much lower than EGF or IFNα.

Based on these quantitative and structural considerations, four chimeric activators were constructed:
 1. IFNα (wild-type)—(Gly₄Ser)₇—EGF;
 2. IFNα (Lys133Ala)—(Gly₄Ser)₇—EGF;
 3. IFNα (Arg144Ala)—(Gly₄Ser)₇—EGF;
 4. IFNα (Arg149Ala)—(Gly₄Ser)₇—EGF.

These proteins were expressed as well as EGF alone and the corresponding individual IFNα mutants in the yeast *Pichia pastoris*. All of the proteins were epitope-tagged. The proteins were expressed at high levels. All of the Chimeric Activators showed EGF activity, based on their ability to stimulate phosphorylation of EGF receptor (data not shown).

Figure 4:
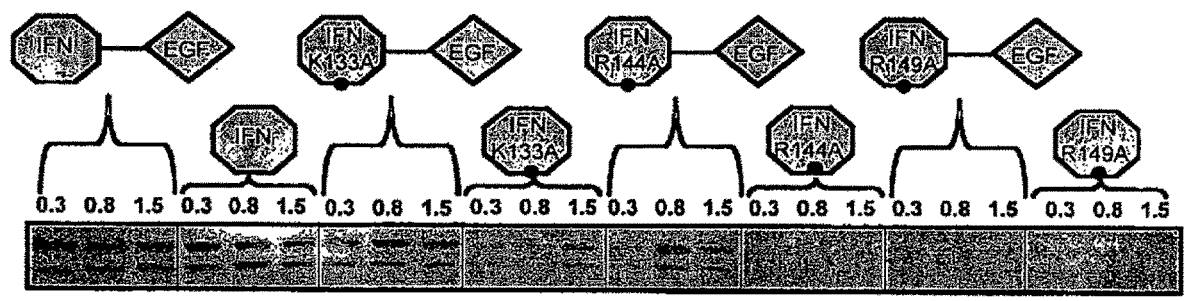
FIG. 4 illustrates an example of activation of IFNα signaling by chimeric activators.

The chimeric activators and the corresponding IFNα mutant proteins were compared for their ability to activate the IFNα receptor in HeLa cells, which naturally express EGFR and IFNαR. To measure IFNα signaling, STAT1 phosphorylation was detected by Western blotting; STAT1 tyrosine 701 is directly phosphorylated upon activation of IFNα receptor. The results shown in FIG. 4 indicate that an IFNα-EGF chimeric protein (without a mutation) and IFNα alone induce IFN signaling with about equal efficiency. The IFNα mutant proteins K133A, R144A, and R149A, which respectively are reduced by 10×, 40×, and 200× for IFNαR binding, show corresponding low levels of IFNα signaling. However, the Chimeric Activators with IFNα mutations fused to EGF show much higher levels of IFNα signaling than the corresponding IFNα mutants alone. In FIG. 4, chimeric activators (diamonds attached to octagons) and the corresponding IFNα protein without EGF (octagons) were added to cultures of HeLa cells at 0.3 nM, 0.8 nM, and 1.5 nM for 5 minutes. Cells were lysed, samples run on an SDS gel, blotted to nitrocellulose, and probed with an anti-phosphoSTAT1 antibody, which reflects IFNα signaling. Mutant IFNα proteins showed reduced signaling in a manner correlated with their reduced binding to IFNα receptor, while the IFNα-EGF mutant chimeric proteins showed much higher levels of signaling through STAT1. All lanes were loaded with an essentially equal amount of total cell protein.

Figure 5:
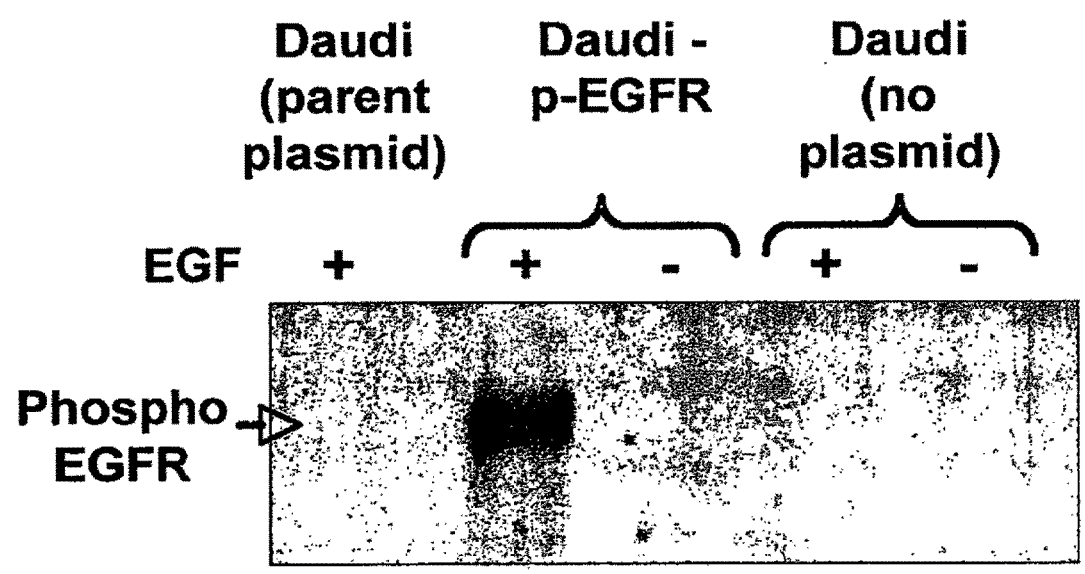
FIG. 5 illustrates an example of the targeting effect in a Daudi cell line constructed to express EGFR.
Figure 6:
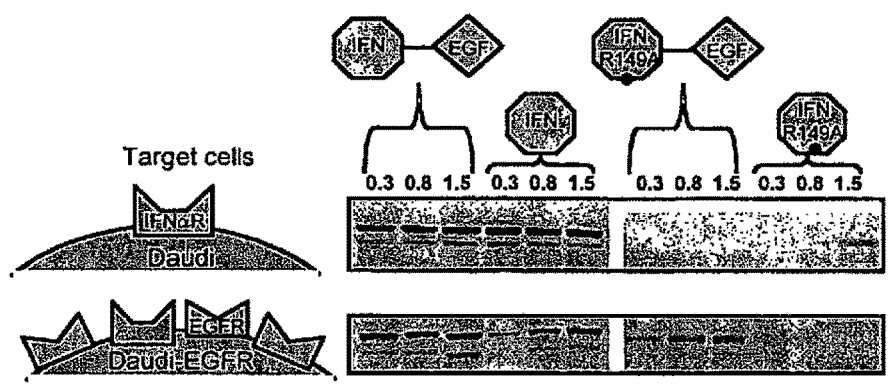
FIG. 6 illustrates an example of the dependence of Chimeric Activator function on the receptor for the targeting element.

To verify that the enhancement of IFNα signaling depended on binding to EGF receptor, a Daudi cell line was constructed to express EGFR and compared to the parent cell line for signaling induced by the chimeric activators. Daudi cells are a human Burkitt's lymphoma cell line whose proliferation and survival are inhibited by IFNα, but does not express EGFR. The results in FIG. 5 illustrate the experiments with the EGFR-expressing Daudi cell line. Cells were transfected with a plasmid that constitutively expresses EGFR. Parental cells, cells transfected with an empty plasmid vector, and EGFR-transfected cells were treated with EGF, and then phosphorylation of EGFR was detected by Western blotting. By comparing the activity of chimeric activators on cells with and without EGFR, the targeting effect can be demonstrated When the chimeric activators were tested on Daudi and Daudi-EGFR cells (see FIG. 6), the results clearly indicated that their function depended on the presence of the receptor for the targeting element, in this case EGF receptor. Daudi cells engineered to express EGFR (FIG. 5) and parental Daudi cells were treated with Chimeric Activators and mutant IFNα proteins, and STAT1 phosphorylation was measured by Western blot. The IFNα(R149A)-EGF protein specifically induced signal transduction in cells expressing EGFR. The EGFR-expressing cells correspond to therapeutic target cells, while the cells lacking EGFR correspond to 'side-effect' cells. On cells with only IFNα receptor, activation with the mutant IFNα Chimeric Activator protein was poor or undetectable. Specifically, the IFNα(R149A)-EGF protein stimulated STAT1 phosphorylation only in Daudi-EGFR cells, while the IFNα-EGF protein and IFNα alone were active in both cell lines and the IFNα mutant did not work in either cell line. Chimeric activators with the intermediate-strength mutations K133A and R144A showed intermediate reductions in signaling in Daudi cells, consistent with their predicted quantitative properties (data not shown).

Accordingly, this experiment was useful to compare cells with and without EGFR, the Daudi-EGFR cells correspond to tumor cells expressing EGFR or another target receptor, and the parental Daudi cells are analogous to "side-effect cells"—other cells in the body with little or no target receptor. It was estimated that the addition of the EGF targeting element enhances the specificity of IFNα signaling by at least 20-fold in this system.

Figure 7:
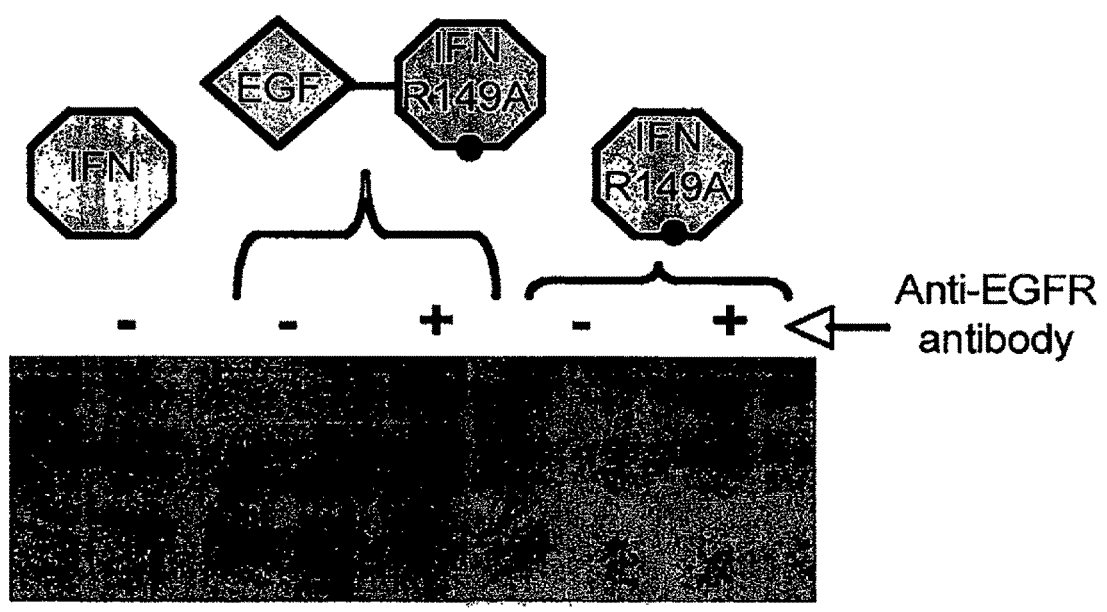
FIG. 7 illustrates an example of a Chimeric Activator function blocked by antibodies against the receptor for the targeting element.

As a final control, it was tested whether the signaling by IFNα(mutant)-EGFR chimeric activators could be inhibited by an antibody against the receptor for the targeting element. The data illustrated below indicates that this is the case. Pre-binding of an anti-EGFR antibody (monoclonal 528 (Calbiochem, La Jolla, Calif.)) blocks the signaling of the IFNα(R149A)-EGF chimeric activator in HeLa cells. This is illustrated in FIG. 7. HeLa cells were treated with either IFNα, IFNα(R149A)-EGF, or IFNα(R149A), and STAT1 signaling was measured by Western blot. The IFNα (R149A)-EGF protein was not able to induce interferon-mediated signal transduction when EGFR was blocked with a neutralizing anti-EGFR antibody Example 2

Chimeric Activator in an Animal Tumor Model

Chimeric Activators of Example 1 can be tested/screened for activity in animal tumor models. Pharmaceutical Product Development, Inc. (New York, N.Y.) can be used as a contract testing service to perform these tests. This type of experiment is standard in the development of anti-cancer drugs, and involves injection of human tumor cells into mice that have immune-suppressing mutations so that the tumor cells will not be rejected. In one form of the experiment, tumor cells are injected subcutaneously and then grow into a lump that can be measured with calipers. Once a tumor has reached a measurable size, treatment is started and the extent of tumor growth inhibition or shrinkage can be charted with time.

Using IFNα(R149A)-EGF as the test molecule, experiments can be performed in parallel sets of animals used paired tumor cell lines, one of which expresses the receptor for the targeting element, and one of which does not. The Daudi and Daudi-EGFR cells described above in Example 1 may be used. The host animal can be Nude mice, which are immunodeficient and therefore do not reject the tumor cells as foreign; use of Nude mice also means that the mice will not generate antibodies against the injected proteins.

PPD, Inc. offers testing for the Daudi models. They can also pre-test the engineered cell lines to verify that Daudi-EGFR cells can be used to generate tumors. PPD, Inc. can also perform mycoplasma testing on the tumor cell lines before they are used.

The treatment groups can be:
a. A chemotherapeutic agent as a positive control, such as cyclophosphamide for Daudi cells.
b. As a negative control, the appropriate IFNα mutant without the targeting element. About 10 micrograms of protein per dose will be given.
c. A low-dose treatment group with a Chimeric Activator with the molar equivalent of 2 micrograms of IFNα.
d. A high-dose treatment group with a Chimeric Activator with the molar equivalent of 10 micrograms of IFNα.

In some experiments, 8 to 10 mice may be used per group, for a total of about 80 mice for four dose groups in mice with the two different cell lines.

The amount of protein needed for these experiments may be less than 2 mgs for the entire experiment. The productivity of these *Pichia pastoris* lines is such that the culture supernatant contains about 1 mg/ml of the desired chimeric protein, and only small amounts of other proteins. The proteins, which contain a histidine tag, will be purified using a nickel column by standard techniques.

The protein can be administered by injection directly into subcutaneous tumors three times a week for three weeks. Tumor growth/shrinkage can be measured over a period of about a month. It can be tested whether appropriate signal transduction is activated in the tumor cells in vivo. Tumor biopsies can be frozen in liquid nitrogen, stored, and transferred back for Western blot analysis. The methods of Starostik et al. ((1998) Cancer Res. 58: 4552-4557) and Menon et al. ((2003) Am J Physiol Heart Circ Physiol. 284: H317-329) can be used to analyze the tissue for STAT1 phosphorylation.

Example 3

Tumor Necrosis Factor α (TNFα) as an Activity Element

To demonstrate the breadth of the Chimeric Activator concept, each element (activity element, a linker, and a targeting element) of the constructs of Example 1 can be replaced with an alternative component that is structurally different and/or has a different biological function. This is illustrated in this example and those that follow. These experiments may provide a molecule for testing in animals.

To demonstrate that IFNα can be replaced by other activators of signal transduction, a series of proteins with wild-type and mutant versions of Tumor Necrosis Factor (TNFα) can be constructed. Specifically, the following series of mutations defined by Zhang et al. ((1992) J Biol Chem. 267: 24069-24075) can be used:

| Mutation | Relative activity |
| --- | --- |
| Wild-type | 100% |
| N39Y | 30% |
| S147Y | 7% |
| Y87H | 0.6% |

TNF is a trimer with a completely different structure from IFNα. The structure of the TNF/TNF receptor complex has been solved. The N-terminus and C-terminus are not part of the interface with the receptor, so they are free for linker attachment. Specifically, a chimeric protein with the TNF at the N-terminus followed by the linker and the EGF can be made. As for the IFNα-EGF chimeric proteins described in Example 1 above, a series of proteins with various mutations, as well as control wild-type and mutant TNF proteins lacking EGF, can be made. The proteins can have a histidine tag to aid in purification.

Figure 8:
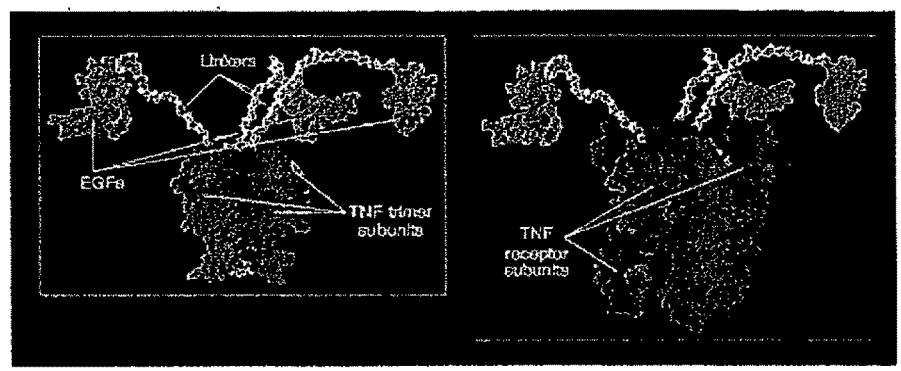
FIG. 8 shows an example of a TNF-EGF Chimeric Activator.

Molecular models of the TNF-linker-EGF Chimeric Activator by itself and in a complex with TNF receptor (see FIG. 8) illustrate how the TNF portion can still bind to its receptor when attached to the linker at EGF. Note that TNF has a trimeric structure, such that the chimeric protein is also a trimer in embodiments that include the trimerization domains.

TNF receptors are expressed on HeLa cells (Baglioni et al. (1985) J Biol Chem. 260: 13395-13397). TNF signaling will be measured using the same type of phosphorylation/ Western blot analysis as described above for IFNα. TNF signaling by a molecule such as TNF(S147Y)-EGF may depend on the EGF-EGF receptor interaction, which can be tested by showing that TNF signaling can be inhibited by an anti-EGF antibody, and that signaling by the corresponding TNF(S147Y) mutant protein without EGF is much weaker or undetectable.

Example 4

Antibody V Regions as a Targeting Element

EGFRde(2-7) is a mutant form of the EGF receptor with a deletion in the extracellular domain that creates a novel junction. (Exons 2 through 7 are deleted, creating a novel protein joint from exon 1 and exon 8.) This mutant form of the receptor is oncogenic and is naturally found on many tumor types, glioblastoma in particular. Since EGFRde(2-7) comes about by a mutation in cancer cells, it is not present at all in normal cells and thus it is an absolutely cancer-specific surface protein. The Pastan and Bigner groups have generated and characterized an antibody that recognizes the novel peptide junction. The antibody, termed MR1-1, has been affinity-optimized and has an on-rate that is only about 4-fold lower than the on-rate of EGF (Kuan et al. (2000) Int J Cancer. 88: 962-969; see Table 1 above).

Figure 9:
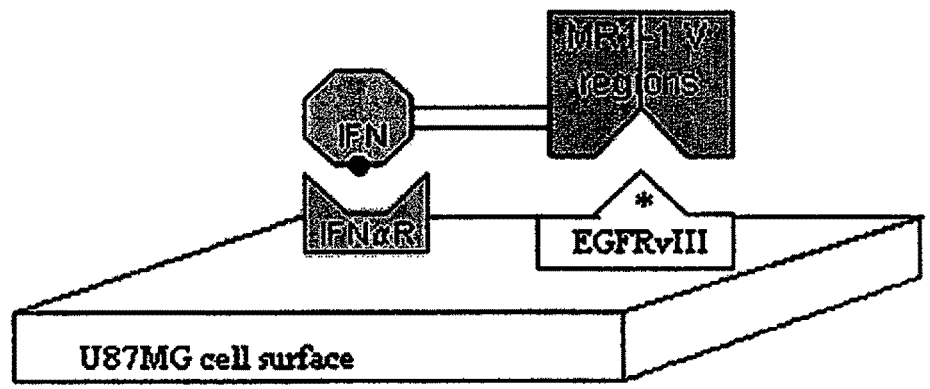
FIG. 9 illustrates the use of antibody V regions instead of EGF as a targeting element.

Experiments with an IFNα-MR1-1 Chimeric Activator can be performed. These may be analogous to the experiments performed above with the IFNα-EGF proteins, replacing the EGF targeting element with MR1-1 antibody V regions that recognize a tumor-specific EGFR variant, EGFRde(2-7). There are two publicly available cancer cell lines, U87MG and U87MG-EGFRde(2-7), where the second cell line was derived from the first by transfection with an expression construction for the EGFRde(2-7) mutant protein. The antibody MR1-1 only binds to the U87MG-EGFRde(2-7) line, allowing Chimeric Activators to be tested on both lines and determine whether a signaling event depends on the MR1-1 targeting element (see FIG. 9). In FIG. 9, EGFRvIII is a deleted form of EGF receptor that is only expressed on tumor cells. The deletion junction creates a novel amino acid sequence (*). MR1-1 is an antibody that recognizes this deletion junction, and does not recognize normal EGF receptor. A Chimeric Activator based on MR1-1 should be completely tumor-specific.

These paired cell lines have been extensively used and can be used in mouse tumor models. The U87MG nude mouse model is sensitive to IFNα (Iqbal Ahmed et al. (2001) Cancer Gene Ther. 8: 788-795). U87MG is derived from a human glioblastoma cell line.

Glioblastoma is one of the most difficult types of human cancer to treat, and many patients die within a year of diagnosis. Most glioblastoma tumor cells have the EGFRde (2-7) deletion, so an IFNα-MR1-1 Chimeric Activator should work in this type of patient. Because glioblastoma patients rarely respond to treatment and progress so quickly, it may be possible to detect responses to an IFNα-MR1-1 Chimeric Activator during the Phase I stage of clinical trials.

IFNα-MR1-1 Chimeric Activators can be constructed with wild-type IFNα and the same three mutants used above (K133A, R144A, and R149A). Specifically, the MR1-1 antibody V regions can be formatted as a "single-chain Fv" (scFv) to make molecules with IFNα at the N-terminus, a 35 amino acid glycine/serine linker, the heavy chain V region of MR1-1, a 15 amino acid glycine/serine linker, the light chain V region of MR1-1, and a histidine tag for purification. These chimeric proteins will be expressed in *Pichia pastoris* and purified as for the IFNα-EGF Chimeric Activators. *Pichia* is known to be a good system for expression of antibody V regions formatted as single-chain Fv molecules.

IFNα signaling can be measured using the STAT1 phosphorylation/Western blot assay described above. In order to test the impact of different linker lengths on the results, signaling can be measured using different linker lengths (e.g., the 35 amino acid glycine/serine linker can be doubled or tripled to create linkers of 70 and 105 amino acids between the IFNα and MR1-1 parts of the protein). It may also be necessary to introduce other amino acids besides glycine and serine, simply because the DNA sequences encoding the repeating peptide units may undergo genetic recombination because of the corresponding repeats in the DNA.

Example 5

A TNF-Leptin Chimeric Activator for Treatment of Obesity

Leptin is a hormone that is produced by adipocytes (fat cells) and also binds to receptors on adipocytes. At one time, leptin was thought to be a potential treatment for obesity, but further research indicated that in the vast majority of obese people, leptin is produced at high levels. In this example, leptin serves as a targeting element and its biological activity is not important to the function of the TNF-leptin Chimeric Activator.

One of the effects of TNF is to stimulate burning of lipids in adipocytes to help create fever. By targeting a mutated, less active TNF to adipocytes, fat burning and weight loss may result, as it does during illness, but without the other side effects of illness. Increased body temperature may still result from treatment with TNF-leptin, as this is a direct result of lipid oxidation in adipocytes. Leptin receptors are present on only a few other cell types in the body, such as cells in the hypothalamus that are thought to influence feeding and hunger. The action of TNF-leptin on these cells may be to inhibit feeding.

A series of TNF-leptin Chimeric Activators can be constructed using the same TNF mutations described above to bind to adipocytes (fat cells) and stimulate fat-burning for obesity treatment. Leptin would be the targeting element and a mutant form of TNF would be the activity element. The Chimeric Activators will have leptin at the C-terminus, since leptin has a disulfide bond that involves a cysteine at its very C-terminus, and a construct with the other orientation might have defective disulfide bond formation. The configuration of the leptin/leptin receptor complex is thought to be similar to the IFNα/IFNα receptor complex, and is favorable for the construction of a Chimeric Activator, as the C-terminus of TNF and the N-terminus of leptin are expected to be about the same distance away from the cell membrane.

To assay the activity of the TNF-leptin molecules, a stably transfected cell line that already expresses TNF receptor with an expression plasmid expressing a leptin receptor can be used. The activity of the TNF-leptin chimeric activators in the pair of cell lines with and without leptin receptor can be compared to demonstrate a specific requirement for the leptin receptor.

The biological activity of the TNF-leptin molecule can be tested in overweight mice. These would be normal mice that are fed a high-fat diet, which are a good representation of human obesity.

Example 6

An IFNα-CD4 Chimeric Activator for Treatment of HIV

CD4 is a surface protein on T cells that is the receptor for the HIV envelope protein, gp120. During later stages of HIV infection, the envelope protein appears on the cell surface and could be targeted by a Chimeric Activator with CD4 as a targeting element. The structures of the gp120/CD4 complex has been solved (Zhou et al. Nature 445: 732-737), and it indicates that the N-terminus of CD4 could be used as a junction for a protein fusion. The same IFNα mutations described above can be used. In some embodiments, only the N-terminual domain of CD4 is used, as depicted in the crystal structure, and IFNα-CD4 Chimeric Activators are constructed with a CD4 targeting element, targeting to the HIV envelope protein on HIV-infected cells.

To assay the activity of the IFNα-CD4 Chimeric Activator, a stably transfected Daudi cell line that already expresses IFNα receptor with an expression plasmid expressing gp120 can be used. The activity of the Chimeric Activators can be compared in the pair of cell lines with and without gp120, to demonstrate a specific requirement for the gp120.

The standard animal test system for HIV drugs is the SCID-hu mouse. In this system, an immunodeficient SCID mouse is populated with human immune cells, then infected with HIV.

Example 7

Evolution modulates the quantitative characteristics of protein interactions, and often uses combinations of weak interactions to achieve a particular specificity. How quantitative optimization might be used in the design of multidomain proteins was evaluated using a chimera containing epidermal growth factor (EGF) as a cell targeting element and interferon-alpha2a (IFNα2a) to initiate signal transduction. EGF and IFNα2a were connected via a linker that allows both ligands to bind to their receptors on a cell surface, then incorporated a series of mutations into the IFNα2a portion that progressively decrease both the on-rate and dissociation constant of the IFNα2a/IFNα receptor 2 (IFNAR2) interaction. Using this strategy, chimeric proteins were designed in which the activation of the IFNα receptor (IFNAR) in HeLa, A431 and engineered Daudi cells depends on the preysence of EGF receptor (EGFR) on the same cell. The mutant chimeric proteins also inhibit proliferation of IFNα-sensitive cells in an EGFR-dependent manner. These results provide insights into the quantitative requirements for specific binding to multi-subunit receptors, and illustrate the value of a quantitative approach in the design of synthetic-biological constructs.

Biological recognition events are often mediated by modular protein and nucleic acid segments that can be arbitrarily linked to give functional combinations. In the course of evolution, multidomain proteins have been repeatedly generated and constitute a large fraction of the proteins encoded by metazoan genomes. In the evolutionary improvement of such chimeras after a genetic rearrangement, an important but under-studied process is the quantitative optimization of the individual modules.

For many years, researchers have also constructed chimeric proteins with properties that derive from the parental modules. For example, one therapeutic approach has sought to use cell surface proteins as addresses to direct the delivery of specific molecules, such as toxins to tumor cells. In 1988, Pastan's group described a chimeric protein consisting of *Pseudomonas exotoxin* and IL-2, in which the IL-2 moiety directed the toxin to cells bearing IL-2 receptor (Lorberboum-Galski, H., FitzGerald, D., Chaudhary, V., Adhya, S., Pastan, I., (1998) *Proc Natl Acad Sci USA* 85(6), 1922-1926); they later described a *Pseudomonas exotoxin*-TGFα chimeric protein that binds to EGFR (Siegall, C. B., Xu, Y-H., Chaudhary, V. K., Adhya, S., Fitzgerald, D., Pastan, I., (1989) *FASEB J* 3(14), 2647-2652; Heimbrook, D. C., Stirdivant, S. M., Ahern, J. D., Balishin, N. L., Edwards, G. M., Defeo-Jones, D., FitzGerald, D. J., Pastan, I, Oliff. A., (1990) *Proc Natl Acad Sci USA* 87(12), 4697-4701; and Pai, L. H., Gallo, M. G., FitzGerald, D. J., Pastan, I., (1991) *Cancer Res* 51(11), 2808-2812), a hallmark of many tumors (Liu, T. F., Tatter, S. B., Willingham, M. C., Yang, M., Hu, J. J., Frankel, A. E., (2003) *Mol Cancer Ther* 2(8), 783-787). Similar strategies have been adapted by many groups (Kreitman, R. J., Pastan, I., (1999) *Handbook of Experimental Pharmacology: Novel Therapeutics from Modern Biotechnology*—Berlin, N.Y.: Springer-Verlag, p. 89-110; and Todhunter, D. A., Hall, W. A., Rustamzadeh, E., Shu, Y., Doumbia, S. O., Vallera, D. A., (2004) *Protein Eng Des Sel* 17(2), 157-164). A universal problem with this kind of approach is that when any targeted agent is administered to a patient, unwanted effects will occur as the drug travels through the body before reaching its target.

A strategy based on quantitative modulation of the signaling part of a targeted molecule was evaluated. Aspects of the invention build on the ideas of Adam and Delbrück (Adam, G., Delbruck, M., (1968) Reduction of dimensionality in biological diffusion processes—in: Rich A, Davidson N, editors, Structural chemistry and molecular biology, San Francisco: W. H. Freeman and Co. p. 198-215), who proposed that in biological systems, reaction rates are often enhanced by reduction of the dimension of a space in which diffusion occurs. According to aspects of the invention, but without wishing to be bound by theory, an initial rapid binding reaction to one cell surface protein could drive a second weak interaction on the same cell surface, because a cell surface is effectively two-dimensional. Accordingly, if the binding affinities of both the targeting agent and the activating ligand are tuned appropriately, a mutant chimeric protein can be developed that would show negligible activation on cells expressing just one of the relevant receptors. This strategy was tested using EGF as the targeting agent and IFNα2a as the toxin.

Figure 10:
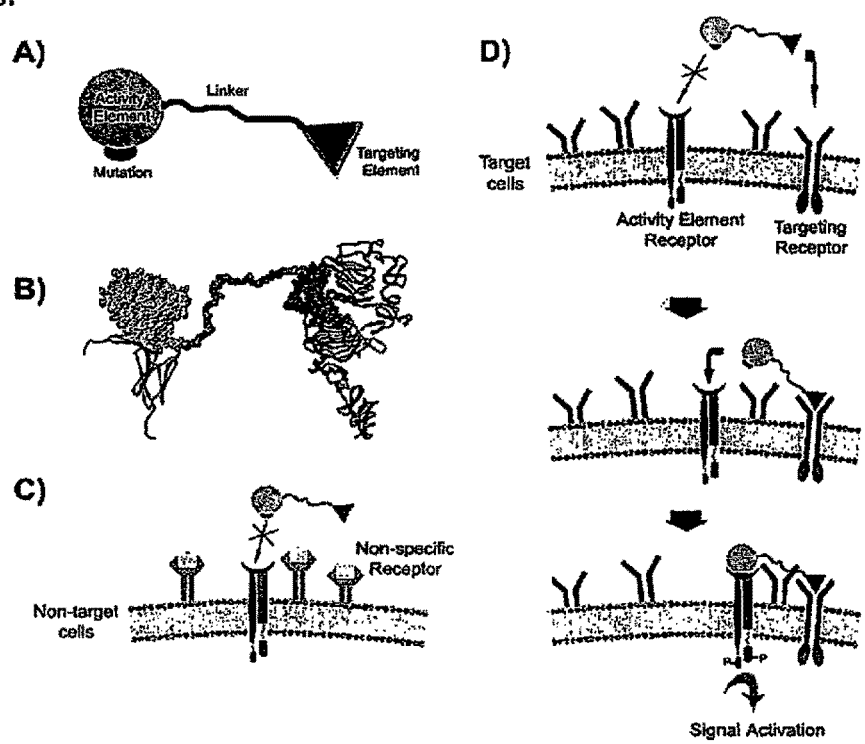
FIG. 10 illustrates non-limiting aspects of chimeric activation, 10A) illustrates a general structure of a chimeric activator, 10B) shows a molecular model of an IFNα2a-EGF chimeric activator (space-filling structure), 10C)-10D) illustrate a mechanism of specific binding of chimeric activators to target cells, in 10C) the chimeric activator binds poorly to non-target cells because the intrinsic binding affinity of the mutant activity element to its receptor is low, in contrast in 10D) the targeting element binds to receptors on a target cell at a high rate (after the targeting element complexes with its receptor, the activity element is in a high local concentration relative to its receptor, so that the activity element can then bind and stimulate signal transduction)

By combining quantitative information about protein binding kinetics and affinities with structural information about protein ligands and their cell-surface receptors, a new class of artificial proteins was developed that simultaneously bind to distinct cell surface receptors to create ligands with new cell-type specificities. In some embodiments, these proteins, termed "chimeric activators" have the following general structure: an activity element containing at least one mutation, a linker and a targeting element (FIG. 10A). The example of a general chimeric activator structure shown in FIG. 10A illustrates a 'targeting element' connected by a peptide linker to an 'activity element' with a mutation that reduces binding to the receptor for the activity element. According to aspects of the invention, this design takes advantage of multivalent interactions between ligands and cell-surfaces to ensure precise delivery of biological activities.

Experimental Procedures

Cell lines and culture conditions: Daudi, 293-T and HeLa cells were obtained from American type culture collection (Manassas, Va.). A431 cells were a gift from Thomas M. Roberts. A431, 293-T and HeLa cells were maintained in DMEM supplemented with 10% fetal bovine serum (FBS), 100 U ml$^{-1}$ penicillin and 100 μg ml$^{-1}$ streptomycin. Daudi cells were maintained in RPMI-1640 modified medium supplemented with 10% FBS, 100 U ml$^{-1}$ penicillin and 100 μg ml$^{-1}$ streptomycin. Stable Daudi-pLPCX-EGFR (Daudi-EGFR) and Daudi-pLPCX cell lines were generated by retroviral infection of Daudi cells following the protocol of Pear et al. available at the website of the Nolan Laboratory, Stanford University). Infected Daudi cells were first selected with puromycin (1.5 μg/mL) and then cells were isolated with Dynabeads Pan mouse IgG from Invitrogen (Maryland, USA) pre-coated with anti-EGFR mAb following the manufacturer instructions. The constructs pLPCX and pLPCX-EGFR were kindly provided by Joan S. Brugge, Harvard Medical School (Reginato, M. J., Mills, K. R., Paulus, J. K., Lynch, D. K., Sgroi, D. C., Debnath, J., Muthuswamy, S. K., Brugge, J. S., (2003) Nature Cell Biol 5(8), 733-740).

Antibodies: Anti-phospho-STAT1 (Tyr$^{701}$) rabbit pAb and anti-EGFR rabbit pAb were purchased from Cell Signaling Technology (Beverly, Mass.); PhosohoDetect™ anti-phospho-EGFR (Tyr$^{1068}$) rabbit pAb, anti-EGFR mouse mAb (EGFR.1), anti-EGFR mouse mAb (528) and anti-EGF rabbit pAb were purchased from Calbiochem (San Diego, Calif.); anti-actin mouse mAb was purchased from Chemicon International (Temecula, Calif.); anti-human IFNα/β R1-phycoerythrin mouse mAb was purchased from R&D systems (Minneapolis, Minn.); anti-EGFR R-Phycoerythrin-conjugated mouse mAb was purchased from BD Biosciences (San Jose, Calif.).

Gene synthesis, protein expression and purification: The coding sequence for the 'wild-type' chimeric activator, INFα-2a-(Gly$_4$-Ser)$_7$-EGF, consisting of the 165 amino acids of mature INFα-2a (GI:2781226), the 35 amino acid linker and the 53 amino acids of mature EGF (GI: 24987355), was synthesized by Top Gene Technologies (Quebec, Canada). This sequence was codon optimized for expression in *P. pastoris*. The sequence was sub-cloned (with XhoI and XbaI restriction sites) into the pPICZα A vector (Invitrogen), which includes the alcohol oxidase promoter and the α-factor leader sequence, a c-myc epitope tag and a $His_6$ tag for purification. The final sequence of the constructs was confirmed by DNA sequencing. Approximately 20 μg of the DNA construct were linearized with Pme I prior to transformation of *P. pastoris* X33 ($Mut^+$) and KM71H ($Mut^S$) cells. The electroporation method of the EasySelect™ *Pichia* expression kit (version H; Invitrogen) was used for transformation, and the transformants were plated on MD and MM agar plates to screen for methanol utilization (Mut) phenotype. Several $Mut^+$ and $Mut^S$ clones were put on plates with high zeocin concentrations (0.5 to 1 mg/ml) to select for clones with multiple integration events. A $Mut^S$ clone was selected for the protein expression. Transformants were grown and induced with methanol according to the instructions from Invitrogen. The INFα-2a-$(Gly_4$-$Ser)_7$-EGF chimeric activator was secreted into the medium and was purified with the ProBond™ purification system (for purification of polyhistidine-containing recombinant proteins, version K, Invitrogen). Purity was checked by Coomassie blue stain and by immunblotting against EGF. The final yield was approximately 1 mg per ml of cell culture.

Variants of INFα-2a-$(Gly_4$-$Ser)_7$-EGF were constructed containing the IFNα2a mutations K133A, R144A, and R149A by standard recombinant DNA techniques using the Quick-Change™ site-directed mutagenesis kit from Stratagene (Calif., USA). To produce control proteins, a set of Pichia expression vectors encoding IFNα2a wild-type and mutant proteins lacking the linker and EGF but containing the C-myc and $His_6$ tags were also constructed by analogous techniques. The correctness of the constructs was confirmed by DNA sequencing. The transformation, expression and purification of the different constructs were performed as described above.

Cell Stimulation, protein extraction, immunoblotting and immunoprecipitation: A431 and HeLa cells were seeded in 60 mm plates, Daudi and Daudi-EGFR were seeded in 50 mL bottles. Once they reached confluence the growth medium was replaced with fresh DMEM without FBS or antibiotics for 3 h (to reduce background signal from the serum).

EGFR stimulation: Cells were stimulated with human recombinant EGF from *E. coli* (Cell Signaling Technology), the chimeric activators, and Interferon-α A (Calbiochem) or vehicle (as negative controls) for 5 min at 37° C. and 5% $CO_2$. Stimulations were terminated by washing the cells once with ice-cold phosphate-buffered saline, and cells were lysed in NP40 lysis buffer (20 mM Tris-HCl at pH 7.5, 150 mM NaCl, 1% NP-40, 25 mM NaF, 10 mM β-glycerophosphate, 250 μM $Na_3VO_4$ supplemented with protease inhibitor cocktail tablets (Roche)). Cells were solubilized for 15 min at 4° C. in lysis buffer follow by centrifugation at 15,000 g for 15 min at 4° C., the detergent extracts (supernatant) were then subjected to immunoprecipitation. Lysates were incubated with 1 μg of anti-EGFR (EGFR.1) mouse monoclonal antibody overnight at 4° C. EGFR was immunoprecipitated with a mixture of Protein A and G-Sepharose beads (Amersham Bioscience) for 1 h. at 4° C. Beads were washed with NP-40 lysis buffer and boiled in SDS sample buffer. Proteins were resolved on 8% SDS-polyacrylamide, transferred to nitrocellulose, and detected by immunoblotting using the anti-phosphoEGFR(Tyr1068) antiserum.

STAT1 stimulation: As described above cells were stimulated with the chimeric activators, the IFNα-only counterparts, Interferon-α A, or EGF or vehicle (as negative controls) for 30 min at 37° C. and 5% $CO_2$. Stimulations were terminated by washing the cells once with ice-cold phosphate-buffered saline, and lysed in RIPA buffer (150 mM NaCl, 1% Deoxycholate, 10 mM Tris-HCL at pH 7.2, 0.1% SDS, 1.0% Triton X-100, 5 mM EDTA, 25 mM NaF, 10 mM β-glycerophosphate, 250 μM $Na_3VO_4$ supplemented with protease inhibitor cocktail tablets (Roche)). Proteins were resolved on 10% SDS-polyacrylamide, transferred to nitrocellulose, and detected by immunoblotting with anti-phosphoSTAT1(pTyr701) antiserum.

Neutralization of EGF receptor and STAT1 stimulation: HeLa cells were seeded as previously described. Once they reach confluence the medium was changed for fresh DMEM and cells were incubated with anti-EGFR mouse mAb 528. After 2 h treatment cells were tested for STAT1 stimulation as described above.

Anti proliferative assay: The anti-proliferative activity of IFNα-2a-linker-EGF chimeras, corresponding IFNα2a proteins, and commercial IFNα A on Daudi and Daudi-EGFR cell lines was assayed as follows. Proteins that had been previously filtered thorough a 0.2 μm PDVF filter unit (Millipore, Ireland) and then quantitated were serially diluted. Twenty serial dilutions were prepared in flat-bottomed 96-well plates for each tested protein. Daudi and Daudi-EGFR cells grown in RPMI-1680 medium were added (3×$10^4$ cells in 100 μL) to each well and were grown for an additional 60 h. in the presence of the different proteins. The number of living cells was then determined using a cell staining kit (Cell proliferation reagent WST-1, Roche) based on the colorimetric detection of the cleavage of the tetrazolium salt WST-1 into formazan. The WST-1 reaction solution was added according to the manufacturer's recommendation for a period of 4 h, after which the absorbance at 450 nm and 650 nm (reference wavelength) was recorded in an ELISA reader (Victor V, PerkinElmer).

Quantitative rationale for design of chimeric activators: The design of chimeric activators with a desired cell specificity requires an understanding of the on-rates, off-rates, and equilibrium constants of each of the receptor-binding elements. An important aspect of ligand-receptor interactions is that $k_{on}$ is primarily limited by diffusion. The off-rate for ligand-receptor interactions is often slower than the process of receptor-mediated endocytosis, and in such cases $k_{off}$ is not relevant to signaling. As a result, the binding of a chimeric protein composed of a targeting element and an activity element might not be significantly influenced by the supposed targeting element. For example, EGF and IFNα2a both have similar on-rates (Table 2) (French, A. R., Tadaki, D. K., Niyogi, S. K., Lauffenburger, D. A., (1995) *J Biol Chem* 270(9), 4334-4340; and Piehler, J., Roisman, L. C., Schreiber, G., (2000) *J Biol Chem* 275(51), 40425-40433), so that fusion of EGF to IFNα2a may have very little effect on the binding of the latter to its receptor.

TABLE 2

On-rates, off-rates, and dissociation constants of EGF, and wild-type and mutant IFNα2.

| | $K_{on}$ (1/M · seg) | $K_{off}$ (1/sec) | $K_d$ (M) | Chimeric Activators (CA) |
|---|---|---|---|---|
| EGF | $1 \times 10^6$ | $2.6 \times 10^{-3}$ | $2.6 \times 10^{-9}$ | |
| IFNα-2a (wild-type) | $3.7 \times 10^6$ | $1 \times 10^{-2}$ | $3 \times 10^{-9}$ | IFNα-2a (wild-type) - (Gly$_4$Ser)$_7$ - EGF (CA-wt) |
| IFNα-2a (K133A) | $0.7 \times 10^6$ | $1.8 \times 10^{-2}$ | $26 \times 10^{-9}$ | IFNα-2a (K133A) - (Gly$_4$Ser)$_7$ - EGF(CA-K133A) |
| IFNα-2a (R144A) | $0.36 \times 10^6$ | $4 \times 10^{-2}$ | $120 \times 10^{-9}$ | IFNα-2a (R144A) - (Gly$_4$Ser)$_7$ - EGF (CA-R144A) |
| IFNα-2a (R149A) | Too low to measure | | $538 \times 10^{-9}$ | IFNα-2a (R149A) - (Gly$_4$Ser)$_7$ - EGF (CA-R149A) |

In some embodiments, but without wishing to be bound by theory, for a chimeric activator to have a cell specificity driven by the targeting element, one or both of the following conditions should be met: the on-rate of the activity element should be lower than that of the targeting element, or if the off rates are faster than the internalization rate, then the equilibrium constant ($K_{on}/K_{off}$) of the targeting element should be higher than that of the activity element. Once such a chimeric activator binds to a cell surface via the receptor for the targeting element, binding of the activity element to its receptor should in principle be driven by its high local concentration relative to its receptor (FIGS. 10C and D).

A rationally designed set of chimeric activators were constructed, consisting of wild-type and mutant forms of IFNα2a as the activating element, and EGF as the targeting element (FIG. 10A). A choice of these elements may be based on the following considerations: 1) the three-dimensional structures of the EGF/EGFR and the IFNα2a/IFNAR2 complexes have been solved or modeled (Ogiso, H., Ishitani, R., Nureki, O., Fukai, S., Yamanaka, M., Kim, J. H., Saito, K., Sakamoto, A., Inoue, M., Shirouzu, M., Yokoyama, S., (2002) *Cell* 110(6), 775-787; Garrett, T. P., McKern, N. M., Lou, M., Elleman, T. C., Adams, T. E., Lovrecz, G. O., Zhu, H. J., Walker, F., Frenkel, M. J., Hoyne, P. A., Jorissen, R. N., Nice, E. C., Burgess, A. W., Ward, C. W., (2002) *Cell* 110(6), 763-773; and Roisman, L. C., Piehler, J., Trosset, J-Y., Scheraga, H. A., Schreiber, G., (2001) *Proc Natl Acad Sci USA* 98(23), 13231-13236), allowing appropriate positions to be chosen for linking and to design a linker of the right length; 2) a precise characterization of the on-rates, off-rates, and $K_D$s of a series of IFNα alanine-scanning mutants was previously reported (Pithier, J., Roisman, L. C., Schreiber, G., (2000) *J Biol Chem* 275(51), 40425-40433), so that a series of IFNα2a mutants could be chosen with step-wise reductions in on-rates and affinity (Table 2); and 3) the on-rates and binding constants of wild-type EGF and IFNα are similar, so that the effect of mutations should be significant. The on-rates of both proteins are thought to be faster than diffusion-limited, because they are driven by charge-complementarity between these ligands and their receptors (Piehler, J., Roisman, L. C., Schreiber, G., (2000) *J Biol Chem* 275(51), 40425-40433; and Piehler, J., Schreiber, G., (1999) *J Mol Biol* 289(1), 57-67). Another consideration was that the molecules described here could serve as a proof-of-concept for a protein drug, and that targeting might improve the therapeutic index of a toxic molecule only by a limited amount. Thus, the fact that IFNα already has a preferential activity against abnormal cells such as cancer cells and virus-infected cells made it an attractive candidate (Platanias, L. C., (2005) *Nat Rev Immunol* 5(5), 375-386).

For the chimeric activator concept to work, the targeting element and activation element must be able to bind simultaneously to their respective receptors. The published structure of EGFR with a ligand and a model of the IFNα2a structure indicate that in these receptor-ligand complexes, the EGF is about 90 Å from the cell surface, and the IFNα2a is about 50 Å from the cell surface, so that a linker of at least 40 Å is needed to bridge the two elements. A standard glycine-serine linker of 35 amino acids ([Gly$_4$Ser]$_7$ was selected with a length of roughly 120 Å; FIG. 10B (Huston, J. S., Tai, M. S., McCartney, J., Keck, P., Oppermann, H., (1993) *Cell Biophys* 22(1-3), 189-224). Four chimeric activators were constructed (Table 2). These consist of wild-type or mutant IFNα2a at the N-terminus, followed by the 35-amino acid linker, EGF, a myc epitope tag, and a (His)$_6$ purification tag at the C-terminus. The IFNα2a mutations used were K133A, R144A, and R149A, which allow the protein to fold correctly but cause stepwise reductions in the on-rate and equilibrium binding of IFNα2a for its receptor (Table 2) (Piehler, J., Roisman, L. C., Schreiber, G., (2000) *J Biol Chem* 275(51), 40425-40433). The chimeric activators carrying wild-type INFα2a and these mutant forms were termed CA-wt, CA-K133A, CA-R144A and CA-R149A, respectively. FIG. 10B shows a molecular model of an IFNα2a-EGF chimeric activator (space-filling structure), showing how the IFNα2a and EGF components can simultaneously interact with their receptors (ribbons). Models for EGF/EGFR complex (Ogino, H., Ishitani, R., Nureki, O., Fukai, S., Yamanaka, M., Kim, J. H., Saito, K., Sakamoto, A., Inoue, M., Shirouzu, M., Yokoyama, S., (2002) *Cell* 110(6), 775-787; and Garrett, T. P., McKern, N. M., Lou, M., Elleman, T. C., Adams, T. E., Lovrecz, G. O., Zhu, H. J., Walker, F., Frenkel, M. J., Hoyne, P. A., Jorissen, R. N., Nice, E. C., Burgess, A. W., Ward, C. W., (2002) *Cell* 110(6), 763-773), and the IFNα2a/IFNAR2 complex (Roisman, L. C., Piehler, J., Trosset, J-Y., Scheraga, H. A., Schreiber, G., (2001) *Proc Natl Acad Sci USA* 98(23), 13231-13236; Quadt-Akabayov, S. R., Chill, J. H., Levy, R., Kessler, N., Anglister, J., (2006) *Protein Sci* 15(11), 2656-2668), are shown with the C-termini of the receptor extracellular domains at the bottom. In each case, these C-termini are followed by the membrane-spanning segment of the receptor.

These chimeric activators and the corresponding individual IFNα2a and IFNα2a mutants were expressed in the yeast *Pichia pastoris* according to published methods, and purified them from culture supernatant (Clare, J. J., Romanos, M. A., Rayment, F. B., Rowedder, J. E., Smith, M. A., Payne, M. M., Sreekrishna, K., Henwood, C. A. (1991) *Gene* 105(2), 205-212; and Garcia, J. N., Aguiar, J. A., Gill, M., Alvarez, A., Morales, J., Ferrero, J., Gonzalez, B., Padron, G., Menendez, A., (1995) *Biotecnologia Aplicada* 12, 152-155). All proteins were epitope-tagged and His$_6$-tagged for further detection and purification. The proteins were expressed at high levels and recovered at high purity (see Experimental Procedures).

Figure 11:
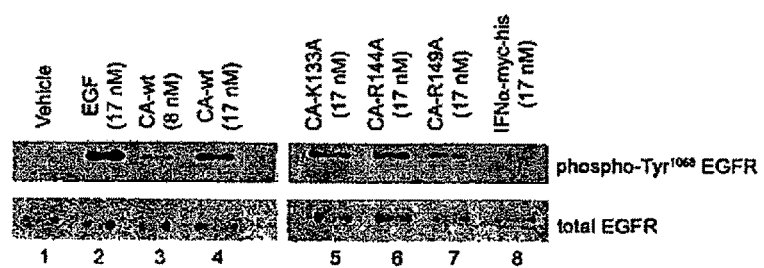
FIG. 11 illustrates an embodiment of EGFR activation upon treatment with IFNα2a-EGF chimeric activators.
Figure 12:
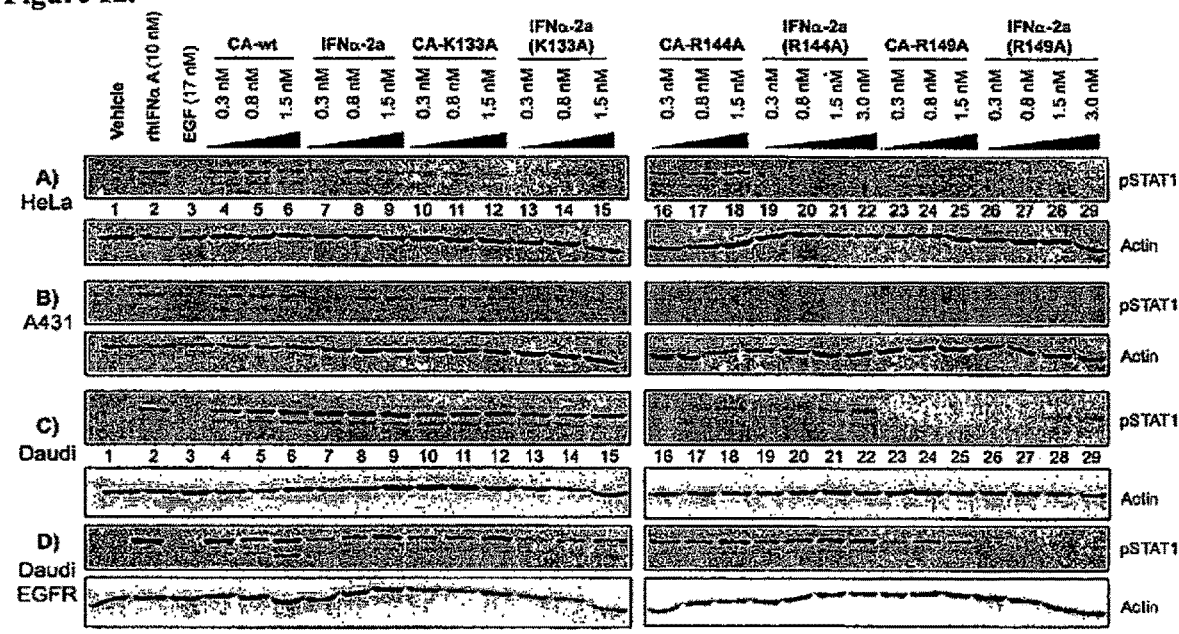
FIG. 12 illustrates an example of STAT1 activation upon treatment with IFNα2a-EGF chimeric activators.

Functionality of parts within chimeric activators: The biological activity of the targeting element, EGF, was verified in the chimeric activators by testing its ability to stimulate phosphorylation of tyrosine-1068 in EGFR. Activation of EGFR was evaluated in HeLa cells by treating them with the four chimeric proteins, a commercial recombinant EGF as a positive control, and IFNα2a tagged with c-myc and His$_6$ as a negative control. FIG. 11 illustrates the induction of phosphorylation of the EGFR by the different chimeric proteins as well for the rEGF control (lanes 2 to 7). HeLa cells were stimulated for 5 minutes with vehicle (PBS; lane 1) EGF (lane 2), chimeric activators containing wild-type EGF linked to wild-type or mutant IFNα2a (lanes 3-7), or wild-type IFNα2a protein expressed from *Pichia pastoris* in the same manner as the chimeric activators (lane 8). EGF receptor immunoprecipitated from stimulated HeLa cell lysates were separated by SDS-PAGE, then immunoblotted for Tyr1068-phosphorylated EGF receptor (top) or total EGF receptor (bottom). Cells treated only with PBS (vehicle) or with tagged IFNα do not show detectable activity (lanes 1 and 8). To test the activity of the IFNα portion of the chimeric activators, the phosphorylation of STAT1 tyrosine 701 (a consequence of IFN-α receptor activation; FIG. 12) was examined by Western blot. These experiments demonstrated that the EGF and IFNα2a components of the chimeric proteins were both active and that the mutations K133A, R144A, and R149A reduced the activity of the tagged IFNα2a to a degree similar to the reductions previously reported (Piehler, J., Roisman, L. C., Schreiber, G., (2000) *J Biol Chem* 275(51), 40425-40433).

Activity of IFNα2a-EGF chimeric activators depends on EGFR: It was tested whether the IFNα2a-EGF chimeric proteins could signal through IFNAR in an EGFR-dependent manner by comparing their activity with the activity of the corresponding IFNα2a (mutant) protein in cells expressing both EGFR and IFNAR. Two different epithelial cell lines were used with varying levels of EGFR expression: A431 cells, which show high expression of EGFR (~2×10$^6$ EGFR/cell), and HeLa cells, which show moderate expression of EGFR (2×10$^4$ EGFR/cell) (Masui, H., Kawamoto, T., Sato, J. D., Wolf, B., Sato, G., Mendelsohn, J., (1984) *Cancer Res* 44(3), 1002-1007). In FIG. 12, starved HeLa (A), A431 (B), Daudi (C), or Daudi-EGFR (D) cells were incubated for 30 minutes with PBS (vehicle), commercial IFNα A, EGF, IFNα/EGF chimeric activator proteins containing wild-type or mutant IFNα-2a (CAwt CAK133A, CAR144A, or CAR149A), or the corresponding wild-type or mutant IFNα2a proteins produced from *Pichia*. Lysates were prepared and immunoblots performed probing with an anti-STAT1(pTyr701) antibody, and with an anti-actin antibody as a loading control (in some examples, similar immunoblots were prepared in which lanes were scanned with a densitometer and the phospho-STAT1 signal normalized to the actin signal). HeLa, A431, and Daudi-EGFR cells express both EGFR and IFNAR, while Daudi cells express only IFNAR. Quantification by FACs analysis confirmed the expression levels of EGFR and IFNAR. The results indicated that an IFNα2a-EGF chimeric activator (without a mutation) and IFNα2a alone induced interferon signaling with about equal efficiency (FIGS. 12A and B, lanes 4-9), and that the IFNα2a mutant proteins K133A, R144A, and R149A, which respectively are reduced by 10×, 40×, and 200× for IFNAR binding (Table 1), show correspondingly low levels of IFNα signaling (FIGS. 12A and B, lanes 13-15, 19-22 and 26-29).

The chimeric activators with EGF fused to the mutant IFNα2a showed higher levels of IFNα signaling than the corresponding IFNα2a mutants alone, however. For example, in HeLa and A431 cells pSTAT1 was activated when cells were treated with CAR44A and CAR9A (FIGS. 12A and B, lanes 16-18 and 23-25) but not when the cells are treated with the corresponding IFNα2a mutants, even at higher concentrations (FIGS. 12A and B, lanes 22 and 29). No synergistic effect was seen when cells were treated with a combination EGF and any of the various IFNα2a mutants (data not shown).

As a second way to test whether the enhancement of IFNα signaling depends on binding to EGFR, EGFR was introduced into the Daudi cell line, which does not normally express this receptor and compared IFNα signaling in this engineered line to that seen in the parent cell line. The Daudi cell line is derived from a human Burkitt's lymphoma cell, and its proliferation and survival are inhibited by IFNα (Evinger, M., Pestka, S., (1981) *Methods in Enzymology* 79(Pt B), 362-368). The function of the chimeric activators on Daudi and Daudi-EGFR cells clearly depended on the presence of the receptor for the targeting element (FIGS. 12C and D). The CAR149A protein stimulated STAT1 phosphorylation only in Daudi-EGFR cells (FIG. 12D, lanes 23-25) and not in the Daudi parental cell line (FIG. 12C, lanes 26-29). The CAwt and IFNα2a proteins were active in both cell lines, as expected, whereas the IFNα2aR149A mutant showed only slight activity at high concentrations. Chimeric activators containing the intermediate-strength mutations CAK133A and CAR144A gave intermediate levels of signaling in Daudi cells, consistent with their predicted properties, and showed quantitative enhancements in signaling relative to IFNα2aK133A and IFNα2aR144A in Daudi-EGFR cells (FIG. 12D, lanes 10-22).

The activities of the chimeric activators differed on the various cell lines (FIG. 12). Without wishing to be bound by theory, these cell-type differences may be due to differences at the level of receptor expression, although the HeLa, Daudi, and A431 cell lines have different tissue origins and oncogenic mutations, so that any comparison of results between these lines can only be suggestive. Daudi cells have 10-20 times more IFNAR molecules at the cell surface than do HeLa and A431 cells, which may explain the greater level of IFNAR activation in Daudi cells, for example in response to CAR144A and IFNα2a(R144A).

Figure 13:
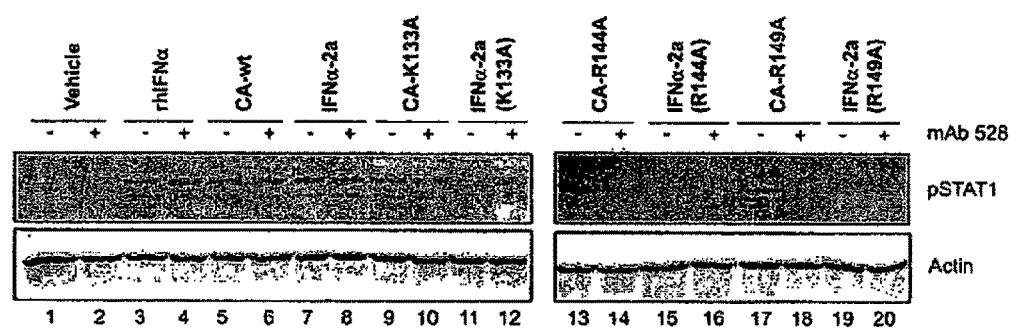
FIG. 13 illustrates an example of EGFR neutralization.

As an additional control, it was tested whether signaling by IFNα2a(mutant)-EGF chimeric activators could be inhibited by an antibody against the receptor for the targeting element (FIG. 13). In FIG. 13, HeLa cells were pre-treated for 2 hours with 1 μg/mL of mAb 528, a mouse monoclonal antibody which prevents EGF from binding to EGFR (even-numbered lanes), followed by treatment for 30 minutes with vehicle (lanes 1-2), or 1.5 nM of commercial IFNα A (lanes 3-4), IFNα/EGF chimeric activator proteins containing wild-type or mutant IFNα-2a (CAwt, lanes 5-6; CAK133A, lanes 9-10; CAAR144A, lanes 13-14; or CAR149A, lanes 17-18), or the corresponding wild-type or mutant IFNα2a proteins (lanes 7-8, 11-12, 15-16, and 19-20). Pre-treatment of HeLa cells for 2 h. with the mouse monoclonal anti-EGFR antibody 528 inhibits the activation of the STAT1 signaling pathway by the K144A and R149A mutant chimeric activators (FIG. 13, lanes 13-14 and 17-18), but not the activation caused by the non-chimeric IFNα2a and mutants. Neither the wild-type IFNα2a nor the CAwt showed inhibition (FIG. 13, lanes 5-6, 9-10), as expected. The 528 antibody does not itself activate the EGF or the IFNα signal cascades. Treatment with mAb 528 appeared to have no effect on signaling induced by the CA-K133A protein. Since the IFNα element retains significant binding to the IFNAR, it is possible that this chimera was able to displace the antibody from the EGFR during the 30-minute course of the experiment.

Figure 14:
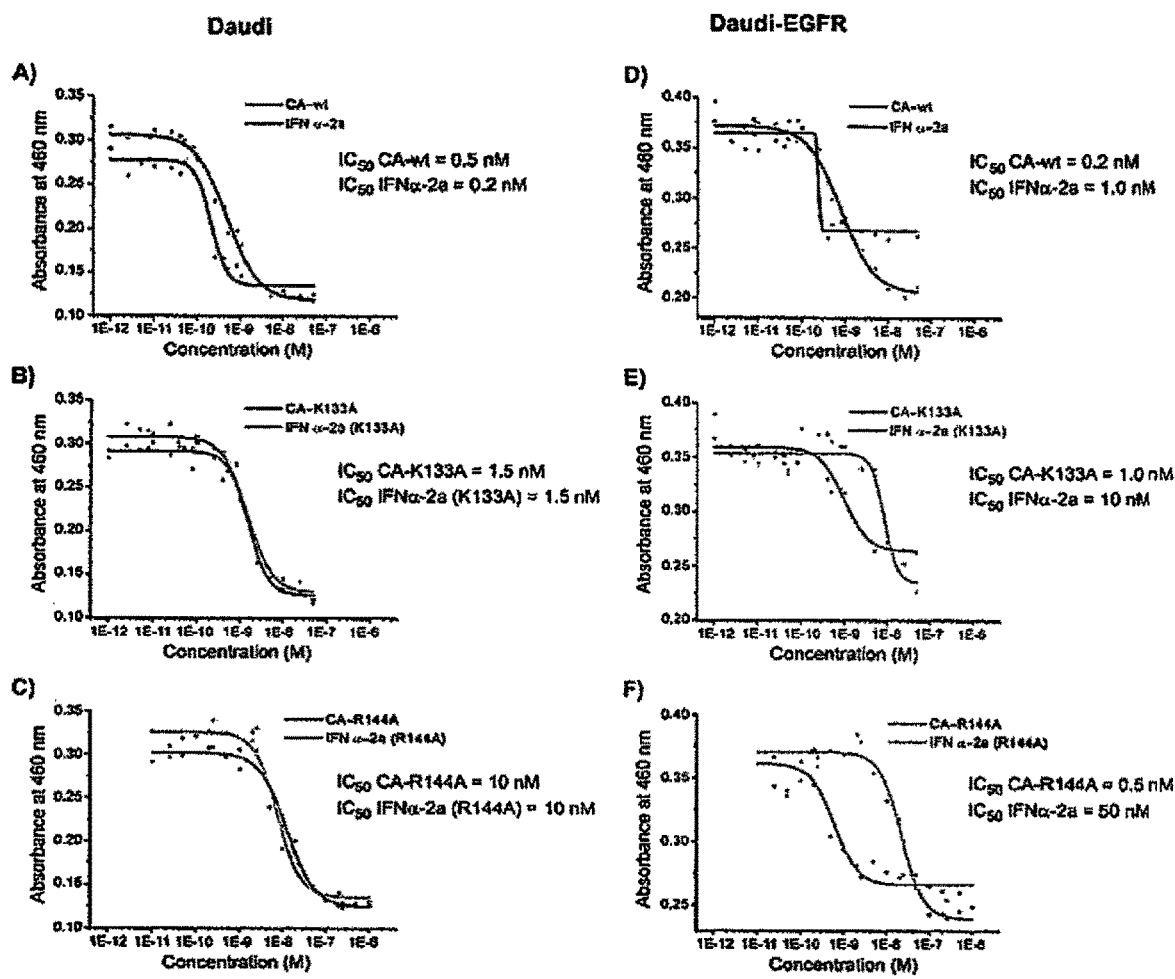
FIG. 14 illustrates an example of EGFR-dependent antiproliferative activity of IFNα2a-EGF chimeric proteins.

EGFR-dependent inhibition of cell proliferation by chimeric activators: The ability of the chimeric proteins to suppress the proliferation of Daudi and Daudi-EGFR cells is shown in FIG. 14. In FIG. 14, Daudi and Daudi-EGFR cells were grown for 60 hours in the presence of various concentrations of IFNα2a-EGF chimeric proteins or the corresponding IFNα2a proteins purified from Pichia. The relative number of viable cells was determined by the production of formazan, which absorbs at A460, from tetrazolium. Curves were fit to the data using a 4-parameter fit (Microcal Origin 5.0). In both cell lines, a dose-dependent growth inhibition was observed. When Daudi cells were treated with the chimeric activators and their IFNα2a counterparts, essentially no difference in their $IC_{50}$s was found (FIGS. 14A-C). Furthermore, the ability to inhibit proliferation diminished according to the ability to bind to IFNAR and activate STAT1.

The chimeric activators, relative to their IFNα counterparts, showed enhanced inhibition of cell proliferation and survival of Daudi-EGFR cells (FIGS. 14E and F). The chimeric activators containing the mutations K133A and R144A were about 10-fold and 100-fold more potent, respectively, than the corresponding IFNα2a mutants alone. CAR149A weakly inhibited proliferation in a pattern that could not be fit to a sigmoid curve (data not shown) and its activity relative to the corresponding IFNα2a mutant therefore could not be quantified.

The behavior of the Daudi-EGFR cells was somewhat affected by the presence of EGFR, which may contribute pro-survival signals. The $IC_{50}$s of wild-type and mutant IFNαs were about 5- to 6-fold higher in Daudi-EGFR (FIG. 14). The maximal extent of proliferation inhibition was also less than for cells treated with IFNα mutants alone. These results are consistent with previous observations that EGF can antagonize the antiproliferative and pro-death effects of IFNα (Caraglia, M., Abbruzzese, A., Leardi, A., Pepe, S., Budillon, A., Baldassare, G., Selleri, C., Lorenzo, S. D., Fabbrocini, A., Giuberti, G., Vitale, G., Lupoli, G., Bianco, A. R., Tagliaferri, P., (1999) Cell Death Differ 6(8), 773-780).

Accordingly, in the experiments described herein, it was evaluated whether the cell-type specificity of an extracellular signaling protein could be altered by a combination of genetic fusion followed by quantitative modulation. The results have implications for understanding the natural design of multisubunit proteins and ligand-receptor interactions, as well as for the design of artificial proteins targeted to cancer cells and other types of disease-causing cells.

In some embodiments, the goal of a particular design was to alter the cell-type specificity of IFNα so that it would only activate its receptor on cells bearing EGFR. EGF was attached to IFNα2a with a flexible linker, so that both modules could simultaneously bind to their receptors. IFNα2a also was mutated so that its ability to bind to its receptor would be significantly reduced, using a set of previously defined mutations that reduce the equilibrium binding of IFNα2a for its receptor by 10-, 40- and 200-fold (Piehler, J., Roisman, L. C., Schreiber, G., (2000) J Biol Chem 275(51), 40425-40433). The purpose was to generate a chimeric protein that would be essentially unable to bind directly to IFNARs, but would bind to EGFR with high affinity. By virtue of the high local concentration of the chimera on the cell surface, the IFNα2a module would then be able to bind to its receptor.

Several lines of evidence indicated that the resulting chimerized, mutated proteins induced IFNα signaling in an EGFR-dependent manner. First, a comparison of IFNα2a (mutant)-EGF chimeras with their unchimerized IFNα2a (mutant) counterparts in HeLa and A431 cells, which express both EGFR and IFNAR, showed that the chimeric proteins were more potent in inducing STAT1 phosphorylation, which results specifically from the activation of IFNAR (FIG. 12). As expected, the differential effect was particularly pronounced for chimeric activators carrying mutations that significantly reduce IFNα binding to its receptor. In contrast, IFNα2a-EGF (CA-wt) was essentially indistinguishable from wild-type IFNα2a; this result is expected because the binding of IFNα to its receptor is quantitatively similar to that for EGF. Second, the activities of the chimerized and unchimerized proteins were compared on Daudi cells and Daudi cells engineered to express EGFR. These results indicated that the enhanced stimulation of STAT1 phosphorylation by the EGF chimeras depended on the presence of EGFR on the cell surface. The improved selectivity of the mutant chimeric activators seen with HeLa and A431 cells was reproduced in Daudi-EGFR cells, but not in parental Daudi cells. Third, the stimulation of STAT1 phosphorylation could be inhibited by an anti-EGFR antibody.

The chimeric activator proteins described here induced a biological response in an EGFR-dependent manner. The proliferation and survival of Daudi cells is inhibited by IFNα2a. Daudi cells expressing EGFR were found to be more sensitive than parental Daudi cells to IFNα2a(mutant)-EGF chimeric activators by up to more than order of magnitude (FIG. 14). In a therapeutic context, the Daudi-EGFR cells may be considered to represent target cells, the parental Daudi cells may represent non-target cells where receptor activation results in side effects, and the differential effect corresponds to the therapeutic index of a protein drug. Thus, by reducing the binding of a given activator and attaching it to a targeting element, the therapeutic index can be improved by more than an order of magnitude.

According to aspects of the invention, the artificial localization/activation system described herein is reminiscent of interactions seen in a number of biological systems. For example, during signal transduction, kinases such as Raf and PDK1 are recruited to the inner face of the cytoplasmic membrane (McKay, M. M., Morrison, D. K., (2007) Oncogene 26(22), 3113-3121), which may enhance the rate of signal transduction as predicted by Adam and Delbruck (Adam, G., Delbruck, M., (1968) Reduction of dimensionality in biological diffusion processes—in: Rich A, Davidson N, editors, Structural chemistry and molecular biology, San Francisco: W. H. Freeman and Co. p. 198-215), by reducing the dimensionality in which substrates can diffuse. In the case of PDK1, a distinct targeting element, the PH domain, interacts with $PIP_3$ in the membrane so that an activity element, the kinase domain itself, can act on its substrates. The binding of HIV gp120 to its target cells also occurs by a two-step process, in which cell-specific targeting occurs through CD4, followed by an activation step mediated by a chemokine receptor (Chan, D. C., Kim, P. S., (1998) Cell 93(5), 681-684; and Blair W S, Lin P-F, Meanwell N A, Wallace O B., (2000) Drug Discovery Today 5(5), 183-194). The interaction between IL-2 and its receptor can occur through an initial contact with a non-signaling receptor subunit, which is followed by a lower-affinity interaction with signaling receptors (Stauber, D. J., Debler, E. W., Horton, P. A., Smith, K. A., Wilson, I. A., (2003) *Proc Natl Acad Sci USA* 103(8), 2788-2793); IL-2 is somewhat analogous to CA-K133A, which has a reduced binding to IFNAR that can be augmented by an additional receptor subunit, with EGFR playing a similar role to the IL-2Rα subunit. These results suggest that such natural interactions can evolve from rather arbitrary associations of transmembrane proteins—for example, there does not need to be any pre-existing interaction between CD4 and chemokine receptors or between IL-2Rα and the other IL-2 receptors for HIV or IL-2 respectively to bind to these combinations of proteins.

Aspects of the invention take advantage, at least in part, of intellectual developments in quantitative systems biology and differ from other targeting approaches in two key respects. First, anticipating that the improvement in cell-type specificity of a chimeric activator might be modest in an initial design, an activator with well-characterized side effects was chosen: IFNα2a by itself is already an approved drug for certain diseases. Second, the chimeric molecule was designed to bind simultaneously to two receptors so that the effect of a reduction-of-function mutation in the activity element is reduced or eliminated by the high local concentration of this element in the neighborhood of its receptor after binding to the targeting receptor.

In some embodiments, aspects of the invention can use a tumor-specific antibody as a targeting element. The molecular designs reported here depended in part on structural models of both the IFNα/IFNAR2 and EGF/EGFR complexes. Use of antibody V regions in chimeric activators will become more feasible as more structures of antibody-receptor complexes are solved (Franklin, M. C., Carey, K. D., Vajdos, F. F., Leahy, D. J., de Vos, A. M., Sliwkowski, M. X., (1994) *Cancer Cell* 5(4), 317-328; and Cho, H-S., Mason, K., Ramyar, K. X., Stanley, A. M., Gabelli, S. B., Denney Jr, D. W., Leahy, D. J., (2003) *Nature* 421(6924), 756-760).

In summary, artificial signaling molecules were constructed based on quantitative principles. According to aspects of the invention, these principles may be used to design and produce chimeric molecules that are useful for therapeutic applications. In addition, further analysis of these principles may allow the further improvement of protein therapeutics and a deeper understanding of the forces that shape natural biological system design.

The abbreviations used in the description of these examples are as follows: CA, chimeric activator; EGF, epidermal growth factor; EGFR, epidermal growth factor receptor; IFNα2a, interferon-alpha2a; IFNAR, IFNα receptor; IL-2, interleukine-2; $Mut^+$, methanol utilization wild-type; $Mut^S$, methanol utilization slow; TGFα, tumor growth factor α; STAT-1, signal transducer and activator 1.

Example 8

Antibody-TRAIL Chimeric Activators for Treatment of Cancer

TRAIL, also known as Apo2L, is a member of the TNF family of proteins, and binds to 'death receptors' such as DR5. TRAIL acts similarly to TNF, but it is thought that TRAIL causes only cell death without accompanying inflammation. The following sequences were designed in which TRAIL is fused to the V regions of the antibody MR1-1, which is described above.

PROTEIN SEQUENCE:
MR1-1:
SEQ ID NO: 18:
QVKLQQSGGGLVKPGASLKLSCVTSGFTFRKFGMSWVRQTSDKRLEWVASISTGGYNTYYSD

NVKGRFTISRENAKNTLYLQMSSLKSEDTALYYCTRGYSPYSYAMDYWGQGTTVTVS
(HEAVY)

SEQ ID NO: 19:
SSGGGSGGGGSGGGGS

SEQ ID NO: 20:
DIELTQSPASLSVATGEKVTIRCMTSTDIDDDMNWYQQKPGEPPKFLISEGNTLRPGVPSRF

SSSGTGTDFVFTIENTLSEDVGDYYCLQSWNVPLTFGdGTKLEIK (Light)

LINKER:
SEQ ID NO: 21:
GGGGSGGGSSGGGSSSGGGGSGGGGSSGGGSGGGS

TRAIL:
SEQ ID NO: 22:
*RERGPQRVAAHITGTRGRSNTLSSPNSKNEKALGRKINSWESSRSGHSFLSNLHLRNGELVI*

*HEKGFYYIYSQTYFRFQEEIKENTKNDKQMVQYIYKYTSYPAPILLMKSARNSCWSKDAEYG*

*LYSIYQGGIFELKENDRIFVSVTNEHLIDMDHEASFFGAFLVG*

MR1-1:
SEQ ID NO: 23:
QVKLQQSGGGLVKPGASLKLSCVTSGFTFRKFGMSWVRQTSDKRLEWVASISTGGYNTYYSD

NVKGRFTISRENAKNTLYLQMSSLKSEDTALYYCTRGYSPYSYAMDYWGQGTTVTVSSSGGG

SGGGGSGGGGSDIELTQSPASLSVATGEKVTIRCMTSTDIDDDMNWYQQKPGEPPKFLISEG

NTLRPGVPSRFSSSGTGTDFVFTIENTLSEDVGDYYCLQSWNVPLTFGdGTKLEIKGGGGSG

-continued
GGSSGGGSSSGGGGSGGGGSSGGGSGGGSRERGPQRVAAHITGTRGRSNTLSSPNSKNEKAL

GRKINSWESSRSGHSFLSNLHLRNGELVIHEKGFYYIYSQTYFRFQEEIKENTKNDKQMVQY

IYKYTSYPAPILLMKSARNSCWSKDAEYGLYSIYQGGIFELKENDRIFVSVTNEHLIDMDHE

ASFFGAFLVG

DNA SEQUENCE:
SEQ ID NO: 24:
CAAGTTAAGTTGCAACAATCCGGTGGTGGTTTGGTTAAGCCAGGTGCTTCTTTGAAGTTGTC

TTGTGTTACTTCTGGTTTTACTTTTAGAAAGTTTGGTATGTCTTGGGTTAGACAAACTTCTG

ATAAGAGATTGGAATGGGTTGCTTCTATTTCTACTGGTGGTTACAACACTTACTACTCTGAT

AACGTTAAGGGTAGATTTACTATTTCCAGAGAGAACGCTAAGAACACTTTGTACTTGCAAAT

GTCTTCTTTGAAGTCTGAAGATACTGCTTTGTACTACTGTACTAGAGGTTACTCTCCATACT

CTTACGCTATGGATTACTGGGGTCAAGGTACTACTGTTACTGTTTCTTCCTCCGGTGGAGGT

TCCGGTGGTGGAGGATCTGGTGGTGGTGGTTCTGATATTGAGTTGACTCAATCTCCAGCTTC

TTTGTCTGTTGCTACTGGTGAGAAGGTTACTATTAGATGTATGACTTCTACTGATATTGATG

ATGTATGAACTGGTACCAACAAAAGCCAGGTGAACCACCAAAGTTTTTGATTTCTGAAGGT

AACACTTTGAGACCAGGTGTTCCATCCAGATTTTCTTCTTCTGGTACTGGTACTGATTTTGT

TTTTACTATTGAGAACACTTTGTCTGAAGATGTTGGTGATTACTACTGTTTGCAATCTTGGA

ACGTTCCATTGACTTTTGGTGATGGTACTAAGTTGGAGATTAAGGGAGGAGGTGGTTCCGGT

GGTGGTTCTTCCGGAGGTGGTTCTTCCTCTGGAGGTGGTGGTTCAGGTGGAGGTGGTTCCTC

TGGAGGTGGTTCTGGTGGAGGTTCCAGAGAAAGAGGTCCACAAAGAGTTGCTGCTCACATTA

CTGGTACTAGAGGTAGATCTAACACTTTGTCTTCTCCAAACTCTAAGAACGAAAAGGCTTTG

GGTAGAAAGATTAACTCTTGGGAGTCTTCCAGATCTGGTCATTCTTTCTTGTCTAACTTGCA

TTTGAGAAACGGTGAATTGGTTATTCATGAGAAGGGTTTCTACTACATTTACTCTCAAACTT

ACTTTAGATTTCAAGAAGAAATTAAGGAGAACACTAAGAACGATAAGCAAATGGTTCAATAC

ATTTACAAGTACACTTCTTACCCAGCTCCAATTTTGTTGATGAAGTCTGCTAGAAACTCTTG

TTGGTCTAAGGATGCTGAATACGGTTTGTACTCTATTTACCAAGGTGGTATTTTCGAATTGA

AGGAGAACGATAGAATTTTCGTTTCTGTTACTAACGAACATTTGATTGATATGGATCACGAA

GCTTCTTTCTTTGGTGCTTTTTTGGTTGGT

The sequences are highlighted so that the first and third segments (regular text) are the heavy chain V region and the light chain V region respectively. The second (bolded text) is a linker, the fourth (underlined text) is a longer linker, and the fifth segment (italicized text) is TRAIL or an active fragment of TRAIL. In the case of the sequence shown, the active fragment corresponds to amino acids 115-281 and is 1.5 times more bioactive than the full-length TRAIL (Hymowitz et al. Biochemistry, Vol. 39, No. 4, p. 633 (2000)).

Three different mutant forms of TRAIL can be used, containing the mutations:
Q205A
Y216A
Y237A The chimeric proteins containing normal TRAIL and the mutations X, Y, and Z were tested for their ability to induce apoptosis in the glioblastoma cells U87MG and their engineered derivative U87MG-EGFRvIII. EGFRvIII is a deleted derivative of EGFR that is found in some cancers and contains a novel peptide junction that is recognized by the antibody MR1-1.

The following results will be obtained. Plus signs indicate levels of apoptosis by viability and apoptosis signaling assays. Apoptosis assessed by viability assay will be measure by using the cell proliferation reagent WST-1. Apoptosis signaling will be measure by caspase activation using antibodies directed against caspase-8 and active caspase-3.

|  | U87MG | U87MG-EGFRvIII |
| --- | --- | --- |
| TRAIL (+) | ++++ | ++++ |
| TRAIL (Q205A) | ++ | ++ |
| TRAIL (Y216A) | + | + |
| TRAIL (Y237A) | − | − |
| MR1-1-TRAIL (+) | ++++ | ++++ |
| MR1-1-TRAIL (Q205A) | ++ | ++++ |
| MR1-1-TRAIL (Y216A) | + | +++ |
| MR1-1-TRAIL (Y237A) | − | ++ |

Example 9

Use of an Anti-CEA Antibody Instead of MR1-1

Sequences of chimeric activators also were designed using the antibody V regions from a humanized version of the antibody T84.66, which is directed against carcinoembryonic antigen (CEA). Carcinoembryonic antigen is a protein that is highly expressed on colon cancers, lung cancers, breast cancers, and other types of cancer. It is expressed in only small amounts on normal tissues in the gastrointestinal tract. CEA is also highly expressed in the tumor cell lines GW39, LS147T and SW1417.

The CEA protein has seven extra cellular immunoglobulin-family domains and is attached to the cell surface by means of a lipid anchor at its C-terminus; this protein contains no intracellular amino acids. A large number of antibodies against CEA have been identified, of which T84.66 and MFE-23 are particularly well characterized. The antibody T84.66 was chosen because it binds somewhere within the two most membrane-proximal domains (Hass et al. Cancer Research [1991] 51:1876), while MFE-23 binds to a much more membrane-distal domain that might lie more than 200 angstroms from the cell surface (Boehm and Perkins, FEBS Letters [2000] 475:11). The T84.66 binding site therefore appears to be about the same height from the cell membrane as the TRAIL N- and C-termini, and also the IFNα N- and C-termini, when these ligands are bound to their receptors.

Based on these considerations, a chimeric activator was designed containing humanized T84.66 V regions and TRAIL.

```
PROTEIN SEQUENCE:
T84.66:
SEQ ID NO: 25:
EVQLVESGGGLVQPGGSLRLSCAASGFNIKDTYMHWVRQAPGKGLEWVARIDPANGNSKYVP

KFQGRATISADTSKNTAYLQMNSLRAEDTAVYYCAPFGYYVSDYAMAYWGQGTLVTVSS
(HEAVY)

SEQ ID NO: 26:
SSSGGGSGGGSGGGGS

SEQ ID NO: 27:
DIQLTQSPSSLSASVGDRVTITCRAGESVDIFGVGFLHWYQQKPGKAPKLLIYRASNLESGV

PSRFSGSGSRTDFTLTISSLQPEDFATYYCQQTNEDPYTFGQGTKVEIK (light)

LINKER:
SEQ ID NO: 28:
GGGGSGGGSSGGGSSSGGGGSGGGGSSGGGSGGGS

TRAIL:
SEQ ID NO: 29:
RERGPQRVAAHITGTRGRSNTLSSPNSKNEKALGRKINSWESSRSGHSFLSNLHLRNGELVI

HEKGFYYIYSQTYFRFQEEIKENTKNDKQMVQYIYKYTSYPAPILLMKSARNSCWSKDAEYG

LYSIYQGGIFELKENDRIFVSVTNEHLIDMDHEASFFGAFLVG

T84.66:
SEQ ID NO: 30:
EVQLVESGGGLVQPGGSLRLSCAASGFNIKDTYMHWVRQAPGKGLEWVARIDPANGNSKYVP

KFQGRATISADTSKNTAYLQMNSLRAEDTAVYYCAPFGYYVSDYAMAYWGQGTLVTVSSSSS

GGGSGGGSGGGGSDIQLTQSPSSLSASVGDRVTITCRAGESVDIFGVGFLHWYQQKPGKAP

KLLIYRASNLESGVPSRFSGSGSRTDFTLTISSLQPEDFATYYCQQTNEDPYTFGQGTKVEI

KGGGGSGGGSSGGGSSSGGGGSGGGGSSGGGSGGGSRERGPQRVAAHITGTRGRSNTLSSPN

SKNEKALGRKINSWESSRSGHSFLSNLHLRNGELVIHEKGFYYIYSQTYFRFQEEIKENTKN

DKQMVQYIYKYTSYPAPILLMKSARNSCWSKDAEYGLYSIYQGGIFELKENDRIFVSVTNEH

LIDMDHEASFFGAFLVG

DNA SEQUENCE:
SEQ ID NO: 31:
GAAGTTCAATTGGTTGAATCTGGAGGTGGTTTGGTTCAACCAGGTGGTTCTTTGAGATTGTC

TTGTGCTGCTTCTGGTTTTAACATTAAGGATACTTACATGCATTGGGTTAGACAAGCTCCAG

GTAAGGGTTTGGAATGGGTTGCTAGAATTGATCCAGCTAACGGTAACTCTAAGTACGTTCCA

AAGTTTCAAGGTAGAGCTACTATTTCTGCTGATACTTCTAAGAACACTGCTTACTTGCAAAT
```

```
                        -continued
GAACTCTTTGAGAGCTGAAGATACTGCTGTTTACTACTGTGCTCCATTTGGTTACTACGTTT

CTGATTACGCTATGGCTTACTGGGGTCAAGGTACTTTGGTTACTGTTTCTTCCTCCTCTTCT

GGTGGAGGTTCTGGAGGTGGTGGATCTGGTGGAGGTGGTTCTGATATTCAATTGACTCAATC

TCCATCTTCTTTGTCTGCTTCTGTTGGTGATAGAGTTACTATTACTTGTAGAGCTGGTGAAT

CTGTTGATATTTTTGGTGTTGGTTTTTTGCATTGGTACCAACAAAAGCCAGGTAAGGCTCCA

AAGTTGTTGATTTACAGAGCTTCTAACTTGGAATCTGGTGTTCCATCCAGATTTTCTGGTTC

TGGTTCCAGAACTGATTTTACTTTGACTATTTCTTCTTTGCAACCAGAAGATTTTGCTACTT

ACTACTGTCAACAAACTAACGAAGATCCATACACTTTTGGTCAAGGTACTAAGGTTGAAATT

AAGGGTGGAGGAGGTTCTGGTGGTGGATCTTCCGGAGGTGGTTCTTCCTCTGGAGGTGGTGG

TTCAGGTGGAGGTGGTTCCTCTGGAGGTGGTTCTGGTGGAGGTTCCAGAGAAAGAGGTCCAC

AAAGAGTTGCTGCTCACATTACTGGTACTAGAGGTAGATCTAACACTTTGTCTTCTCCAAAC

TCTAAGAACGAAAAGGCTTTGGGTAGAAAGATTAACTCTTGGGAGTCTTCCAGATCTGGTCA

TTCTTTCTTGTCTAACTTGCATTTGAGAAACGGTGAATTGGTTATTCATGAGAAGGGTTTCT

ACTACATTTACTCTCAAACTTACTTTAGATTTCAAGAAGAAATTAAGGAGAACACTAAGAAC

GATAAGCAAATGGTTCAATACATTTACAAGTACACTTCTTACCCAGCTCCAATTTTGTTGAT

GAAGTCTGCTAGAAACTCTTGTTGGTCTAAGGATGCTGAATACGGTTTGTACTCTATTTACC

AAGGTGGTATTTTCGAATTGAAGGAGAACGATAGAATTTTCGTTTCTGTTACTAACGAACAT

TTGATTGATATGGATCACGAAGCTTCTTTCTTTGGTGCTTTTTTGGTTGGT
```

Protein activity is measured as in the previous example but using LS147T and SW1417 cell lines.

Example 10

Antibody-Erythropoietin Chimeric Activators for Treatment of Anemia

Erythropoietin (Epo) is a hormone that stimulates production of red blood cells. Epo can be used to treat anemia that may be part of many disease conditions, but is used primarily in two settings. First, kidney failure patients usually do not produce adequate levels of Epo, which is expressed mainly in the kidneys, and are therefore anemic. Second, cancer patients often become anemic as a result of chemotherapy treatment, which kills dividing cells including red blood cell precursors.

Use of erythropoietin can also affect platelet production, possibly because receptors for Epo are also found on hematopoietic precursor cells that give rise to platelets. In addition, Epo receptors are sometimes found on cancer cells, and Epo may enhance tumor cell growth and angiogenesis. It would be useful to have a form of Epo that only stimulated red blood cell production and did not bind to Epo receptors on other cells, such as cancer cells or early hematopoietic stem cells that can give rise to other cell types.

By way of background, a person is considered to be anemic if their hemoglobin levels are less than 12 grams/deciliter for women or <14 g/dl for men. These values correspond to a hematocrit of 37% for women and 40% for men, and a red blood cell count of $4 \times 10^{12}$/l for women and $4.5 \times 10^{12}$ for men. Usually when people are treated with Epo, the levels of red blood cells are not fully restored, since this is associated with an increased rate of heart attack and stroke.

Recent studies suggest that Epo may in fact accelerate tumor growth in human patients (reviewed by Khuri, FR [2007] New England Journal of Medicine 356:24:2445-2448; and Crawford, [2007] Journal of Clinical Oncology 25:9:1021-1023). This is disappointing, because it had been thought that increasing red blood cell counts in cancer patients would increase their quality of life, and also increase the oxygenation of tumors, making them more sensitive to radiation and other types of treatments.

In one study, patients with non-small cell lung cancer were given erythropoietin or a placebo, and the treated group was found to have decreased overall survival (Wright et al. 25:9:1027-1032). In another study, breast cancer patients received Epo or a placebo, and again the treated group had decreased survival (Leyland-Jones et al. [2005] Journal of Clinical Oncology 23:25:5960-5972). In this study, the patients in each group with higher hemoglobin levels survived longer, so it does not appear that the increase in red blood cells caused by Epo was the cause of the decreased survival. In an important pair of studies, Henke et al. studied the effect of Epo treatment on patients with head and neck cancer, and found that the treated group survived less well than the placebo group (Henke et al. [2003] Lancet 362:9392:1255-60). They then tested the tumors from these patients for expression of Epo receptors, and found that, in the Epo-treated group, patients with tumors expressing Epo receptors did not survive as long as patients whose tumors did not express Epo receptors. In the placebo group, patients did about equally well regardless of whether their tumors expressed Epo receptors (Henke et al. [2006] Journal of Clinical Oncology 24:29:4708-4713). These results strongly indicate that Epo can shorten the survival of cancer patients by bind to Epo receptors on tumor cells and enhancing the growth or survival of the tumor cells.

Glycophorin is a highly expressed protein on the surface of red blood cells. Glycophorin is also expressed on the precursors of red blood cells (Southcott et al. Blood [1999] 12:4425). During production of red blood cells, precursor hematopoietic stem cells (HSCs) undergo a series of differentiation steps as follows:

HSCs→BFU-E→CFU-E→terminal red blood cells where BFU-E and CFU-E are 'blast-forming unit' and 'colony-forming unit'. BFU-E cells produce about 50,000 red blood cells, while CFU-E cells produce about 1,000 red blood cells. CFU-E cells are particularly dependent on erythropoietin for survival and cell division (Adamson et al. Blood Cells [1978] 4:89). By constructing a molecule that is targeted to glycophorin-expressing cells, red blood cell production may be stimulated without affecting other cell types.

Glycophorin A exists in two allelic forms, M and N, which define the M and N blood groups. These forms differ at the N-terminus as follows (Czerwinski et al [1998] The Journal of Immunology 160: 4406-4417)

```
         1    2    3    4    5
M: NH2  Ser  Ser  Thr  Thr  Gly . . .(SEQ ID NO: 32)
N: NH2  Leu  Ser  Thr  Thr  Glu . . .(SEQ ID NO: 33)
```

Catimel B. et al. Journal of Immunological Methods [1993] 165:183 described a monoclonal antibody, 10F7MN that recognizes the N and M-type of glycophorin A. It should be noted that certain serine and threonine residues in glycophorin are O-glycosylated, and the 10F7MN antibody actually recognized a combination of the amino acid and sugar structures. Based on the sequence of the 10F7MN V regions and human erythropoietin, a series of chimeric activators were designed with the following general structure: 10F7MN (heavy chain V region)—short linker—10F7MN (light chain V region)—long linker—erythropoietin. The specific sequence design shown below uses the original mouse-derived V regions of 10F7MN, but it is also possible to use a humanized pair of V regions. (Use of other monoclonal antibody directed against glycophorin is also possible, such as GPA105, [Wasniowska et al., Mol. Immunol. {1992} 29:6:783-91] or 5F4).

```
PROTEIN SEQUENCE:
10F7MN:
SEQ ID NO: 34:
MAQVKLQQSGAELVKPGASVKLSCKASGYTFNSYFMHWMKQRPVQGLEWIGMIRPNGGTTDY

NEKFKNKATLTVDKSSNTAYMQLNSLTSGDSAVYYCARWEGSYYALDYWGQGTTVTVSS
(HEAVY)

SEQ ID NO: 35:
GGGGSGGGGSSGGGGSS

SEQ ID NO: 36:
DIELTQSPAIMSATLGEKVTMTCRASSNVKYMYWYQQKSGASPKLWIYYTSNLASGVPGRFS

GSGSGTSYSLTISSVEAEDAATYYCQQFTSSPYTFGGGTKLEIKRAAA (light)

Linker:
SEQ ID NO: 37:
GGGGSGGGSSGGGSSSGGGGSGGGGSSGGGSGGGS

EPO:
SEQ ID NO: 38:
APPRLICDSRVLQRYLLEAKEAENITTGCAEHCSLNENITVPDTKVNFYAWKRMEVGQQAVE

VWQGLALLSEAVLRGQALLVNSSQPWEPLQLHVDKAVSGLRSLTTLLRALGAQKEAISPPDA

ASAAPLRTITADTFRKLFRVYSNFLRGKLKLYTGEACRTGDR

10F7MN:
SEQ ID NO: 39:
MAQVKLQQSGAELVKPGASVKLSCKASGYTFNSYFMHWMKQRPVQGLEWIGMIRPNGGTTDY

NEKFKNKATLTVDKSSNTAYMQLNSLTSGDSAVYYCARWEGSYYALDYWGQGTTVTVSSGGG

GSGGGGSSGGGGSSDIELTQSPAIMSATLGEKVTMTCRASSNVKYMYWYQQKSGASPKLWIY

YTSNLASGVPGRFSGSGSGTSYSLTISSVEAEDAATYYCQQFTSSPYTFGGGTKLEIKRAAA

GGGGSGGGSSGGGSSSGGGGSGGGGSSGGGSGGGSAPPRLICDSRVLQRYLLEAKEAENITT

GCAEHCSLNENITVPDTKVNFYAWKRMEVGQQAVEVWQGLALLSEAVLRGQALLVNSSQPWE

PLQLHVDKAVSGLRSLTTLLRALGAQKEAISPPDAASAAPLRTITADTFRKLFRVYSNFLRG

KLKLYTGEACRTGDR
```

-continued

DNA SEQUENCE:
SEQ ID NO: 40:
ATGGCTCAAGTTAAGTTGCAACAATCTGGTGCTGAATTGGTTAAGCCAGGTGCTTCTGTTAA

GTTGTCTTGTAAGGCTTCTGGTTACACCTTCAACTCTTACTTTATGCATTGGATGAAGCAAA

GACCAGTTCAAGGTTTGGAATGGATTGGTATGATTAGACCAAACGGTGGTACTACCGATTAC

AACGAGAAGTTTAAGAACAAGGCTACTTTGACTGTTGATAAGTCCTCTAACACTGCTTACAT

GCAATTGAACTCTTTGACTTCTGGTGATTCTGCTGTTTACTACTGTGCTAGATGGGAAGGTT

CTTACTACGCTTTGGATTACTGGGGTCAAGGTACCACTGTTACTGTTTCTTCCGGTGGAGGT

GGATCTGGTGGTGGAGGATCTTCAGGAGGTGGTGGATCTTCCGATATTGAGTTGACTCAATC

TCCAGCTATTATGTCTGCTACCTTGGGTGAGAAGGTTACTATGACTTGTAGAGCTTCATCTA

ACGTTAAGTACATGTACTGGTACCAACAGAAGTCTGGTGCTTCTCCAAAGTTGTGGATTTAC

TACACTTCTAACTTGGCTTCTGGTGTTCCAGGTAGATTTTCTGGTTCAGGTTCTGGTACTTC

CTACTCTTTGACTATTTCCTCTGTTGAAGCTGAAGATGCTGCTACTTACTACTGTCAACAAT

TCACTTCTTCCCCATACACTTTTGGAGGAGGTACTAAGTTGGAAATCAAGAGAGCTGCCGCA

GGTGGAGGTGGTTCCGGAGGAGGATCTTCCGGTGGTGGATCTTCTTCTGGAGGTGGAGGATC

CGGTGGTGGAGGATCATCTGGTGGAGGATCTGGTGGTGGTTCCGCTCCACCTAGATTGATTT

*GTGATTCCAGAGTTTTGGAAAGATACTTGTTGGAAGCTAAGGAGGCTGAAAAGATTACTACT*

*GGTTGTGCTGAACATTGTTCTTTGAACGAGAAGATTACTGTTCCAGATACTAAGGTTAACTT*

*TTACGCTTGGAAGAGAATGGAAGTTGGTCAGCAAGCTGTTGAAGTTTGGCAAGGTTTGGCTT*

*TGTTGTCTGAAGCTGTTTTGAGAGGTCAAGCTTTGTTGGTTAAGTCTTCTCAACCATGGGAA*

*CCATTGCAATTGCATGTTGATAAGGCTGTTTCTGGTTTGAGATCTTTGACTACCTTGTTGAG*

*AGCTTTGGGTGCTCAAAAGGAAGCTATTTCTCCTCCAGATGCTGCTTCTGCCGCTCCATTGA*

*GAACTATTACTGCTGATACTTTTAGAAAGTTGTTTAGAGTTTACTCTAACTTCTTGAGAGGT*

*AAGTTGAAGTTGTACACTGGTGAAGCTTGTAGAACTGGTGATAGA*

(The length of the long linker may need to be varied depending on which anti-glycophorin antibody is used and where the epitope is.)

This molecule will be expressed in Pichia pastoris. Because Epo is glycosylated at a number of sites and it will ultimately be useful to have a molecule with mammalian-type glycosylation, a 10F7MN-Epo chimeric activator also will be expressed in a mammalian cell line such as CHO cells.

To reduce the activity of the Epo portion, a mutation that reduces the affinity of Epo for its receptor will be introduced. Elliott et al. (Blood [1997] 89:2:493-502) described a series of mutations in erythropoietin that reduce its activity. In some embodiments, at least one or more of the following mutations may be used:

N147A

N147K

R150A

R150E

To test the chimeric activators, a test system that uses one of the following cell lines can be constructed and used: TF-1, UT-7 or ERY-1. These are cells that respond to Epo. The cell line can be transfected with an expression construct that expresses human glycophorin, and the chimeric activators can be tested in this pair of cell lines.

EPO activity will be measured by proliferation and signaling assays. Proliferation will be assessed by using WST-1 reagent while pSTAT5 will be measured for EPO receptor activation.

The following results will be obtained:

| | | TF-1 | TF-1_Glycophorin A |
|---|---|---|---|
| EPO | | ++++ | ++++ |
| EPO (N147A) | | ++ | ++ |
| EPO (R150A) | − | + | + |
| EPO (R150E) | − | + | + |
| EPO (N147K) | | − | − |
| 10F7MN - EPO | | ++++ | ++++ |
| 10F7MN - EPO (N147A) | | ++ | ++++ |
| 10F7MN - EPO (R150A) | | + | +++ |
| 10F7MN - EPO (R150E) | | − | ++ |
| 10F7MN - EPO (N147K) | | − | + |

For a test in an animal system, the following strategy can be used. Glycophorin is a protein that has changed rapidly in evolution, so that the epitopes recognized by existing anti-human glycophorin are not found in most other animals. Lethally irradiated mice that have been reconstituted with human hematopoietic stem cells can be used.

Example 11

1. General Model for Chimera Design

Aspects of theoretical chimera design appear to be a difficult task, and no theoretical approaches have been focused on the field. Many variables are involved, both physical and kinetic, as well as concentrations, and dynamics. In addition, the size of the receptors need to be taken into account for an optimal chimera design and maximum selectivity. Ligands may be linked by a long amino acid chain, wherein the length is a determinant of the chimera performance, and it needs to be carefully designed according to the physical and kinetic characteristics of the system.

Over the past years, theoretical efforts have been mainly focused on understanding and modeling single receptor-ligand interaction and internalization. Here a successful theoretical approach for single receptor signaling has been extended to chimeras interacting with an arbitrary number of different receptors. To test the results, the case of a simple homodimer and a heterodimer were explored, and the theoretical predictions were compared with experimental data. In addition, the theoretical prediction of the optimal length of the linker in the case of a heterodimer was compared with experimental results.

Herein a general theory for chimera design is presented, for testing mutant ligands with known affinity and for designing optimal linker length for increased selectivity. The theory is presented for chimeras designed by binding of an arbitrary number n linked by amino acid chains of different lengths.

The process of binding is assumed to occur in the following steps: the chimera binds initially to one of the receptors (receptor i) with a rate of binding $k_{on;i}$; and dissociation $k_{off;i}$, internalization by endocytosis of the free receptor $k_{t;i}$ and active receptor $k_{e;i}$ and receptor recycling $Q_{r;i}$ rates equivalent to the non chimeric ligand. This first reaction of ligand-receptor i recruits chimeric proteins to the cell membrane, increasing the local concentration of ligand j in the surface of the cell, enhancing interaction of ligand j and its receptor.

The effect of the two dimensional diffusion of the receptors is neglected (if compared with other dynamical processes in the system, it can be considered instantaneous).

2. Equations for the General System

Certain equations described herein are useful to model generalized chimeric binding systems, with an additional term that accounts for the coupling between ligand concentration due to the chimera. The general equations for a set of n ligands and n receptors are as follows.

$$\frac{dR_i}{dt} = -k_{i,on} R_i L + k_{i,off} C_i - k_{i,t} R_i + Q_{i,R} - R_i \sum_{j=1, j \neq i}^{n} (k'_{i,j,on} L_{i,j}) \quad (13)$$

$$\frac{dC_i}{dt} = k_{i,on} R_i L - k_{i,off} C_i - k_{i,e} C_i + R_i \sum_{j=1, j \neq i}^{n} (k'_{i,j,on} L_{i,j}) \quad (14)$$

$$\frac{dL}{dt} = \frac{1}{N_{Av} V} \sum_{i=1}^{n} (k_{i,off} C_i - k_{i,on} R_i L) \quad (15)$$

where $R_i$ and $C_i$ are the total number of empty and bound receptor i. L is the concentration of chimera in solution. The last term of equations 13 and 14 reflects the increase in local concentration of ligand i due to the binding of the ligand j to its receptor.

Once the ligand j is bound to the receptor j, an increase in the local concentration of ligand i close to the cell membrane is created, and the ligand i can be assumed to be distributed in a volume gasket which depends on the distance between ligand i and j. This local concentration of i due to the binding of the j ligand-receptor complex can be calculated as follows.

$$L_{i,j} = \frac{C'_j}{N_{Av} V_{0,i,j}} = \frac{3 C'_j}{4 \pi} \frac{1}{(r + a_{i,j})^3 - r^3} \quad (16)$$

where $N_{Av}$ is the Avogadro's number, r is the average cell radius and $C_{0j}$ is the concentration of the $C_j$ result of the regular binding mechanism, i.e., the number of complexes $C_j$ bounded to a chimera that it is not bound to another receptor, responsive of the local concentration increase.

$$\frac{dC'_j}{dt} = k_{j,on} R_j L - k_{j,off} C_j - k_{j,e} C_j \quad (18)$$

Figure 16:
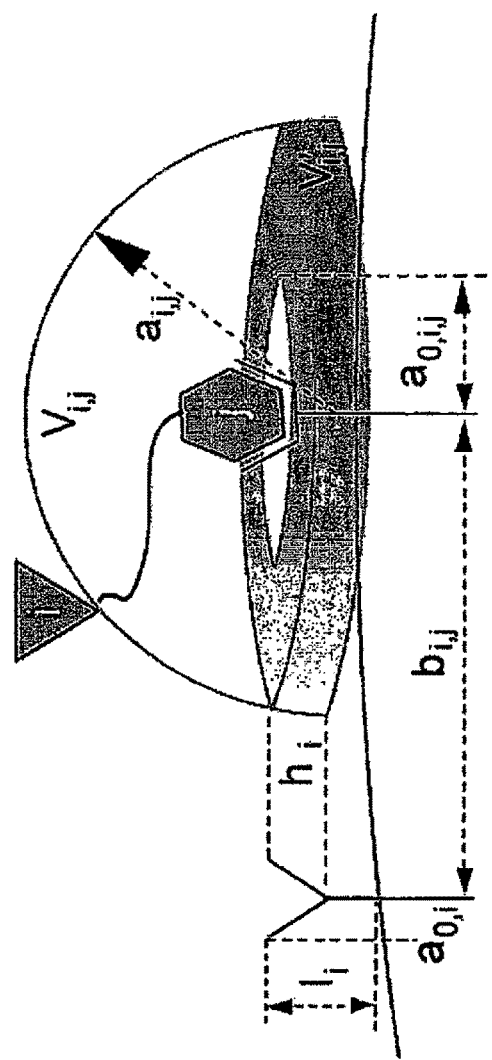
FIG. 16 shows a schematic of an embodiment of the binding mechanism between a receptor and a free ligand or a chimeric ligand.

Regarding the binding mechanism between a receptor and a free ligand or a chimeric ligand, it is reasonable to assume certain scaling in the reaction rate, due to the geometrical characteristics of the problem. So, in the last term of equations 13 and 14 the reaction rate needs to be rescaled having in mind that reaction ligand-receptor-i only occurs when the ligand is in the close vicinity of the receptor. The mechanism is illustrated in FIG. 16, and the reaction only occurs in the dark volume of the semi-sphere of radius $a_{i,j}$ This way, the rescaled reaction rate is in the form:

$$k'_{i,j,on} = k_{j,on} \frac{V'_{i,j}}{V_{i,j}} = \frac{3 h_i}{4} \frac{(a_{i,j}^2 - a_{0,i,j}^2)}{a_{i,j}^3} \quad (19)$$

here, $h_i$ is the height of the gasket, which corresponds to the location where the ligand can bind to the receptor. $a_{0,j}$ is the radius of the receptor j.

It is assumed that the free end of the chimera is distributed over time in the two regions $V_{0\ i,j}$ and $V_{i,j}$ proportionally to their size, so the reaction rate needs to be scaled according to this.

The quantity $a_{i,j}$ is the distance between ligand i and j. $a_{0;i,j}$ is the minimum linker distance, and depends on geometrical characteristics of the receptors involved.

$$a_{0,i,j} = \sqrt{(a_{j,0} + a_{i,0})^2 + |l_i - l_j|^2} \quad (21)$$

For a given ligand concentration L, the previous equations will give the number of free molecules of the receptor i in the cell surface ($R_i$), and the number of complex ligand-receptor molecules in the surface prior to internalization ($C_i$).

3. Chimera Dimer

The theory is now restricted to a case of a hetero-dimer, e.g., two different ligands linked to a receptor. This particular situation is the common scenario for chimera design. As a numerical approach, values are used for the case of EGF linked to different mutants of the IF molecule. The result will be compared with experimental values that predict greater selectivity for various mutants compared with the wild type case.

Figure 15:
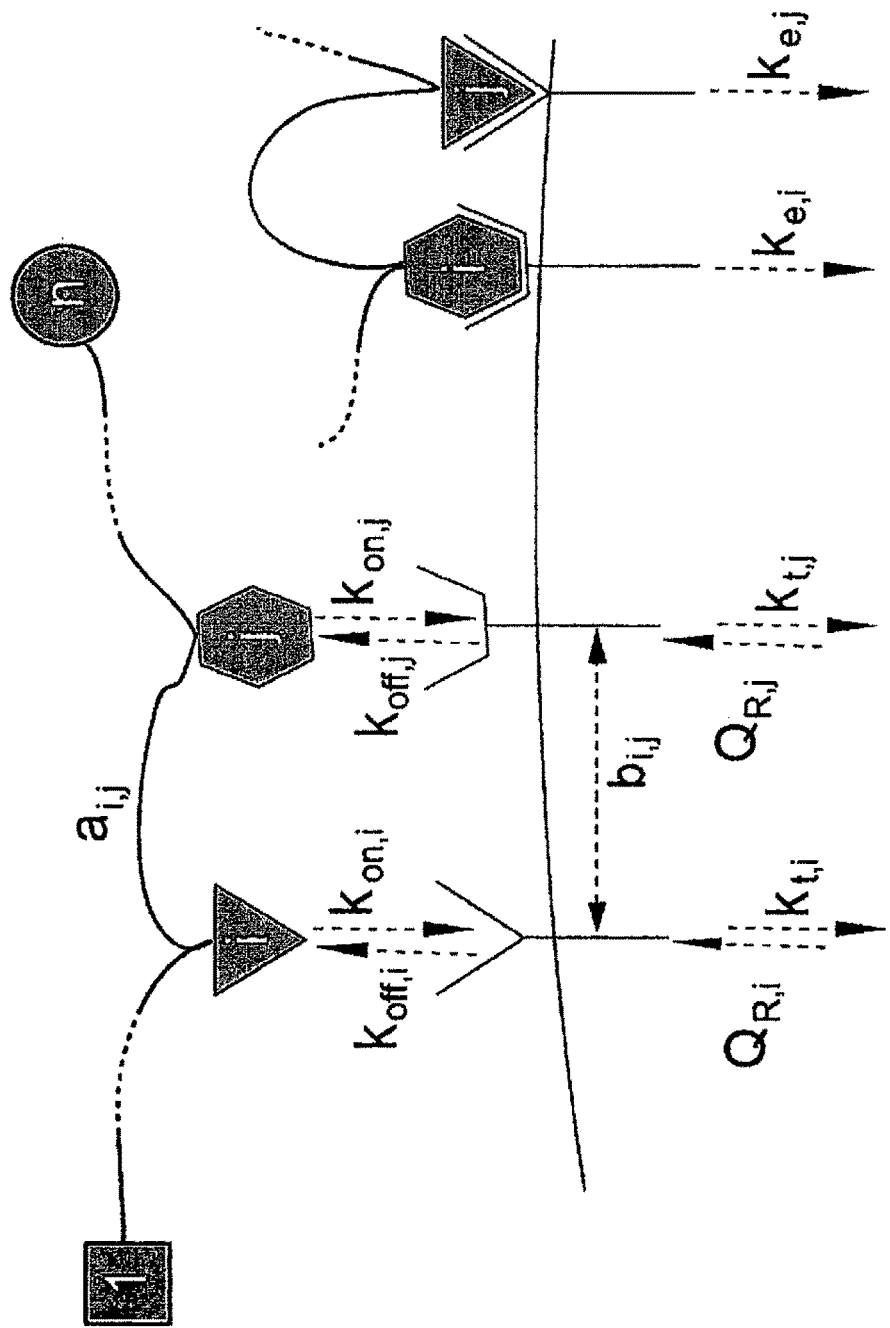
FIG. 15 shows a schematic of an embodiment of the chimera-receptor binding and receptor endocytosis where all model parameters are represented (the average distance between two receptors is shown as $b_{i,j}$)

The model consists of 7 variables, one for each configuration of each of the two receptors and one for the ligand concentration. The interacting components with their corresponding relevant chemical parameters are illustrated in FIG. 15. The components of the model are subjected to 4 reversible and 3 irreversible reactions:

$$L_2 + R_2 \leftrightarrow C_2 \quad k'_{2,on}, k_{2,off} \tag{3}$$

$$L_1 + R_1 \leftrightarrow C_1 \quad k'_{1,on}, k_{1,off} \tag{4}$$

$$C_1, C_2, C'_1, C'_2 \rightarrow \cancel{\exists} \quad k_{1,e}, k_{2,e} \tag{5}$$

$$R_1, R_2 \rightarrow \cancel{\exists} \quad k_{1,t}, k_{2,t} \tag{6}$$

$$\cancel{\exists} \rightarrow R_1, R_2 \quad Q_1, Q_2 \tag{7}$$

Where R1 and R2 are the amount of the two cell surface receptors that the chimera ligand L is targeting. The variables $C_1$, $C_2$, $C_1'$ and $C_2'$ correspond to different configurations of the active ligand-receptor complexes.

Reactions 1 and 2 account for the primary reaction of complex formation of the two species, with their respective affinity ($k_{1,on}$; $k_{2,on}$) and dissociation rates ($k_{1,off}$, $k_{2,off}$). Since every chimera ligand molecule L has two distinct active sites, it can interact with each of the receptors to form two types of complexes $C_1'$ and $C_2'$. The quantities $C_1'$ and $C_2'$ represent the total amount of complexes where one of the two active sites of the chimera is free and able to interact with its complementary receptor. This way, when the primary complexes C'1 and C'2 are formed through reaction 1 or 2, a local concentration of the remaining active site is created on the cell surface, which favors the formation of the complementary complex.

In other words, when a $C_1'$ complex is formed through reaction 1, a local concentration of ligand with only the second binding site available is created on the cell surface. This local concentration, referred to as $L_2$, is able to interact with $R_2$ through reaction 3 to form a $C_2$ complex. In the same way, the $C_2'$ complexes formed through reaction 2 give rise to L1, favoring the formation of the complex $C_1$ through reaction 4. These local concentrations $L_1$ and $L_2$ are distributed in a spherical gasket of inner diameter equal to the cell diameter r and height equal to the size of the linker a between the two ligands of the chimera.

Expressions for the calculation of the L1 and L2 local concentrations are:

$$L_1 = \frac{C_2'}{N_{Av}V_0} = \frac{3C_2'}{4\pi} \frac{1}{(r+a)^3 - r^3} \tag{8}$$

$$L_2 = \frac{C_1'}{N_{Av}V_0} = \frac{3C_1'}{4\pi} \frac{1}{(r+a)^3 - r^3} \tag{9}$$

where $N_{Av}$ is the Avogadro's number and $V_0$ is the gasket volume. The only contribution to the local concentration comes from the complexes $C_{O1}$ and $C_{O2}$, since the complexes $C_1$ and $C_2$ formed through reactions 3 and 4 don't have any free binding sites.

The equations for the first ligand-receptor system are as follows:

$$\frac{dR_1}{dt} = -k_{1,on}R_1L - k'_{1,on}R_1L_1 + k_{1,off}C_1 - k_{1,t}R_1 + Q_r \tag{22}$$

$$\frac{dC_1}{dt} = k_{1,on}R_1L + k'_{1,on}R_1L_1 - k_{1,off}C_1 - k_{1,e}C_1 \tag{23}$$

$$\frac{dR_2}{dt} = -k_{2,on}R_2L - k'_{2,on}R_2L_2 + k_{2,off}C_2 - k_{2,t}R_2 + Q_r \tag{24}$$

$$\frac{dC_2}{dt} = k_{2,on}R_2L + k'_{2,on}R_2L_2 - k_{2,off}C_2 - k_{2,e}C_2 \tag{25}$$

$$\frac{dL}{dt} = \frac{1}{N_{Av}V}(k_{1,off}C_1 - k_{1,on}R_1L + k_{2,off}C_2 - k_{2,on}R_2L) \tag{26}$$

$$L_1 = \frac{C_2'}{N_{Av}V_0} = \frac{3C_2'}{4\pi} \frac{1}{(r+a)^3 - r^3} \tag{27}$$

$$L_2 = \frac{C_1'}{N_{Av}V_0} = \frac{3C_1'}{4\pi} \frac{1}{(r+a)^3 - r^3} \tag{28}$$

with L being the total concentration of ligand. $C_{O1}$ and $C_{O2}$ are the number of receptors that are linked only to one of the ligands i.e., the ones that contribute to increase the local concentration of the other receptor. These values can be calculated as follows. In this case $a_{1;2} = a_{2;1} = a$ $$\frac{dC_1'}{dt} = k_{1,on}R_1L - k_{1,off}C_1' - k_{2,e}C_1' \tag{29}$$

$$\frac{dC_2'}{dt} = k_{2,on}R_2L - k_{2,off}C_1' - k_{2,e}C_1' \tag{30}$$

(31)

Figure 17:
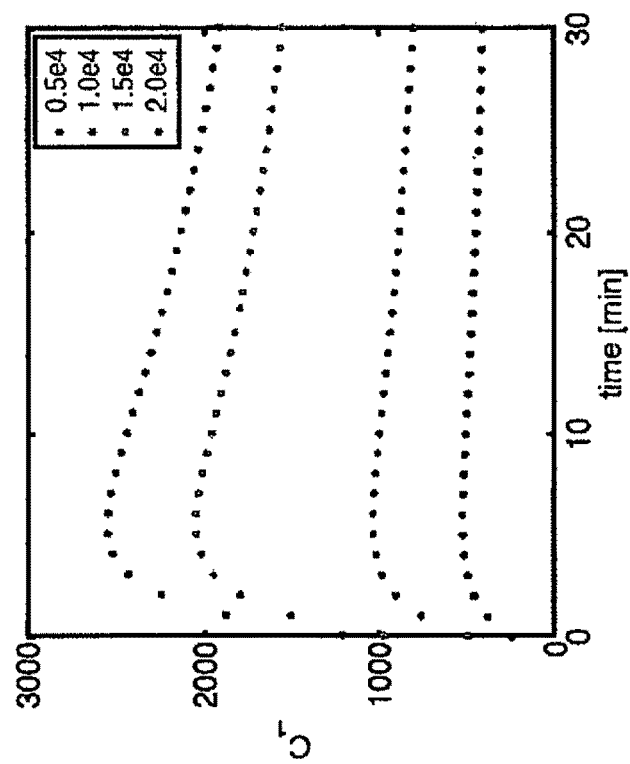
FIG. 17 shows a plot of the $C_1$ concentration in time, for different initial values of total $R_1$.

FIG. 17 represents the concentration of complex ligand-receptor 1 in the surface of the cell, for different values of total number of receptors $R_1$.

The equations for the second receptor are equivalent to the first one, but with an additional term which accounts for the ligand concentration that the receptor sees from the first ligand-receptor complex.

The effective ligand concentration that the second receptor sees depends on the amount of complex ligand-receptor 1 $C_1$ in the surface of the cell at any time. An additional term is added in the second set of equations, which account for the local concentration of ligand close to the cell surface. This concentration is calculated in Equation 27 assuming that the molecules are distributed in a volume gasket $V_0$ on the cell surface of height the length of the linker. This assumption is justified by the fact that diffusion of the receptors is very fast compared with the internalization times of the receptors.

The value of $k_{0on;2}$ needs to be scaled taking into account the fact that the reaction with the ligand linked to a surface is constrained by structural and geometric aspects of the systems. The fact that receptor diameter is comparable with linker size and that different heights of receptors in the outer part of the cell membrane has to be introduced into the problem.

While the dissociation rates for each binding reaction $k_{1;off}$, $k_{2;off}$ are equivalent in reaction 1 and 3, and in reaction 2 and 4, the same is not true for the affinity rates. Reactions 3 and 4 occur now between molecules diffusing in a two-dimensional space, with one of them freely moving in three dimensions while attached to the cell surface receptor through one binding site.

This special configuration induces as set constrains that reduce and modulate the affinity rates $k_{1;on}$ and $k_{2;on}$. First of all, reaction between two molecules in a two dimensional surface is modulated by diffusion rate.

$$k'_{1,on} = \left( \frac{1}{k_{1,on}} + \frac{1}{k_{1,diff}} \right)^{-1} \tag{10}$$

where the diffusion rate $k_{diff}$ (expressed in the appropriate units of $M_{-1min-1}$) for two-dimensional collision is calculated based on physical considerations as follows:

$$k_{1,diff} = \frac{2\pi D_1}{\ln(b_1/a)} N_{Av} l_1 \quad (11)$$

$D_1$ and $l_1$ are the diffusion coefficient and the height of the receptor $R_1$, correspondingly.

Parameter $b_1$ is the average distance between free receptors in the cell, calculated considering homogeneous distribution of receptors on the cell, and calculated as follows:

$$b = \sqrt{\frac{4r^2}{R}} \quad (12)$$

The rest of the reactions account for the trafficking of the receptor-ligand complexes inside the cell. Reaction 5 and Reaction 6 account for the internalization of the signaling complexes and receptors, respectively, while reaction 7 accounts for the constant production of fresh receptors.

Chimeras are fusions of usually two or more ligands that target different extracellular receptors. Chimeras have been successfully tested experimentally for targeting selectively cells with different receptor concentration in their surface. Experimental results described herein demonstrate that the combination of chimera design with ligand mutation successfully increases selectivity in interferon targeting in cells overexpressing EGFR.

The fact that the ligand spends time in the regions where it can not react with its receptors will clearly reduce the reaction rate. These aspects were introduced by defining a new reaction rate in the following way.

$$k'_{on,1,2} = k_{on,1} \frac{V'}{V} \approx k_{on,1} \frac{3h_1}{4} \frac{(a^2 - a_{0,1,2}^2)}{a^3} \quad (32)$$

$$k'_{on,2,1} = k_{on,2} \frac{V'}{V} \approx k_{on,2} \frac{3h_2}{4} \frac{(a^2 - a_{0,2,1}^2)}{a^3} \quad (33)$$

For the numerical analysis, the parameter values listed in Table 3 were used, unless specified. The parameters correspond to measured values of the wild type EGFR and wild type IFN-R in Hela cells. The advantage is that experimental data is already available to validate the model predictions.

Figure 18:
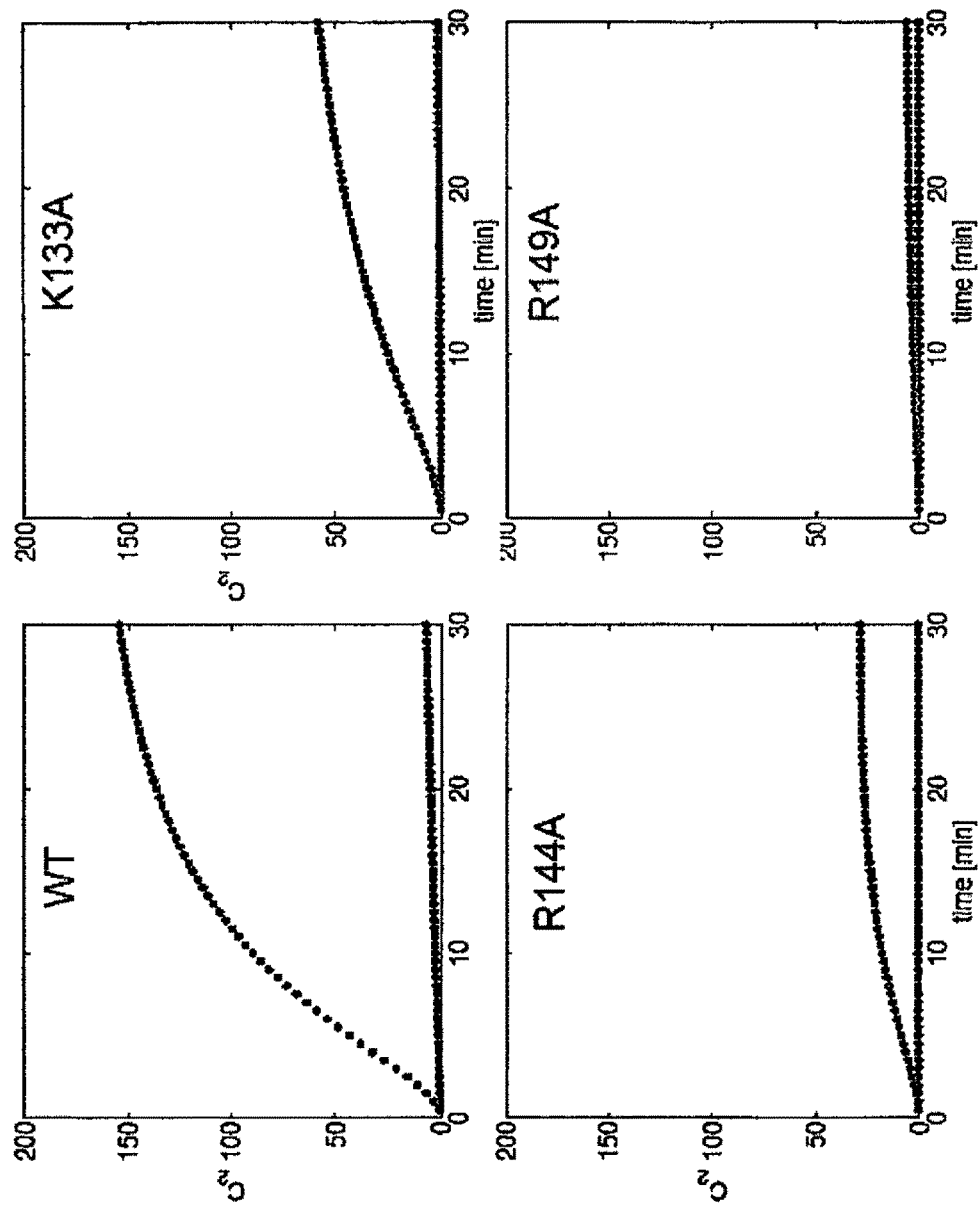
FIG. 18 shows plots of $C_2$ over time for different IF mutants (lower darker colored dots correspond to IF, and upper lighter colored dots correspond to chimeric protein)
Figure 19:
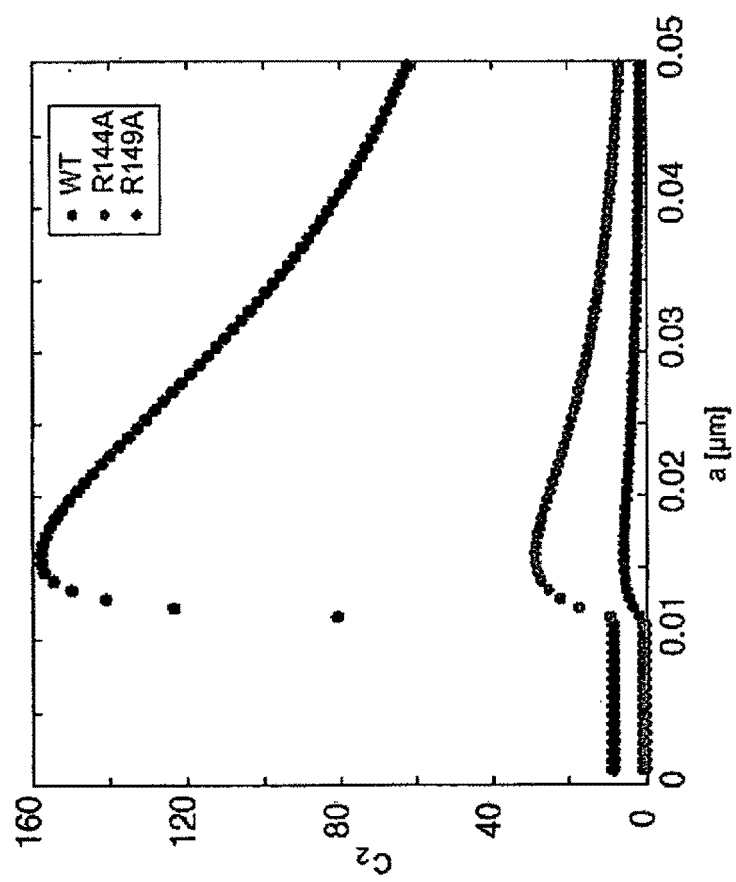
FIG. 19 shows a plot of $C_2$ at 30 min versus linker length for different IFN mutants.

To test the model predictions, reproduction was attempted of experimental observations, where different chimeras where designed with various mutants of a IF1 ligand. The different mutant designs were shown to have increased selectivity. The dependence on the total amount of $C_2$ for various interferon mutants, which exhibit different affinities with the IR, was analyzed. The goal was to test the selectivity of the chimeric protein among cells with higher EGFR expression levels. Results are shown in FIG. 18.

TABLE 3 numerical kinetic and physical parameters

| Parameter | Value |
|---|---|
| $R_{1,T}$ | $2 \times 10^4$ |
| $k_{1,off}$ | 0.24 min$^{-1}$ |

TABLE 3-continued numerical kinetic and physical parameters

| Parameter | Value |
|---|---|
| $k_{1,e}$ | 0.15 nM$^{-1}$ |
| $k_{1,D}$ | 2.47 nM |
| $h_1$ | 0.005 μm |
| $a_{0,1}$ | 0.01 μm |
| $l_1$ | lhjfldf |
| $R_{2,T}$ | $2 \times 10^2$ |
| $k_{2,off}$WT | 0.011 min$^{-1}$ |
| $k_{2,D}$WT | 3.7 nM |
| $k_{2,off}$K133A | 0.018 min$^{-1}$ |
| $k_{2,D}$K133A | 26 nM |
| $k_{2,off}$K144A | 0.073 min$^{-1}$ |
| $k_{2,D}$K144A | 120 nM |
| $k_{2,off}$K149A | 0.043 min$^{-1}$ |
| $k_{2,D}$K149A | 538 nM |
| $k_{2,e}$ | 0 ???? nM$^{-1}$ |
| $h_2$ | 0.005 μm |
| $a_{0,2}$ | 0.01 μm |
| $l_2$ | lhjfldf |
| $L_0$ | 0.5 nM |
| a | $125 \times 10^{-4}$ μm |
| D | 5.1 μm s$^{-1}$ |
| r | 8.5 μm |

In all cases, the number of IF receptors is higher in the case of a chimeric protein, due to the concentration of chimera localized in the surface of the cell. These results are in good qualitative agreement with the experimental results. Selectivity of the mutants depends, among other parameters, on the number of IF receptors necessary to induce apoptotic signaling in the cell. Signaling from the IF pathway can be measured to scale the numerical values obtained from the simulations.

It is reasonable to assume that for a relatively small number of active IF receptors in the cell, the pathway is saturated. Based on an analysis of the experimental data of the wild type IF without linker at a concentration of 0.5 nM, the pathway is saturated already or close to saturation. If this information is compared with the model results presented herein, it turns out that the pathway is close to saturation when the number of total active IF receptors at t=30 min is around 7. From here, selectivity occurs for active IF receptors below this value. On the other hand, experimentally measured signal is negligible in the case of mutant R144A at concentration 0.5 nM. In this case the model predicts a number of IFN receptors at time t=30 min of $C_2$=0.69.

These values can be used to scale the model from number of active IF receptors with actual signal measured in the cell.

4. Third Case Scenario: Optimal Linker Size

The model can be used to calculate the optimal linker size depending on the properties of the system (e.g., the number of receptors, ligand receptor affinity, structure of the membrane receptors, etc.). As a numerical example, the number of IFN receptors active for different linker sizes was calculated for the different mutants. The linker length dependence at high linker sizes reduces because the local concentration of chimera reduces with the length of the linker. At low values, the dependence is governed by the physical characteristics of the receptors, $(a_0,h)$.

5. Appendix A: Diffusion Time Versus Internalization Time

One of the additional issues in the linker length design concerns the time spent by receptor 1 to find the complex $C_1$ in the cell membrane. This time is dependent on the diffusion coefficient of the membrane receptors, as well as the linker length and the average distance between the two receptors.

To estimate this time, the equation for two dimensional diffusion was used. The average distance between two receptors, $b_{i,j}$, depends on the concentration and distribution of receptors i and j on the cell surface. To calculate this distance, it is assumed that the cell has a spherical shape, and that receptors are evenly distributed through the whole cell surface.

$$\tau = \frac{b^2}{2D} \log\left(\frac{b}{2a}\right) \quad (34)$$

Figure 20:
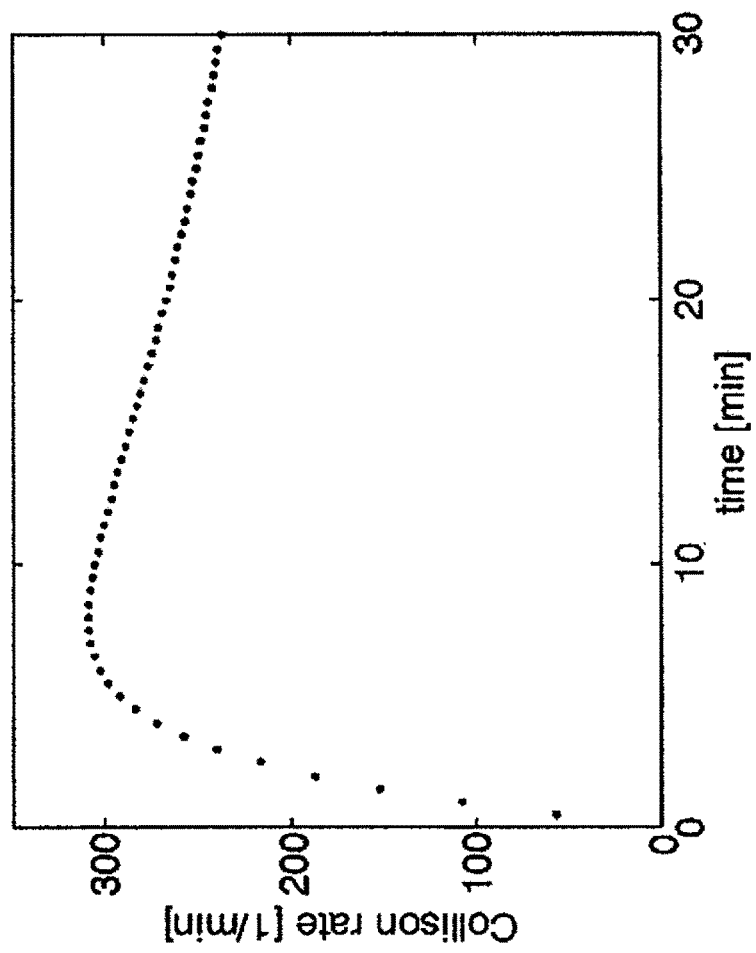
FIG. 20 shows a time plot of an embodiment of the collision rate.
Figure 21:
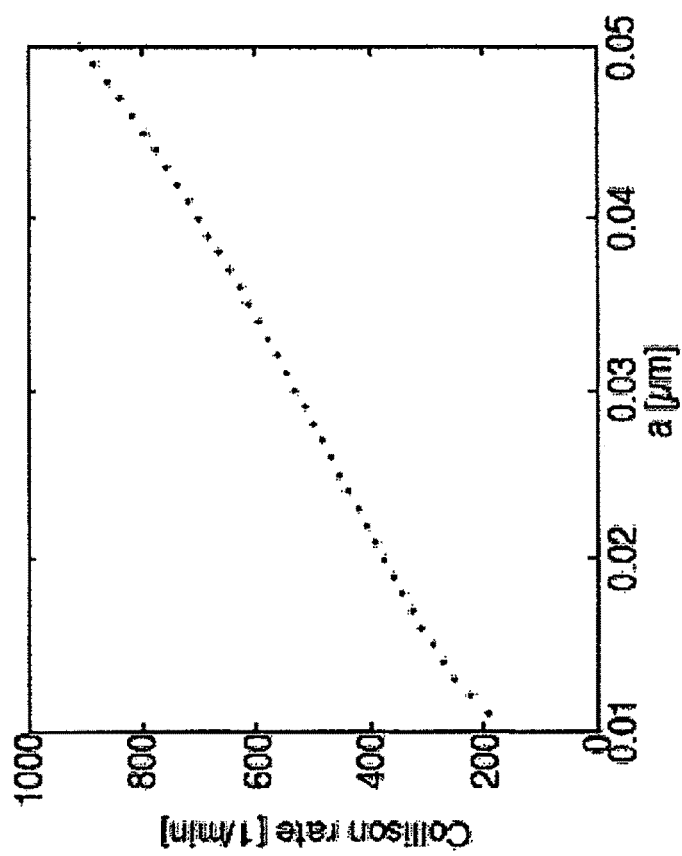
FIG. 21 shows a plot of an embodiment of collision rate versus linker size.

In this equation, 2a is the effective target size and D is the diffusion coefficient (assuming both receptor has the same diffusion rate). The distance between the target and the empty receptor depends on the concentration of the complex $C_1$, which is time dependent. The collision rate is given by $$b = \frac{C_1}{2} \frac{1}{4\pi R_{cell}^2} \quad (35)$$

where r is the average cell radius. The collision rate was computed (inverse of the collision time) for this case study (with Hela cells, EGFR and IF). FIG. 20 is a time plot of the rate of collision.

It should be appreciated that the analysis described herein may be used to design optimal linker lengths for chimeric activators described herein (where the chimeric activators are designed to bind to cell surface receptors, and wherein one of the binding elements may be mutated to have a lower binding affinity for its receptor). However, aspects of the invention also may be used to optimize linker lengths for other chimeric molecules where two components that bind to different binding sites are connected via a linker.

Example 12

Chimeric Activators for Treating Asthma

In some embodiments, chimeric activators can be designed to target cells associated with diseases such as asthma. In one example a chimeric activator can be designed to kill or inactivate B cells that produce IgE. In some embodiments, an IgE receptor may be used as a targeting element and FasL may be used as an activity element.

Other Embodiments

It will be clear that the invention may be practiced other than as particularly described in the foregoing description and examples. In some embodiments, methods of the invention include modifying, assaying, and/or optimizing one or more of the targeting or activity elements and/or the linker. Numerous modifications and variations of the present invention are possible in light of the above teachings and, therefore, are within the scope of the claims. Preferred features of each aspect of the invention are as for each of the other aspects mutatis mutandis. The documents including patents, patent applications, journal articles, abstracts, laboratory manuals, books, or other disclosures mentioned herein are hereby incorporated by reference in their entirety. In the event of conflict, the disclosure of present application controls, other than in the event of clear error. Further, the hard copy of the sequence listing submitted herewith and the corresponding computer readable form are both incorporated herein by reference in their entireties.

The invention claimed is:

1. A recombinant protein comprising a first element comprising a variant of interferon alpha (IFNa) comprising at least one amino acid substitution mutation that reduces the binding affinity of the variant by at least 10-fold relative to IFNα, and wherein the variant of IFNa is a K133A, R144A, or R149A variant of IFNα;

a second element comprising Epidermal Growth Factor (EGF), Cell Differentiation 4 (CD4), or an anti-EGFRde(2-7); and a linker that connects the first and second elements.

2. The recombinant protein of claim 1, wherein the linker is 35 amino acids long.

3. The recombinant protein of claim 1, wherein the linker consists of glycine and serine residues.

4. The recombinant protein of claim 1, wherein the variant of IFNα comprises at least one amino acid substitution mutation that reduces the binding affinity of the variant of IFNα for its naturally-occurring cell surface receptors by at least 200-fold relative to the wild-type of IFNα protein.

5. The recombinant protein of claim 1, wherein the second element comprises an EGF protein.

6. The recombinant protein of claim 1, wherein the variant of IFNα comprises a R144A mutation or a R149A mutation; and the second element comprises an EGF protein.

7. The recombinant protein of claim 1, wherein the recombinant protein binds to a cancer cell and mediates cell death or a reduction or absence of cell proliferation of the cancer cell; and the variant of IFNα alone will not bind to the cancer cell and mediate cell death or a reduction or absence of cell proliferation of the cancer cell.

8. The recombinant protein of claim 1, wherein the linker is between 25 and 70 amino acids long.

9. The recombinant protein of claim 1, wherein the linker is flexible.

* * * * *

SEQUENCE LISTING

```
<160> NUMBER OF SEQ ID NOS: 40

<210> SEQ ID NO 1
<211> LENGTH: 825
<212> TYPE: DNA
<213> ORGANISM: Artificial Sequence
<220> FEATURE:
<223> OTHER INFORMATION: Synthetic Polynucleotide

<400> SEQUENCE: 1
tgtgatttgc cacaaactca ttctttgggt tccagaagaa ctctgatgtt gctggctcaa      60
atgagaaaga tttccttgtt ctcctgtttg aaagatagac atgacttcgg ttttccacaa     120
gaagaatttg gtaatcaatt ccagaaagcc gagaccattc ctgttttgca tgagatgatc     180
caacagatct tcaacttgtt ttctactaag gactcttccg cagcttggga tgaaaccttg     240
ctggataagt tctacactga attgtaccag caattgaacg atttggaagc ttgtgtcatt     300
caaggagttg gagtcactga gactccattg atgaaggagg attctatttt ggctgtcaga     360
aagtactttc aaagaatcac cttgtacttg aaggagaaga aatactctcc atgtgcctgg     420
gaagtcgtta gagcagaaat tatgagatct ttctctttgt ccaccaacct gcaagaatcc     480
ttgagatcta aggaaggtgg aggaggttcc ggaggtggag gttccggtgg aggaggttcc     540
ggtggaggag gttccggagg aggtggatcc ggtggtggtg gatctggagg tggaggatcc     600
aactctgatt ctgagtgtcc attgtctcac gatggttact gtctgcatga tggtgtatgc     660
atgtacattg aagcattgga caagtacgct tgcaattgtg ttgtcggata cattggagag     720
```

```
agatgtcaat acagagattt gaagtggtgg gagttgcgtc tagaacaaaa actcatctca    780
gaagaggatc tgaatagcgc cgtcgaccat catcatcatc atcat                    825
```

<210> SEQ ID NO 2
<211> LENGTH: 275
<212> TYPE: PRT
<213> ORGANISM: Artificial Sequence
<220> FEATURE:
<223> OTHER INFORMATION: Synthetic Polypeptide

<400> SEQUENCE: 2

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Gly Gly Gly Gly Ser Gly Gly Gly Gly Ser Gly
                165                 170                 175

Gly Gly Ser Gly Gly Gly Gly Ser Gly Gly Gly Gly Ser Gly Gly
            180                 185                 190

Gly Gly Ser Gly Gly Gly Gly Ser Asn Ser Asp Ser Glu Cys Pro Leu
        195                 200                 205

Ser His Asp Gly Tyr Cys Leu His Asp Gly Val Cys Met Tyr Ile Glu
    210                 215                 220

Ala Leu Asp Lys Tyr Ala Cys Asn Cys Val Val Gly Tyr Ile Gly Glu
225                 230                 235                 240

Arg Cys Gln Tyr Arg Asp Leu Lys Trp Trp Glu Leu Arg Leu Glu Gln
                245                 250                 255

Lys Leu Ile Ser Glu Glu Asp Leu Asn Ser Ala Val Asp His His
            260                 265                 270

His His His
        275
```

<210> SEQ ID NO 3
<211> LENGTH: 825
<212> TYPE: DNA
<213> ORGANISM: Artificial Sequence
<220> FEATURE:
<223> OTHER INFORMATION: Synthetic Polynucleotide

<400> SEQUENCE: 3

```
tgtgatttgc cacaaactca ttctttgggt tccagaagaa ctctgatgtt gctggctcaa    60
atgagaaaga tttccttgtt ctcctgtttg aaagatagac atgacttcgg ttttccacaa   120
gaagaatttg gtaatcaatt ccagaaagcc gagaccattc ctgttttgca tgagatgatc   180
caacagatct tcaacttgtt ttctactaag gactcttccg cagcttggga tgaaaccttg   240
ctggataagt tctacactga attgtaccag caattgaacg atttggaagc ttgtgtcatt   300
caaggagttg gagtcactga gactccattg atgaaggagg attctatttt ggctgtcaga   360
aagtactttc aaagaatcac cttgtacttg aaggaggcta atactctcc atgtgcctgg    420 gaagtcgtta gagcagaaat tatgagatct ttctctttgt ccaccaacct gcaagaatcc   480
ttgagatcta aggaaggtgg aggaggttcc ggaggtggag gttccggtgg aggaggttcc   540
ggtggaggag gttccggagg aggtggatcc ggtggtggtg gatctggagg tggaggatcc   600
aactctgatt ctgagtgtcc attgtctcac gatggttact gtctgcatga tggtgtatgc   660
atgtacattg aagcattgga caagtacgct tgcaattgtg ttgtcggata cattggagag   720
agatgtcaat acagagattt gaagtggtgg gagttgcgtc tagaacaaaa actcatctca   780
gaagaggatc tgaatagcgc cgtcgaccat catcatcatc atcat              825
```

<210> SEQ ID NO 4
<211> LENGTH: 275
<212> TYPE: PRT
<213> ORGANISM: Artificial Sequence
<220> FEATURE:
<223> OTHER INFORMATION: Synthetic Polypeptide
<400> SEQUENCE: 4

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Ala Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Gly Gly Gly Ser Gly Gly Gly Gly Ser Gly
                165                 170                 175

Gly Gly Gly Ser Gly Gly Gly Gly Ser Gly Gly Gly Gly Ser Gly Gly
            180                 185                 190

Gly Gly Ser Gly Gly Gly Gly Ser Asn Ser Asp Ser Glu Cys Pro Leu
        195                 200                 205

Ser His Asp Gly Tyr Cys Leu His Asp Gly Val Cys Met Tyr Ile Glu
    210                 215                 220
```

Ala Leu Asp Lys Tyr Ala Cys Asn Cys Val Gly Tyr Ile Gly Glu
225                 230                 235                 240

Arg Cys Gln Tyr Arg Asp Leu Lys Trp Trp Glu Leu Arg Leu Glu Gln
            245                 250                 255

Lys Leu Ile Ser Glu Glu Asp Leu Asn Ser Ala Val Asp His His
        260                 265                 270

His His His
    275

<210> SEQ ID NO 5
<211> LENGTH: 825
<212> TYPE: DNA
<213> ORGANISM: Artificial Sequence
<220> FEATURE:
<223> OTHER INFORMATION: Synthetic Polynucleotide

<400> SEQUENCE: 5

```
tgtgatttgc cacaaactca ttctttgggt tccagaagaa ctctgatgtt gctggctcaa     60
atgagaaaga tttccttgtt ctcctgtttg aaagatagac atgacttcgg ttttccacaa    120
gaagaatttg gtaatcaatt ccagaaagcc gagaccattc ctgttttgca tgagatgatc    180
caacagatct tcaacttgtt ttctactaag gactcttccg cagcttggga tgaaaccttg    240
ctggataagt tctacactga attgtaccag caattgaacg atttggaagc ttgtgtcatt    300
caaggagttg gagtcactga gactccattg atgaaggagg attctatttt ggctgtcaga    360
aagtactttc aaagaatcac cttgtacttg aaggagaaga atactctcc atgtgcctgg     420
gaagtcgttg ctgcagaaat tatgagatct ttctcttttgt ccaccaacct gcaagaatcc    480
ttgagatcta aggaaggtgg aggaggttcc ggaggtggag gttccggtgg aggaggttcc    540
ggtggaggag gttccggagg aggtggatcc ggtggtggtg gatctggagg tggaggatcc    600
aactctgatt ctgagtgtcc attgtctcac gatggttact gtctgcatga tggtgtatgc    660
atgtacattg aagcattgga caagtacgct tgcaattgtg ttgtcggata cattggagag    720
agatgtcaat acagagattt gaagtggtgg agttgcgtc tagaacaaaa actcatctca    780
gaagaggatc tgaatagcgc cgtcgaccat catcatcatc atcat                    825
```

<210> SEQ ID NO 6
<211> LENGTH: 275
<212> TYPE: PRT
<213> ORGANISM: Artificial Sequence
<220> FEATURE:
<223> OTHER INFORMATION: Synthetic Polypeptide

<400> SEQUENCE: 6

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Ala
    130                 135                 140

Ala Glu Ile Met Arg Ser Phe Ser Leu Ser Thr Asn Leu Gln Glu Ser
145                 150                 155                 160

Leu Arg Ser Lys Glu Gly Gly Gly Gly Gly Gly Gly Gly Ser Gly
                165                 170                 175

Gly Gly Gly Ser Gly Gly Gly Gly Ser Gly Gly Gly Gly Ser Gly Gly
            180                 185                 190

Gly Gly Ser Gly Gly Gly Gly Ser Asn Ser Asp Ser Glu Cys Pro Leu
        195                 200                 205

Ser His Asp Gly Tyr Cys Leu His Asp Gly Val Cys Met Tyr Ile Glu
    210                 215                 220

Ala Leu Asp Lys Tyr Ala Cys Asn Cys Val Val Gly Tyr Ile Gly Glu
225                 230                 235                 240

Arg Cys Gln Tyr Arg Asp Leu Lys Trp Trp Glu Leu Arg Leu Glu Gln
                245                 250                 255

Lys Leu Ile Ser Glu Glu Asp Leu Asn Ser Ala Val Asp His His His
            260                 265                 270

His His His
    275

<210> SEQ ID NO 7
<211> LENGTH: 825
<212> TYPE: DNA
<213> ORGANISM: Artificial Sequence
<220> FEATURE:
<223> OTHER INFORMATION: Synthetic Polynucleotide

<400> SEQUENCE: 7
tgtgatttgc cacaaactca ttctttgggt tccagaagaa ctctgatgtt gctggctcaa      60
atgagaaaga tttccttgtt ctcctgtttg aaagatagac atgacttcgg ttttccacaa     120
gaagaatttg gtaatcaatt ccagaaagcc gagaccattc ctgttttgca tgagatgatc     180
caacagatct tcaacttgtt ttctactaag gactcttccg cagcttggga tgaaaccttg     240
ctggataagt tctacactga attgtaccag caattgaacg atttggaagc ttgtgtcatt     300
caaggagttg gagtcactga gactccattg atgaaggagg attctatttt ggctgtcaga     360
aagtactttc aaagaatcac cttgtacttg aaggagaaga atactctcc atgtgcctgg     420 gaagtcgtta gcagaaat tatggcttct ttctctttgt ccaccaacct gcaagaatcc     480
ttgagatcta aggaaggtgg aggaggttcc ggaggtggag gttccggtgg aggaggttcc     540
ggtggaggag gttccggagg aggtggatcc ggtggtggtg gatctggagg tggaggatcc     600
aactctgatt ctgagtgtcc attgtctcac gatggttact gtctgcatga tggtgtatgc     660
atgtacattg aagcattgga caagtacgct tgcaattgtg ttgtcggata cattggagag     720
agatgtcaat acagagattt gaagtggtgg gagttgcgtc tagaacaaaa actcatctca     780
gaagaggatc tgaatagcgc cgtcgaccat catcatcatc atcat                     825

<210> SEQ ID NO 8
<211> LENGTH: 275
<212> TYPE: PRT
<213> ORGANISM: Artificial Sequence
<220> FEATURE:
<223> OTHER INFORMATION: Synthetic Polypeptide

<400> SEQUENCE: 8

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Ala Ser Phe Ser Leu Ser Thr Asn Leu Gln Glu Ser
145                 150                 155                 160

Leu Arg Ser Lys Glu Gly Gly Gly Ser Gly Gly Gly Ser Gly
                165                 170                 175

Gly Gly Ser Gly Gly Gly Ser Gly Gly Gly Ser Gly Gly
            180                 185                 190

Gly Gly Ser Gly Gly Gly Ser Asn Ser Asp Ser Cys Pro Leu
        195                 200                 205

Ser His Asp Gly Tyr Cys Leu His Asp Gly Val Cys Met Tyr Ile Glu
    210                 215                 220

Ala Leu Asp Lys Tyr Ala Cys Asn Cys Val Val Gly Tyr Ile Gly Glu
225                 230                 235                 240

Arg Cys Gln Tyr Arg Asp Leu Lys Trp Trp Glu Leu Arg Leu Glu Gln
                245                 250                 255

Lys Leu Ile Ser Glu Glu Asp Leu Asn Ser Ala Val Asp His His
            260                 265                 270

His His His
        275

<210> SEQ ID NO 9
<211> LENGTH: 564
<212> TYPE: DNA
<213> ORGANISM: Artificial Sequence
<220> FEATURE:
<223> OTHER INFORMATION: Synthetic Polynucleotide

<400> SEQUENCE: 9
tgtgatttgc cacaaactca ttctttgggt tccagaagaa ctctgatgtt gctggctcaa      60
atgagaaaga tttccttgtt ctcctgtttg aaagatagac atgacttcgg ttttccacaa    120
gaagaatttg gtaatcaatt ccagaaagcc gagaccattc ctgttttgca tgagatgatc    180
caacagatct tcaacttgtt ttctactaag gactcttccg cagcttggga tgaaaccttg    240
ctggataagt tctacactga attgtaccag caattgaacg atttggaagc ttgtgtcatt    300

```
caaggagttg gagtcactga gactccattg atgaaggagg attctatttt ggctgtcaga    360
aagtactttc aaagaatcac cttgtacttg aaggagaaga atactctcc atgtgcctgg    420 gaagtcgtta gagcagaaat tatgagatct ttctctttgt ccaccaacct gcaagaatcc    480
ttgagatcta aggaaggtct agaacaaaaa ctcatctcag aagaggatct gaatagcgcc    540
gtcgaccatc atcatcatca tcat                                          564
```

<210> SEQ ID NO 10
<211> LENGTH: 188
<212> TYPE: PRT
<213> ORGANISM: Artificial Sequence
<220> FEATURE:
<223> OTHER INFORMATION: Synthetic Polypeptide

<400> SEQUENCE: 10

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Gly Leu Glu Gln Lys Leu Ile Ser Glu Glu Asp
                165                 170                 175

Leu Asn Ser Ala Val Asp His His His His His
            180                 185
```

<210> SEQ ID NO 11
<211> LENGTH: 564
<212> TYPE: DNA
<213> ORGANISM: Artificial Sequence
<220> FEATURE:
<223> OTHER INFORMATION: Synthetic Polynucleotide

<400> SEQUENCE: 11

```
tgtgatttgc cacaaactca ttctttgggt tccagaagaa ctctgatgtt gctggctcaa    60
atgagaaaga tttccttgtt ctcctgtttg aaagatagac atgacttcgg ttttccacaa    120
gaagaatttg gtaatcaatt ccagaaagcc gagaccattc ctgttttgca tgagatgatc    180
caacagatct tcaacttgtt ttctactaag gactcttccg cagcttggga tgaaaccttg    240
ctggataagt tctacactga attgtaccag caattgaacg atttggaagc ttgtgtcatt    300
caaggagttg gagtcactga gactccattg atgaaggagg attctatttt ggctgtcaga    360
aagtactttc aaagaatcac cttgtacttg aaggaggcta aatactctcc atgtgcctgg    420
```

```
gaagtcgtta gagcagaaat tatgagatct ttctctttgt ccaccaacct gcaagaatcc    480
ttgagatcta aggaaggtct agaacaaaaa ctcatctcag agaggatct gaatagcgcc     540 gtcgaccatc atcatcatca tcat                                            564
```

<210> SEQ ID NO 12
<211> LENGTH: 188
<212> TYPE: PRT
<213> ORGANISM: Artificial Sequence
<220> FEATURE:
<223> OTHER INFORMATION: Synthetic Polypeptide

<400> SEQUENCE: 12

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Ala Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Gly Leu Glu Gln Lys Leu Ile Ser Glu Glu Asp
                165                 170                 175

Leu Asn Ser Ala Val Asp His His His His His
            180                 185
```

<210> SEQ ID NO 13
<211> LENGTH: 564
<212> TYPE: DNA
<213> ORGANISM: Artificial Sequence
<220> FEATURE:
<223> OTHER INFORMATION: Synthetic Polynucleotide

<400> SEQUENCE: 13

```
tgtgatttgc cacaaactca ttctttgggt tccagaagaa ctctgatgtt gctggctcaa    60
atgagaaaga tttccttgtt ctcctgtttg aaagatagac atgacttcgg ttttccacaa   120
gaagaatttg gtaatcaatt ccagaaagcc gagaccattc ctgttttgca tgagatgatc   180
caacagatct tcaacttgtt ttctactaag gactcttccg cagcttggga tgaaaccttg   240
ctggataagt tctacactga attgtaccag caattgaacg atttggaagc ttgtgtcatt   300
caaggagttg gagtcactga gactccattg atgaaggagg attctatttt ggctgtcaga   360
aagtactttc aaagaatcac cttgtacttg aaggagaaga aatactctcc atgtgcctgg   420
gaagtcgttg ctgcagaaat tatgagatct ttctctttgt ccaccaacct gcaagaatcc   480
```

```
ttgagatcta aggaaggtct agaacaaaaa ctcatctcag aagaggatct gaatagcgcc      540
gtcgaccatc atcatcatca tcat                                            564
```

```
<210> SEQ ID NO 14
<211> LENGTH: 188
<212> TYPE: PRT
<213> ORGANISM: Artificial Sequence
<220> FEATURE:
<223> OTHER INFORMATION: Synthetic Polypeptide

<400> SEQUENCE: 14
```

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Ala
    130                 135                 140

Ala Glu Ile Met Arg Ser Phe Ser Leu Ser Thr Asn Leu Gln Glu Ser
145                 150                 155                 160

Leu Arg Ser Lys Glu Gly Leu Glu Gln Lys Leu Ile Ser Glu Glu Asp
                165                 170                 175

Leu Asn Ser Ala Val Asp His His His His His
            180                 185

```
<210> SEQ ID NO 15
<211> LENGTH: 564
<212> TYPE: DNA
<213> ORGANISM: Artificial Sequence
<220> FEATURE:
<223> OTHER INFORMATION: Synthetic Polynucleotide

<400> SEQUENCE: 15
```

```
tgtgatttgc cacaaactca ttctttgggt tccagaagaa ctctgatgtt gctggctcaa       60
atgagaaaga tttccttgtt ctcctgtttg aaagatagac atgacttcgg ttttccacaa      120
gaagaatttg gtaatcaatt ccagaaagcc gagaccattc ctgttttgca tgagatgatc      180
caacagatct tcaacttgtt ttctactaag gactcttccg cagcttggga tgaaaccttg      240
ctggataagt tctacactga attgtaccag caattgaacg atttggaagc ttgtgtcatt      300
caaggagttg gagtcactga gactccattg atgaaggagg attctatttt ggctgtcaga      360
aagtactttc aaagaatcac cttgtacttg aaggagaaga atactctcc atgtgcctgg      420 gaagtcgtta gagcagaaat tatggcttct ttctctttgt ccaccaacct gcaagaatcc      480
ttgagatcta aggaaggtct agaacaaaaa ctcatctcag aagaggatct gaatagcgcc      540
gtcgaccatc atcatcatca tcat                                            564
```

<210> SEQ ID NO 16
<211> LENGTH: 188
<212> TYPE: PRT
<213> ORGANISM: Artificial Sequence
<220> FEATURE:
<223> OTHER INFORMATION: Synthetic Polypeptide

<400> SEQUENCE: 16

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Ala Ser Phe Ser Leu Ser Thr Asn Leu Gln Glu Ser
145                 150                 155                 160

Leu Arg Ser Lys Glu Gly Leu Glu Gln Lys Leu Ile Ser Glu Glu Asp
                165                 170                 175

Leu Asn Ser Ala Val Asp His His His His His
            180                 185
```

<210> SEQ ID NO 17
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 17

```
Glu Gln Lys Leu Ile Ser Glu Glu Asp Leu
1               5                   10
```

<210> SEQ ID NO 18
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 18

```
Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45
```

Ala Ser Ile Ser Thr Gly Gly Tyr Asn Thr Tyr Tyr Ser Asp Asn Val
            50                  55                  60

Lys Gly Arg Phe Thr Ile Ser Arg Glu Asn Ala Lys Asn Thr Leu Tyr
 65                  70                  75                  80

Leu Gln Met Ser Ser Leu Lys Ser Glu Asp Thr Ala Leu Tyr Tyr Cys
                 85                  90                  95

Thr Arg Gly Tyr Ser Pro Tyr Ser Tyr Ala Met Asp Tyr Trp Gly Gln
            100                 105                 110

Gly Thr Thr Val Thr Val Ser
        115

<210> SEQ ID NO 19
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 19

Ser Ser Gly Gly Gly Ser Gly Gly Gly Ser Gly Gly Gly Gly Ser
 1               5                  10                  15

<210> SEQ ID NO 20
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 20

Asp Ile Glu Leu Thr Gln Ser Pro Ala Ser Leu Ser Val Ala Thr Gly
 1               5                  10                  15

Glu Lys Val Thr Ile Arg Cys Met Thr Ser Thr Asp Ile Asp Asp Asp
                20                  25                  30

Met Asn Trp Tyr Gln Gln Lys Pro Gly Glu Pro Pro Lys Phe Leu Ile
             35                  40                  45

Ser Glu Gly Asn Thr Leu Arg Pro Gly Val Pro Ser Arg Phe Ser Ser
 50                  55                  60

Ser Gly Thr Gly Thr Asp Phe Val Phe Thr Ile Glu Asn Thr Leu Ser
 65                  70                  75                  80

Glu Asp Val Gly Asp Tyr Tyr Cys Leu Gln Ser Trp Asn Val Pro Leu
                 85                  90                  95

Thr Phe Gly Asp Gly Thr Lys Leu Glu Ile Lys
            100                 105

<210> SEQ ID NO 21
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 21

Gly Gly Gly Gly Ser Gly Gly Ser Ser Gly Gly Ser Ser Ser
 1               5                  10                  15

Gly Gly Gly Gly Ser Gly Gly Gly Ser Ser Gly Gly Ser Gly
                20                  25                  30

Gly Gly Ser
        35

```
<210> SEQ ID NO 22
<211> LENGTH: 167
<212> TYPE: PRT
<213> ORGANISM: Artificial Sequence
<220> FEATURE:
<223> OTHER INFORMATION: Synthetic Polypeptide

<400> SEQUENCE: 22

Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

Phe Leu Ser Asn Leu His Leu Arg Asn Gly Glu Leu Val Ile His Glu
    50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
                85                  90                  95

Tyr Lys Tyr Thr Ser Tyr Pro Ala Pro Ile Leu Leu Met Lys Ser Ala
            100                 105                 110

Arg Asn Ser Cys Trp Ser Lys Asp Ala Glu Tyr Gly Leu Tyr Ser Ile
        115                 120                 125

Tyr Gln Gly Gly Ile Phe Glu Leu Lys Glu Asn Asp Arg Ile Phe Val
    130                 135                 140

Ser Val Thr Asn Glu His Leu Ile Asp Met Asp His Glu Ala Ser Phe
145                 150                 155                 160

Phe Gly Ala Phe Leu Val Gly
                165

<210> SEQ ID NO 23
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 23

Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Pro Tyr Tyr Ala Met Asp Tyr Trp Gly Gln
            100                 105                 110

Gly Thr Thr Val Thr Val Ser Ser Gly Gly Ser Gly Gly Gly
        115                 120                 125

Gly Ser Gly Gly Gly Gly Ser Asp Ile Glu Leu Thr Gln Ser Pro Ala
    130                 135                 140
```

Ser Leu Ser Val Ala Thr Gly Glu Lys Val Thr Ile Arg Cys Met Thr
145                 150                 155                 160

Ser Thr Asp Ile Asp Asp Met Asn Trp Tyr Gln Gln Lys Pro Gly
            165                 170                 175

Glu Pro Pro Lys Phe Leu Ile Ser Glu Gly Asn Thr Leu Arg Pro Gly
        180                 185                 190

Val Pro Ser Arg Phe Ser Ser Gly Thr Gly Thr Asp Phe Val Phe
        195                 200                 205

Thr Ile Glu Asn Thr Leu Ser Glu Asp Val Gly Asp Tyr Tyr Cys Leu
        210                 215                 220

Gln Ser Trp Asn Val Pro Leu Thr Phe Gly Asp Gly Thr Lys Leu Glu
225                 230                 235                 240

Ile Lys Gly Gly Gly Gly Ser Gly Gly Gly Ser Ser Gly Gly Ser
                245                 250                 255

Ser Ser Gly Gly Gly Ser Gly Gly Gly Ser Ser Gly Gly Gly
            260                 265                 270

Ser Gly Gly Gly Ser Arg Glu Arg Gly Pro Gln Arg Val Ala Ala His
        275                 280                 285

Ile Thr Gly Thr Arg Gly Arg Ser Asn Thr Leu Ser Ser Pro Asn Ser
290                 295                 300

Lys Asn Glu Lys Ala Leu Gly Arg Lys Ile Asn Ser Trp Glu Ser Ser
305                 310                 315                 320

Arg Ser Gly His Ser Phe Leu Ser Asn Leu His Leu Arg Asn Gly Glu
            325                 330                 335

Leu Val Ile His Glu Lys Gly Phe Tyr Tyr Ile Tyr Ser Gln Thr Tyr
            340                 345                 350

Phe Arg Phe Gln Glu Glu Ile Lys Glu Asn Thr Lys Asn Asp Lys Gln
        355                 360                 365

Met Val Gln Tyr Ile Tyr Lys Tyr Thr Ser Tyr Pro Ala Pro Ile Leu
370                 375                 380

Leu Met Lys Ser Ala Arg Asn Ser Cys Trp Ser Lys Asp Ala Glu Tyr
385                 390                 395                 400

Gly Leu Tyr Ser Ile Tyr Gln Gly Gly Ile Phe Glu Leu Lys Glu Asn
            405                 410                 415

Asp Arg Ile Phe Val Ser Val Thr Asn Glu His Leu Ile Asp Met Asp
        420                 425                 430

His Glu Ala Ser Phe Phe Gly Ala Phe Leu Val Gly
        435                 440

<210> SEQ ID NO 24
<211> LENGTH: 1332
<212> TYPE: DNA
<213> ORGANISM: Artificial Sequence
<220> FEATURE:
<223> OTHER INFORMATION: Synthetic Polynucleotide

<400> SEQUENCE: 24
caagttaagt tgcaacaatc cggtggtggt tggttaagc caggtgcttc tttgaagttg    60
tcttgtgtta cttctggttt tactttaga aagtttggta tgtcttgggt tagacaaact    120
tctgataaga gattggaatg ggttgcttct atttctactg gtggttacaa cacttactac    180
tctgataacg ttaagggtag atttactatt tccagagaga acgctaagaa cactttgtac    240
ttgcaaatgt cttctttgaa gtctgaagat actgctttgt actactgtac tagaggttac    300
tctccatact cttacgctat ggattactgg ggtcaaggta ctactgttac tgtttcttcc    360

| | |
|---|---|
| tccggtggag gttccggtgg tggaggatct ggtggtggtg gttctgatat tgagttgact | 420 |
| caatctccag cttctttgtc tgttgctact ggtgagaagg ttactattag atgtatgact | 480 |
| tctactgata ttgatgatga tatgaactgg taccaacaaa agccaggtga accaccaaag | 540 |
| tttttgattt ctgaaggtaa cactttgaga ccaggtgttc catccagatt ttcttcttct | 600 |
| ggtactggta ctgattttgt ttttactatt gagaacactt tgtctgaaga tgttggtgat | 660 |
| tactactgtt tgcaatcttg gaacgttcca ttgacttttg gtgatggtac taagttggag | 720 |
| attaagggag gaggtggttc cggtggtggt tcttccggag gtggttcttc ctctggaggt | 780 |
| ggtggttcag gtggaggtgg ttcctctgga ggtggttctg gtggaggttc cagagaaaga | 840 |
| ggtccacaaa gagttgctgc tcacattact ggtactagag gtagatctaa cactttgtct | 900 |
| tctccaaact ctaagaacga aaaggctttg gtagaaaaga ttaactcttg ggagtcttcc | 960 |
| agatctggtc attctttctt gtctaacttg catttgagaa acggtgaatt ggttattcat | 1020 |
| gagaagggtt tctactacat ttactctcaa acttacttta gatttcaaga agaaattaag | 1080 |
| gagaacacta agaacgataa gcaaatggtt caatacattt acaagtacac ttcttaccca | 1140 |
| gctccaattt tgttgatgaa gtctgctaga aactcttgtt ggtctaagga tgctgaatac | 1200 |
| ggtttgtact ctatttacca aggtggtatt ttcgaattga aggagaacga tagaattttc | 1260 |
| gtttctgtta ctaacgaaca tttgattgat atggatcacg aagcttcttt ctttggtgct | 1320 |
| tttttggttg gt | 1332 |

<210> SEQ ID NO 25
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Ser Lys Tyr Val Pro Lys Phe
    50                  55                  60

Gln Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
        115                 120

<210> SEQ ID NO 26
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 26

Ser Ser Ser Gly Gly Gly Ser Gly Gly Gly Gly Ser Gly Gly Gly Gly

<210> SEQ ID NO 27
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 27

Asp Ile Gln Leu Thr Gln Ser Pro Ser Leu Ser Ala Ser Val Gly
1               5                   10                  15

Asp Arg Val Thr Ile Thr Cys Arg Ala Gly Glu Ser Val Asp Ile Phe
                20                  25                  30

Gly Val Gly Phe Leu His Trp Tyr Gln Gln Lys Pro Gly Lys Ala Pro
            35                  40                  45

Lys Leu Leu Ile Tyr Arg Ala Ser Asn Leu Glu Ser Gly Val Pro Ser
50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Thr Asn
                85                  90                  95

Glu Asp Pro Tyr Thr Phe Gly Gln Gly Thr Lys Val Glu Ile Lys
            100                 105                 110

<210> SEQ ID NO 28
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 28

Gly Gly Gly Gly Ser Gly Gly Gly Ser Ser Gly Gly Gly Ser Ser Ser
1               5                   10                  15

Gly Gly Gly Gly Ser Gly Gly Gly Gly Ser Ser Gly Gly Gly Ser Gly
                20                  25                  30

Gly Gly Ser
        35

<210> SEQ ID NO 29
<211> LENGTH: 167
<212> TYPE: PRT
<213> ORGANISM: Artificial Sequence
<220> FEATURE:
<223> OTHER INFORMATION: Synthetic Polypeptide

<400> SEQUENCE: 29

Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
                20                  25                  30

Leu Gly Arg Lys Ile Asn Ser Trp Glu Ser Ser Arg Ser Gly His Ser
            35                  40                  45

Phe Leu Ser Asn Leu His Leu Arg Asn Gly Glu Leu Val Ile His Glu
        50                  55                  60

Lys Gly Phe Tyr Tyr Ile Tyr Ser Gln Thr Tyr Phe Arg Phe Gln Glu
65                  70                  75                  80

```
Glu Ile Lys Glu Asn Thr Lys Asn Asp Lys Gln Met Val Gln Tyr Ile
                85                  90                  95

Tyr Lys Tyr Thr Ser Tyr Pro Ala Pro Ile Leu Leu Met Lys Ser Ala
            100                 105                 110

Arg Asn Ser Cys Trp Ser Lys Asp Ala Glu Tyr Gly Leu Tyr Ser Ile
            115                 120                 125

Tyr Gln Gly Gly Ile Phe Glu Leu Lys Glu Asn Asp Arg Ile Phe Val
            130                 135                 140

Ser Val Thr Asn Glu His Leu Ile Asp Met Asp His Glu Ala Ser Phe
145                 150                 155                 160

Phe Gly Ala Phe Leu Val Gly
                165
```

<210> SEQ ID NO 30
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Met His Trp Val Arg Gln Ala Pro Gly Lys Gly Leu Glu Trp Val
            35                  40                  45

Ala Arg Ile Asp Pro Ala Asn Gly Asn Ser Lys Tyr Val Pro Lys Phe
        50                  55                  60

Gln Gly Arg Ala Thr Ile Ser Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ser Ser Gly Gly Gly Ser
            115                 120                 125

Gly Gly Gly Gly Ser Gly Gly Gly Ser Asp Ile Gln Leu Thr Gln
            130                 135                 140

Ser Pro Ser Ser Leu Ser Ala Ser Val Gly Asp Arg Val Thr Ile Thr
145                 150                 155                 160

Cys Arg Ala Gly Glu Ser Val Asp Ile Phe Gly Val Gly Phe Leu His
            165                 170                 175

Trp Tyr Gln Gln Lys Pro Gly Lys Ala Pro Lys Leu Leu Ile Tyr Arg
            180                 185                 190

Ala Ser Asn Leu Glu Ser Gly Val Pro Ser Arg Phe Ser Gly Ser Gly
            195                 200                 205

Ser Arg Thr Asp Phe Thr Leu Thr Ile Ser Ser Leu Gln Pro Glu Asp
            210                 215                 220

Phe Ala Thr Tyr Tyr Cys Gln Gln Thr Asn Glu Asp Pro Tyr Thr Phe
225                 230                 235                 240

Gly Gln Gly Thr Lys Val Glu Ile Lys Gly Gly Gly Ser Gly Gly
            245                 250                 255

Gly Ser Ser Gly Gly Gly Ser Ser Gly Gly Gly Ser Gly Gly
            260                 265                 270
```

```
Gly Gly Ser Gly Gly Gly Ser Gly Gly Ser Arg Glu Arg Gly
            275                 280                 285

Pro Gln Arg Val Ala Ala His Ile Thr Gly Thr Arg Gly Arg Ser Asn
    290                 295                 300

Thr Leu Ser Ser Pro Asn Ser Lys Asn Glu Lys Ala Leu Gly Arg Lys
305                 310                 315                 320

Ile Asn Ser Trp Glu Ser Ser Arg Ser Gly His Ser Phe Leu Ser Asn
                325                 330                 335

Leu His Leu Arg Asn Gly Glu Leu Val Ile His Glu Lys Gly Phe Tyr
            340                 345                 350

Tyr Ile Tyr Ser Gln Thr Tyr Phe Arg Phe Gln Glu Glu Ile Lys Glu
            355                 360                 365

Asn Thr Lys Asn Asp Lys Gln Met Val Gln Tyr Ile Tyr Lys Tyr Thr
    370                 375                 380

Ser Tyr Pro Ala Pro Ile Leu Leu Met Lys Ser Ala Arg Asn Ser Cys
385                 390                 395                 400

Trp Ser Lys Asp Ala Glu Tyr Gly Leu Tyr Ser Ile Tyr Gln Gly Gly
                405                 410                 415

Ile Phe Glu Leu Lys Glu Asn Asp Arg Ile Phe Val Ser Val Thr Asn
            420                 425                 430

Glu His Leu Ile Asp Met Asp His Glu Ala Ser Phe Phe Gly Ala Phe
            435                 440                 445

Leu Val Gly
    450

<210> SEQ ID NO 31
<211> LENGTH: 1353
<212> TYPE: DNA
<213> ORGANISM: Artificial Sequence
<220> FEATURE:
<223> OTHER INFORMATION: Synthetic Polynucleotide

<400> SEQUENCE: 31
gaagttcaat tggttgaatc tggaggtggt ttggttcaac caggtggttc tttgagattg      60
tcttgtgctg cttctggttt taacattaag gatacttaca tgcattgggt tagacaagct     120
ccaggtaagg gtttggaatg ggttgctaga attgatccag ctaacggtaa ctctaagtac     180
gttccaaagt ttcaaggtag agctactatt tctgctgata cttctaagaa cactgcttac     240
ttgcaaatga actctttgag agctgaagat actgctgttt actactgtgc tccatttggt     300
tactacgttt ctgattacgc tatggcttac tggggtcaag tactttggt tactgttct     360 tcctcctctt ctggtggagg ttctggaggt ggtggatctg gtggaggtgg ttctgatatt     420
caattgactc aatctccatc ttctttgtct gcttctgttg gtgatagagt tactattact     480
tgtagagctg gtgaatctgt tgatattttt ggtgttggtt ttttgcattg gtaccaacaa     540
aagccaggta aggctccaaa gttgttgatt tacagagctt ctaacttgga atctggtgtt     600
ccatccagat tttctggttc tggttccaga actgatttta ctttgactat tcttctttg     660 caaccagaag attttgctac ttactactgt caacaaacta cgaagatcc atacactttt     720 ggtcaaggta ctaaggttga aattaagggt ggaggaggt ctggtggtgg atcttccgga     780
ggtggttctt cctctggagg tggtggttca ggtggaggtg gttcctctgg aggtggttct     840
ggtggaggtt ccagagaaag aggtccacaa agagttgctg ctcacattac tggtactaga     900
ggtagatcta acactttgtc ttctccaaac tctaagaacg aaaaggcttt gggtagaaag     960
attaactctt gggagtcttc cagatctggt cattctttct tgtctaactt gcatttgaga    1020
```

```
aacggtgaat tggttattca tgagaagggt ttctactaca tttactctca aacttacttt    1080
agatttcaag aagaaattaa ggagaacact aagaacgata agcaaatggt tcaatacatt    1140
tacaagtaca cttcttaccc agctccaatt ttgttgatga agtctgctag aaactcttgt    1200
tggtctaagg atgctgaata cggtttgtac tctatttacc aaggtggtat tttcgaattg    1260
aaggagaacg atagaatttt cgtttctgtt actaacgaac atttgattga tatggatcac    1320
gaagcttctt tctttggtgc tttttttggtt ggt                                 1353
```

<210> SEQ ID NO 32
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 32

Ser Ser Thr Thr Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 33

Leu Ser Thr Thr Glu
1               5

<210> SEQ ID NO 34
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 34

Met Ala Gln Val Lys Leu Gln Gln Ser Gly Ala Glu Leu Val Lys Pro
1               5                   10                  15

Gly Ala Ser Val Lys Leu Ser Cys Lys Ala Ser Gly Tyr Thr Phe Asn
                20                  25                  30

Ser Tyr Phe Met His Trp Met Lys Gln Arg Pro Val Gln Gly Leu Glu
            35                  40                  45

Trp Ile Gly Met Ile Arg Pro Asn Gly Gly Thr Thr Asp Tyr Asn Glu
        50                  55                  60

Lys Phe Lys Asn Lys Ala Thr Leu Thr Val Asp Lys Ser Ser Asn Thr
65                  70                  75                  80

Ala Tyr Met Gln Leu Asn Ser Leu Thr Ser Gly Asp Ser Ala Val Tyr
                85                  90                  95

Tyr Cys Ala Arg Trp Glu Gly Ser Tyr Tyr Ala Leu Asp Tyr Trp Gly
            100                 105                 110

Gln Gly Thr Thr Val Thr Val Ser Ser
        115                 120

<210> SEQ ID NO 35
<211> LENGTH: 17
<212> TYPE: PRT
<213> ORGANISM: Artificial Sequence
<220> FEATURE:

<223> OTHER INFORMATION: Synthetic Polypeptide

<400> SEQUENCE: 35

Gly Gly Gly Gly Ser Gly Gly Gly Ser Ser Gly Gly Gly Gly Ser
1               5                   10                  15

Ser

<210> SEQ ID NO 36
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 36

Asp Ile Glu Leu Thr Gln Ser Pro Ala Ile Met Ser Ala Thr Leu Gly
1               5                   10                  15

Glu Lys Val Thr Met Thr Cys Arg Ala Ser Ser Asn Val Lys Tyr Met
                20                  25                  30

Tyr Trp Tyr Gln Gln Lys Ser Gly Ala Ser Pro Lys Leu Trp Ile Tyr
            35                  40                  45

Tyr Thr Ser Asn Leu Ala Ser Gly Val Pro Gly Arg Phe Ser Gly Ser
        50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys Arg Ala Ala Ala
            100                 105                 110

<210> SEQ ID NO 37
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 37

Gly Gly Gly Gly Ser Gly Gly Gly Ser Ser Gly Gly Ser Ser Ser
1               5                   10                  15

Gly Gly Gly Gly Ser Gly Gly Gly Gly Ser Ser Gly Gly Ser Gly
                20                  25                  30

Gly Gly Ser
        35

<210> SEQ ID NO 38
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 38

Ala Pro Pro Arg Leu Ile Cys Asp Ser Arg Val Leu Gln Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp

```
            50                  55                  60
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 39
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 39

Met Ala Gln Val Lys Leu Gln Gln Ser Gly Ala Glu Leu Val Lys Pro
 1               5                  10                  15

Gly Ala Ser Val Lys Leu Ser Cys Lys Ala Ser Gly Tyr Thr Phe Asn
             20                  25                  30

Ser Tyr Phe Met His Trp Met Lys Gln Arg Pro Val Gln Gly Leu Glu
         35                  40                  45

Trp Ile Gly Met Ile Arg Pro Asn Gly Gly Thr Thr Asp Tyr Asn Glu
     50                  55                  60

Lys Phe Lys Asn Lys Ala Thr Leu Thr Val Asp Lys Ser Ser Asn Thr
 65                  70                  75                  80

Ala Tyr Met Gln Leu Asn Ser Leu Thr Ser Gly Asp Ser Ala Val Tyr
                 85                  90                  95

Tyr Cys Ala Arg Trp Glu Gly Ser Tyr Tyr Ala Leu Asp Tyr Trp Gly
            100                 105                 110

Gln Gly Thr Thr Val Thr Val Ser Gly Gly Gly Gly Ser Gly Gly Gly
            115                 120                 125

Gly Gly Ser Ser Gly Gly Gly Ser Asp Ile Glu Leu Thr Gln
            130                 135                 140

Ser Pro Ala Ile Met Ser Ala Thr Leu Gly Glu Lys Val Thr Met Thr
145                 150                 155                 160

Cys Arg Ala Ser Ser Asn Val Lys Tyr Met Tyr Trp Tyr Gln Gln Lys
                165                 170                 175

Ser Gly Ala Ser Pro Lys Leu Trp Ile Tyr Tyr Thr Ser Asn Leu Ala
            180                 185                 190

Ser Gly Val Pro Gly Arg Phe Ser Gly Ser Gly Ser Gly Thr Ser Tyr
            195                 200                 205

Ser Leu Thr Ile Ser Ser Val Glu Ala Glu Asp Ala Ala Thr Tyr Tyr
            210                 215                 220

Cys Gln Gln Phe Thr Ser Ser Pro Tyr Thr Phe Gly Gly Gly Thr Lys
225                 230                 235                 240

Leu Glu Ile Lys Arg Ala Ala Ala Gly Gly Gly Gly Ser Gly Gly Gly
```

```
            245                 250                 255
Ser Ser Gly Gly Gly Ser Ser Gly Gly Gly Ser Gly Gly
            260                 265                 270
Gly Ser Ser Gly Gly Ser Gly Gly Gly Ser Ala Pro Pro Arg Leu
            275                 280             285
Ile Cys Asp Ser Arg Val Leu Gln Arg Tyr Leu Leu Glu Ala Lys Glu
        290                 295                 300
Ala Glu Asn Ile Thr Thr Gly Cys Ala Glu His Cys Ser Leu Asn Glu
305                 310                 315                 320
Asn Ile Thr Val Pro Asp Thr Lys Val Asn Phe Tyr Ala Trp Lys Arg
                325                 330                 335
Met Glu Val Gly Gln Gln Ala Val Glu Val Trp Gln Gly Leu Ala Leu
                340                 345                 350
Leu Ser Glu Ala Val Leu Arg Gly Gln Ala Leu Leu Val Asn Ser Ser
                355                 360                 365
Gln Pro Trp Glu Pro Leu Gln Leu His Val Asp Lys Ala Val Ser Gly
            370                 375                 380
Leu Arg Ser Leu Thr Thr Leu Leu Arg Ala Leu Gly Ala Gln Lys Glu
385                 390                 395                 400
Ala Ile Ser Pro Pro Asp Ala Ala Ser Ala Ala Pro Leu Arg Thr Ile
                405                 410                 415
Thr Ala Asp Thr Phe Arg Lys Leu Phe Arg Val Tyr Ser Asn Phe Leu
                420                 425                 430
Arg Gly Lys Leu Lys Leu Tyr Thr Gly Glu Ala Cys Arg Thr Gly Asp
            435                 440                 445
Arg
```

<210> SEQ ID NO 40
<211> LENGTH: 1347
<212> TYPE: DNA
<213> ORGANISM: Artificial Sequence
<220> FEATURE:
<223> OTHER INFORMATION: Synthetic Polynucleotide

<400> SEQUENCE: 40

```
atggctcaag ttaagttgca acaatctggt gctgaattgg ttaagccagg tgcttctgtt      60
aagttgtctt gtaaggcttc tggttacacc ttcaactctt actttatgca ttggatgaag     120
caaagaccag ttcaaggttt ggaatggatt ggtatgatta ccaaacggg tggtactacc      180
gattacaacg agaagtttaa gaacaaggct actttgactg ttgataagtc ctctaacact     240
gcttacatgc aattgaactc tttgacttct ggtgattctg ctgtttacta ctgtgctaga     300
tgggaaggtt cttactacgc tttggattac tggggtcaag gtaccactgt tactgttttct    360
tccggtggag gtggatctgg tggtggagga tcttcaggag gtggtggatc ttccgatatt     420
gagttgactc aatctccagc tattatgtct gctaccttgg gtgagaaggt tactatgact     480
tgtagagctt catctaacgt taagtacatg tactggtacc aacagaagtc tggtgcttct     540
ccaaagttgt ggatttacta cacttctaac ttggcttctg gtgttccagg tagattttct     600
ggttcaggtt ctggtacttc ctactctttg actatttcct ctgttgaagc tgaagatgct     660
gctacttact actgtcaaca attcacttct tcccccataca cttttggagg aggtactaag     720
ttggaaatca agagagctgc cgcaggtgga ggtggttccg gaggaggatc ttccggtggt     780
ggatcttctt ctggaggtgg aggatccggt ggtggaggat catctggtgg aggatctggt     840
ggtggttccg ctccacctag attgatttgt gattccagag ttttggaaag atacttgttg     900
```

-continued

```
gaagctaagg aggctgaaaa gattactact ggttgtgctg aacattgttc tttgaacgag    960
aagattactg ttccagatac taaggttaac ttttacgctt ggaagagaat ggaagttggt   1020
cagcaagctg ttgaagtttg gcaaggtttg gctttgttgt ctgaagctgt tttgagaggt   1080
caagctttgt tggttaagtc ttctcaacca tgggaaccat tgcaattgca tgttgataag   1140
gctgtttctg gtttgagatc tttgactacc ttgttgagag ctttgggtgc tcaaaaggaa   1200
gctatttctc ctccagatgc tgcttctgcc gctccattga gaactattac tgctgatact   1260
tttagaaagt tgtttagagt ttactctaac ttcttgagag gtaagttgaa gttgtacact   1320
ggtgaagctt gtagaactgg tgataga                                       1347
```